United States Patent
Kho et al.

(10) Patent No.: US 7,846,963 B2
(45) Date of Patent: *Dec. 7, 2010

(54) 2-OXO-HETEROCYCLIC COMPOUNDS AND THE PHARMACEUTICAL COMPOSITIONS COMPRISING THE SAME

(75) Inventors: Yung Hee Kho, Daejeon (KR); Gyoon Hee Han, Gyeonggi-do (KR); Ho Jae Lee, Daejeon (KR); Bum Woo Park, Seoul (KR); Hyo Kon Chun, Daejeon (KR); Hwan Mook Kim, Daejeon (KR); Song Kyu Park, Daejeon (KR); Sang Bae Han, Chungcheongbuk-do (KR); Dong Kyu Ryu, Daejeon (KR); Tae Gyu Chun, Daejeon (KR); Jin Ha Lee, Daejeon (KR); Chang Woo Lee, Daejeon (KR); Ki Hoon Lee, Daejeon (KR); Hee Yoon Lee, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 858 days.

This patent is subject to a terminal disclaimer.

(21) Appl. No.: 10/557,085

(22) PCT Filed: May 17, 2004

(86) PCT No.: PCT/KR2004/001169

§ 371 (c)(1),
(2), (4) Date: Sep. 19, 2006

(87) PCT Pub. No.: WO2004/101523

PCT Pub. Date: Nov. 25, 2004

(65) Prior Publication Data

US 2007/0167486 A1    Jul. 19, 2007

(30) Foreign Application Priority Data

| May 17, 2003 | (KR) | 10-2003-0031450 |
| May 17, 2003 | (KR) | 10-2003-0031451 |
| May 6, 2004  | (KR) | 10-2004-0031841 |
| May 7, 2004  | (KR) | 10-2004-0032263 |
| May 12, 2004 | (KR) | 10-2004-0033387 |
| May 12, 2004 | (KR) | 10-2004-0033388 |

(51) Int. Cl.
A01N 43/36   (2006.01)
A61K 31/40   (2006.01)
C07D 207/00  (2006.01)
C07D 295/00  (2006.01)
C09B 1/00    (2006.01)

(52) U.S. Cl. .................. 514/423; 514/183; 548/530; 548/400

(58) Field of Classification Search .................. 514/282
See application file for complete search history.

(56) References Cited

U.S. PATENT DOCUMENTS

| 5,281,585 A  | 1/1994  | Duggan    |
| 6,110,930 A  | 8/2000  | Taniguchi |
| 6,303,613 B1 | 10/2001 | McInally  |
| 6,476,023 B1 | 11/2002 | Cirillo   |

FOREIGN PATENT DOCUMENTS

| EP | 870763 A1      |   | 10/1998 |
| GB | 2268934 A      |   | 1/1994  |
| GB | 1042640        |   | 9/1996  |
| WO | PCT/GB89/01398 |   | 5/1990  |
| WO | PCT/GB92/00230 |   | 8/1992  |
| WO | PCT/US92/03809 |   | 10/1992 |
| WO | PCT/GB93/01556 |   | 3/1994  |
| WO | PCT/GB94/00808 |   | 10/1994 |
| WO | PCT/GB94/02145 |   | 4/1995  |
| WO | PCT/US97/00523 |   | 9/1997  |
| WO | WO 97/32846    | * | 9/1997  |
| WO | 97/36900       |   | 10/1997 |
| WO | 98/45294       |   | 10/1998 |

OTHER PUBLICATIONS

J. Bone Joint Surg . 52A , pp. 424-434, 1970.
Clin. Exp. Immunol. 81 , p. 301, 1990.
Nature, 370 , p. 555, 1994.
Journal of Organic Chemistry, 1996, vol. 61, No. 7, pp. 2283-2292.
Canadian Journal of Chemistry, 1983, vol. 61, No. 9, pp. 2016-2021.
Tetrahedron Letters (1995), (No. 5), 4-9.
Lee, D. et al., alpha-Methylenelactam rearrangement, 1974, J. Org. Chem., vol. 39, No. 7, 893-902.
Hirata, T. et al., 1959, The structure of Cypridina Luciferin, Tetrahedron Letters, No. 5, pp. 4-9.
EP Search Report, Feb. 4, 2009.
Supplementary EP Search Report, Jul. 3, 2008.

* cited by examiner

*Primary Examiner*—James D Anderson
*Assistant Examiner*—Meghan Finn
(74) *Attorney, Agent, or Firm*—Kirk Hahn

(57) ABSTRACT

The present invention is related to new 2-oxo-cyclic compound the process for preparing them and a pharmaceutical composition comprising the same. The present invention provides a pharmaceutical composition for preventing and treating the inflammatory disease comprising the pain or inflammation caused by rheumatic disease, for example, rheumatoid arthritis, spondyloarthopathies, gout, osteoarthritis, systemic lupus erythematosus and juvenile arthritis, and inflammatory syndrome for example, from myositis, gingivitis, synovitis, ankylosing spondylitis, bursitis, burns and scar, inflammatory Crohn's disease, Types I diabetes. therefore, it can be used as the therapeutics for treating and preventing inflammatory diseases.

9 Claims, No Drawings

2-OXO-HETEROCYCLIC COMPOUNDS AND THE PHARMACEUTICAL COMPOSITIONS COMPRISING THE SAME

This application is the U.S. National Phase under 35 U.S.C. §371 of International Application PCT/KR2004/001169, filed on May 17, 2004, which claims priority to Korean Patent Application No. 10-2003-0031451, 10-2003-0031450, 10-2004-0031841, 10-2004-0032263, 10-2004-0033388 and 10-2004-0033387, filed on May 17, 2003, May 17, 2003, May 6, 2004, May 7, 2004, May 12, 2004 and May 12, 2004, respectively. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to novel 2-oxo-heterocyclic compounds as a potent anti-inflammatory agent and the pharmaceutical compositions comprising the same.

BACKGROUND ART

The inflammation caused by mechanical scars or various infection of bacteria et al is a normal response of human body associated with an edema, a pain etc. Generally, the syndrome of arthritic inflammation occurs temporally, however, it causes to long-term and eventual deformity if it is progressed to be severe. The arthritic disease can be classified into several diseases according to the respective disease such as rheumatoid arthritis (RA), rheumatic inflammation related disease etc. Among them, in particular, arthritic inflammation is the most frequently occurred and chronic disease characterized in the inflammatory change at the synovial membrane of the inner layer of articular capsule, which may progress to effect on all the joints of human body and become worse to be a disabled person. A progressive arthritic disease such as rheumatic arthritis gives rise to joint obstacle such as a joint aberrance and acampsia, which often results in severe physical disorder caused by the absence of effective treatment and continuous aggravation of the disease.

It has been known that osteoarthritis (OA) correlates with complex and multi-factors, however, most important factor among them is the inflammation of synovial fluid. The injury of synovial fluid may promotes the dissociation of proteoglycan (PG) as a result of the interaction between synovial cells and cartilage cells. The activated synovial cells reproduce numerous factors which may induce the loss of articular cartilage, for example, interleukin-1, tumor necrosis factor (TNF-alpha) and prostaglandins. The direct injury of cartilage cells further accelerates the reproduction of matrix metalloprotease (MMP) activating enzymes such as collagenase, stromelysin and gelatinase and various inflammatory mediators. Wherever the function of joint cartilage reduces, it gives rise to occurring OA diseases. The decrease of PGs at OA joint tissue reduces the resilence of cartilage, which endows cartilage cell, subcartilaginous osteocyte and synovial cell with a mechanical stress.

Both of OA and rheumatic arthritis (RA) are representative diseases destructing joint cartilage and being characterized in topical erosion of cartilage surface. For example, it has been reported that the introduction of radio-labeled sulfuric acid salt into the femoral joint cartilage of OA patients is significantly decreased compared with that of control group, which indicates that the dissociating rate of cartilage in OA patient is increased (Mankin et al., *J. Bone Joint Surg.*, 52A, pp 424-434, 1970).

Four types of proteinase, i.e., serine, cystein, aspartic acid and metalloprotease exist in mammalian cell. The metalloprotease, one of the proteinase, has been reported to be an important factor for the extra-cellular substrate hydrolyzing action of joint cartilage in OA and RA patients and further the increased activity of collagenase and stromelysin has been found in the cartilage of OA patient, of which activity is closely interrelated with the severity of OA or RA disease (Mankin et al., *Arthritis Rheum.*, 21, pp 761-766, (1978); Woessner et al., *Arthritis Rheum.*, 26, pp 63-68, (1983) and Ibid., 27, pp 305-312, (1984)). Agrekanase has been also found in OA and RA patient recently and it shows metalloprotease enzyme similar activity and provides with the specific fragmented product of proteoglycans (Lohmander L. S. et al., *Arthrits Rheum.*, 36, pp 1214-1222, 1993), TNF (Tumor Necrosis Factor), a cytokine bound to cells, is processed from 36 kD precursor type to 17 kD activated or thereof. It has been found that TNF is a first controlling factor of acute phase response similar to the phenomenon occurred during inflammation, fever, acute infection and shock in human and animal, therefore the excess reproduction of TNF could be a cause of death. At present, it has been reported that the prevention of TNF reproduction could treat various diseases together with autoimmune disease such as rheumatoid arthritis (RA), insulin-independent diabetes and Crohn's disease (Lohmander L. S. et al., *Arthritis Rheum.*, 36, pp 1214-1222, 1993; Macdonald T. et al., *Clin. Exp. Immunol.*, 81, p 301, 1990).

Accordingly, the reproduction inhibitors of TNF have potentially therapeutic importance in the treatment of inflammatory diseases. Recently, matrix metalloprotease as well as other metalloproteases known to be as TNF-C (Tumor Necrosis Factor-Convertase, can be transformed from inactivated form thereof into activated form thereof (Gearing et al., *Nature*, 370, p 555 1994), therefore the inhibiting either the transformation of MPs or the release of activated TNF-alpha from the cell thereby may be an important mechanism in the treatment of inflammatory diseases.

Since the overproduction of TNF is a distinguished phenomenon in lots of diseases having characteristic of the tissue lysis mediated by MMP, the inhibitor of both MMP and TNF has favorable advantage in the treatment of specific inflammatory diseases correlated with both mechanism.

PCT WO 92/213260 A1 discloses N-carboxyalkylpeptidyl compounds useful as an enzyme inhibitor of hydroxamates and carboxylates matrix MMP; PCT WO 90/05716 A1 and PCT WO 92/13831 A1 disclose an hydroxamate matrix collagenase inhibitor; PCT WO 94/2446 A1 discloses natural amino acid derivatives useful as an MMP inhibitor; PCT WO 95/9841 A1 discloses hydroxamate derivatives useful as a cytokine inhibitor; GB A 2,268, 934 and PCT WO 94/24140 A1 disclose a hydroxamate inhibitor of MMP inhibiting TNF reproduction, the disclosure of which cited documents are incorporated herein by reference.

To treat RA or OA disease, conventional drugs for example, steroids such as cortisone and other ACTH (adrenocorticotrophic hormone); NSAID (Non-steroidal anti-inflammatory drug) such as aspirin, piroxicam, indomethacin etc; gold agents such as aurothioglucose, gold sodium thiomalate an auranofin etc; anti-rheumatic drug such as chloroquinone, D-penicillamine etc; gout inhibitors such as colchicines; and immuno-suppressing agents such as cyclophosphamide, azathioprine, methotrexate, levamisole etc have been prescribed till now. However, the treatment with conventional drugs has not provided with satisfactory efficacy and has various adverse effects, which limits the usage of conventional drugs.

For example, anti-inflammatory drugs such as asprin or butazolin have been used to alleviate the syndrome of OA and RAs, however, the consistent administration of the drugs is difficult because of their adverse effects, for example, i.e., severe stomach irritation resulting in gastritis, stomach ulcer etc.

Accordingly, there have been studied and investigated to develop new satisfactory anti-rheumatic agents which can solve the problems of conventional drugs, in particular, which can improve anti-inflammatory efficacy and provide with safe long-term administration without adverse action till now.

Present inventors extensively investigated to find new compounds showing strong inhibiting activity for the reproduction of NO and TNF-alpha, finally found new 2-oxo-heterocyclic compounds showing potent inhibition effects on the reproduction of NO and TNF-alpha, and completed present invention.

SUMMARY OF THE INVENTION

The present invention provides a novel 2-oxo-heterocyclic compound and the pharmacologically acceptable salt thereof showing strong inhibiting activity for the reproduction of NO and TNF-alpha.

The present invention also provides a pharmaceutical composition comprising a novel 2-oxo-heterocyclic compound and the pharmacologically acceptable salt thereof as an active ingredient in an effective amount to treat and prevent inflammation diseases.

The present invention also provides a use of novel 2-oxo-heterocyclic compound and the pharmacologically acceptable salt thereof for the preparation of pharmaceutical composition to treat and prevent inflammatory diseases.

DISCLOSURE OF THE INVENTION

Thus, the present invention provides a novel compound represented by the following general formula (I), and the pharmaceutically acceptable salt:

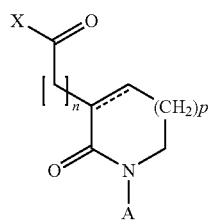

(I)

wherein
X is a hydroxyl group, —NHOH, —NHOCH$_2$Ph,

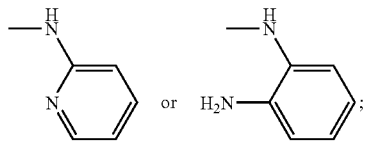

A is an hydrogen, A1 group or

(A2)

A1 is a lower alkyl, lower alkenyl, lower alkynyl, lower allyl group having C1 to C5 carbon atoms, a heterocyclic group or aromatic aryl group, preferably, the group selected from thiophenyl group, naphtyl group, pyrrolyl group, furyl group and biphenyl group, wherein Y is a lower alkyl group, lower alkoxy group, nitro, halogen, amine, acetamide, carbonamide or sulfonamide group, M is a lower alkyl group or phenyl group substituted with R', of which R' is a hydrogen, lower alkyl or lower alkoxy group, m and r is independently an integer of 1 to 5 respectively in A2 residue;

p is an integer of 0, 1 or 2;
n is an integer of 1 to 5;
dotted line (.....) means single bond or double bond.

In preferred embodiment, the present invention also provides the compounds represented by following general formula (II), the pharmaceutically acceptable salt or the isomer thereof:

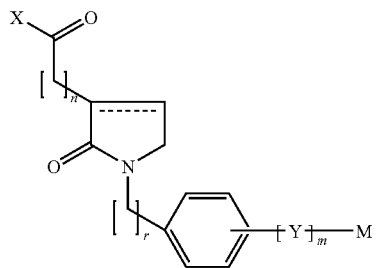

(II)

wherein
X is a hydroxyl group, —NHOH, —NHOCH$_2$Ph,

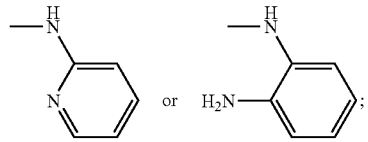

Y is a lower alkyl group, lower alkoxy group, nitro, halogen, amine, acetamide, carbonamide or sulfonamide group;

M is a lower alkyl group or phenyl group substituted with R', of which R' is a hydrogen, lower alkyl or lower alkoxy group;

m and r is independently an integer of 1 to 5 respectively;
n is an integer of 1 to 5;
dotted line (.....) means single bond or double bond.

The preferred compounds of general formula (II) is one selected from the group consisting of;

3-[1-(2,4-Dimethoxybenzyl)-2-oxo-2,5-dihydro-1H-pyrrol-3-yl]-N-hydroxypropionamide, 3-(1-benzyl-2-oxo-2,5-dihydro-1H-pyrrol-3-yl)-N-hydroxypropionamide, N-hydroxy-3-(2-oxo-1-phenethyl-2,5-dihydro-1H-pyrrol-3-yl)-propionamide, N-hydroxy-3-[2-oxo-1-(3-phenyl-propyl)-2,5-dihydro-1H-pyrrol-3-yl]-propionamide, N-hydroxy-3-[2-oxo-1-(4-phenyl-butyl)-2,5-dihydro-1H-pyrrol-3-yl]propionamide, N-hydroxy-3-[1-(2-methyl-benzyl)-2-oxo-2,5-dihydro-1H-pyrrol-3-yl]-propionamide, N-hydroxy-3-[1-(3-methyl-benzyl)-2-oxo-2,5-dihydro-1H-pyrrol-3-yl]-propionamide, N-hydroxy-3-[1-(4-methyl-benzyl)-2-oxo-2,5-dihydro-1H-pyrrol-3-yl]-propionamide, N-hydroxy-3-[1-(2-methoxy-benzyl)-2-oxo-2,5-dihydro-1H-pyrrol-3-yl]-propionamide, N-hydroxy-3-[1-(3-methoxy-benzyl)-2-oxo-2,5-dihydro-1H-pyrrol-3-yl]-propionamide,
N-hydroxy-3-[1-(4-methoxy-benzyl)-2-oxo-2,5-dihydro-1H-pyrrol-3-yl]-propionamide,
3-[1-(4-bromo-benzyl)-2-oxo-2,5-dihydro-1H-pyrrol-3-yl]-N-hydroxy-propionamide,
3-[1-(4-chloro-benzyl)-2-oxo-2,5-dihydro-1H-pyrrol-3-yl]-N-hydroxy-propionamide,
3-[1-(4-benzyloxy-benzyl)-2-oxo-2,5-dihydro-1H-pyrrol-3-yl]-N-hydroxy-propionamide,
N-hydroxy-3-[1-(4-nitro-benzyl)-2-oxo-2,5-dihydro-1H-pyrrol-3-yl]-propionamide,
3-[1-(2,4-dimethoxy-benzyl)-2-oxo-2,5-dihydro-1H-pyrrol-3-yl]-propionic acid,
3-(1-benzyl-2-oxo-2,5-dihydro-1H-pyrrol-3-yl)-propionic acid,
N-{4-[3-(2-hydroxycarbamoyl-ethyl)-2-oxo-2,5-dihydro-pyrrole-1-yl-methyl]-phenyl}-benzamide,
N-hydroxy-3-{2-oxo-1-[4-(toluene-4-sulfonylamino)-benzyl]-2,5-dihydro-1H-pyrrol-3-yl}-propionamide,
2-(1-benzyl-2-oxo-2,5-dihydro-1H-pyrrol-3-yl)-N-hydroxy-acetamide,
2-[1-(2,4-dimethoxy-benzyl)-2-oxo-2,5-dihydro-1H-pyrrol-3-yl]-N-hydroxy-acetamide,
N-hydroxy-2-(2-oxo-1-phenethyl-2,5-dihydro-1H-pyrrol-3-yl)-acetamide,
N-hydroxy-2-[2-oxo-1-(4-phenyl-butyl)-2,5-dihydro-1H-pyrrol-3-yl]-acetamide,
2-[1-(4-benzyloxy-benzyl)-2-oxo-2,5-dihydro-1H-pyrrol-3-yl]-N-hydroxy-acetamide,
2-(1-benzyl-2-oxo-pyrrolidin-3-yl)-N-hydroxy-acetamide,
2-[1-(2,4-dimethoxy-benzyl)-2-oxo-pyrrolidin-3-yl]-N-hydroxy-acetamide,
N-hydroxy-2-(2-oxo-1-phenethyl-pyrrolidin-3-yl)-acetamide,
3-{1-[2-(2-fluoro-phenyl)-ethyl]-2-oxo-2,5-dihydro-1H-pyrrol-3-yl}-N-hydroxy-propionamide,
3-{-[2-(3-fluoro-phenyl)-ethyl]-2-oxo-2,5-dihydro-1H-pyrrol-3-yl}-N-hydroxy-propionamide,
3-{1-[2-(4-fluoro-phenyl)-ethyl]-2-oxo-2,5-dihydro-1H-pyrrol-3-yl}-N-hydroxy-propionamide,
N-hydroxy-3-{1-[2-(2-nitro-phenyl)-ethyl]-2-oxo-2,5-dihydro-1H-pyrrol-3-yl}-propionamide,
N-hydroxy-3-{1-[2-(3-nitro-phenyl)-ethyl]-2-oxo-2,5-dihydro-1H-pyrrol-3-yl}-propionamide,
N-hydroxy-3-{1-[2-(4-nitro-phenyl)-ethyl]-2-oxo-2,5-dihydro-1H-pyrrol-3-yl}-propionamide,
3-{1-[2-(2-bromo-phenyl)-ethyl]-2-oxo-2,5-dihydro-1H-pyrrol-3-yl}-N-hydroxy-propionamide,
3-{1-[2-(4-bromo-phenyl)-ethyl]-2-oxo-2,5-dihydro-1H-pyrrol-3-yl}-N-hydroxy-propionamide,
N-hydroxy-3-{1-[2-(2-methoxy-phenyl)-ethyl]-2-oxo-2,5-dihydro-1H-pyrrol-3-yl}-propionamide,
N-hydroxy-3-{1-[2-(3-methoxy-phenyl)-ethyl]-2-oxo-2,5-dihydro-1H-pyrrol-3-yl}-propionamide,
N-hydroxy-3-{1-[2-(4-methoxy-phenyl)-ethyl]-2-oxo-2,5-dihydro-1H-pyrrol-3-yl}-propionamide,
N-hydroxy-3-[2-oxo-1-(2-p-tolyl-ethyl)-2,5-dihydro-1H-pyrrol-3-yl]-propionamide,
N-hydroxy-3-{1-[3-(4-methoxy-phenyl)-propyl]-2-oxo-2,5-dihydro-1H-pyrrol-3-yl}-propionamide,
N-hydroxy-3-[2-oxo-1-(3-o-tolyl-propyl)-2,5-dihydro-1H-pyrrol-3-yl]-propionamide,
N-hydroxy-3-[2-oxo-1-(3-m-tolyl-propyl)-2,5-dihydro-1H-pyrrol-3-yl]-propionamide,
N-hydroxy-3-{1-[3-(4-isopropyl-phenyl)-propyl]-2-oxo-2,5-dihydro-1H-pyrrol-3-yl]-propionamide,
3-{1-[3-(4-bromo-phenyl)-propyl]-2-oxo-2,5-dihydro-1H-pyrrol-3-yl]-N-hydroxy-propionamide,
3-{1-[3-(4-chloro-phenyl)-propyl]-2-oxo-2,5-dihydro-1H-pyrrol-3-yl]-N-hydroxy-propionamide,
N-hydroxy-3-{1-[3-(4-methoxy-phenyl)-propyl]-2-oxo-2,5-dihydro-1H-pyrrol-3-yl]-propionamide,
N-hydroxy-3-{1-[3-(2-methoxy-phenyl)-propyl]-2-oxo-2,5-dihydro-1H-pyrrol-3-yl]-propionamide,
N-hydroxy-3-{1-[3-(3-methoxy-phenyl)-propyl]-2-oxo-2,5-dihydro-1H-pyrrol-3-yl]-propionamide.

In preferred embodiment, the present invention also provides the compounds represented by following general formula (III), the pharmaceutically acceptable salt or the isomer thereof:

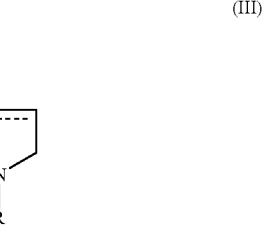

(III)

wherein
X is a hydroxyl group, —NHOH, —NHOCH$_2$Ph,

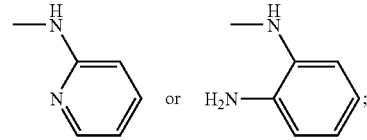

R is a lower alkyl, lower alkenyl, lower alkynyl, lower allyl group having C1 to C5 carbon atoms, a heterocyclic group or aromatic aryl group, preferably, the group selected from thiophenyl group, naphtyl group, pyrrolyl group, furyl group and biphenyl group;
n is an integer of 1 to 5;
dotted line (.....) means single bond or double bond.

The preferred compounds of general formula (III) is one selected from the group consisting of;
N-hydroxy-3-(1-naphthalene-2-ylmethyl-2-oxo-2,5-dihydro-1H-pyrrol-3-yl)-propionamide,
N-hydroxy-3-(1-methyl-2-oxo-2,5-dihydro-1H-pyrrol-3-yl)-propionamide,
3-(1-allyl-2-oxo-2,5-dihydro-1H-pyrrol-3-yl)-N-hydroxy-propionamide,
N-hydroxy-3-[1-(2-naphthalene-1-yl-ethyl)-2-oxo-2,5-dihydro-1H-pyrrol-3-yl]-propionamide,
N-hydroxy-3-[1-(2-naphthalene-2-yl-ethyl)-2-oxo-2,5-dihydro-1H-pyrrol-3-yl]-propionamide,
N-hydroxy-3-[2-oxo-1-(2-thiophen-2-yl-ethyl)-2,5-dihydro-1H-pyrrol-3-yl]-propionamide,
3-[1-(3-biphenyl-4-yl-propyl)-2-oxo-2,5-dihydro-1H-pyrrol-3-yl]-N-hydroxy-propionamide,
N-hydroxy-3-[1-(3-naphthalene-2-yl-propyl)-2-oxo-2,5-dihydro-1H-pyrrol-3-yl]-propionamide.

In preferred embodiment, the present invention also provides the compounds represented by following general formula (IV), the pharmaceutically acceptable salt or the isomer thereof:

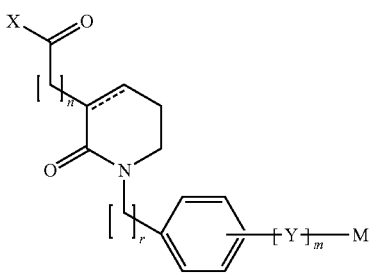

(IV)

wherein
X is a hydroxyl group, —NHOH, —NHOCH₂Ph,

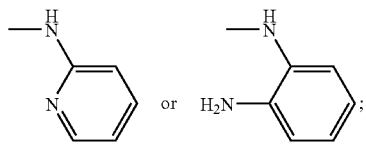

Y is a lower alkyl group, lower alkoxy group, nitro, halogen, amine, acetamide, carbonamide or sulfonamide group;

M is a lower alkyl group or phenyl group substituted with R', of which R' is a hydrogen, lower alkyl or lower alkoxy group;

m and r is independently an integer of 1 to 5 respectively;
n is an integer of 1 to 5;
dotted line (.....) means single bond or double bond.

The preferred compounds of general formula (IV) is one selected from the group consisting of;

3-[1-(2,4-Dimethoxybenzyl)-2-oxo-1,2,5,6-tetrahydropyridin-3-yl]-N-hydroxypropionamide,
N-hydroxy-3-(1-benzyl-2-oxo-1,2,5,6-tetrahydro-pyridin-3-yl)-propionic acid,
N-hydroxy-3-[1-(4-nitro-benzyl)-2-oxo-1,2,5,6-tetrahydro-pyridin-3-yl]-propionamide,
3-(1-benzyl-2-oxo-1,2,5,6-tetrahydro-pyridin-3-yl)-N-hydroxy propionamide,
N-hydroxy-3-[2-oxo-1-(4-phenyl-butyl)-1,2,5,6-tetrahydro-pyridin-3-yl]-propionamide,
N-hydroxy-3-(2-oxo-1-phenethyl-1,2,5,6-tetrahydro-pyridin-3-yl)-propionamide,
3-[1-(2,4-dimethoxybenzyl)-2-oxo-1,2,5,6-tetrahydro-pyridin-3-yl)-propionic acid,
3-(1-benzyl-2-oxo-1,2,5,6-tetrahydro-pyridin-3-yl)-propionic acid,
3-[1-(4-nitro-benzyl)-2-oxo-1,2,5,6-tetrahydro-pyridin-3-yl)-propionic acid,
3-[2-oxo-1-(3-phenyl-propyl)-1,2,5,6-tetrahydro-pyridin-3-yl)-propionic acid,
3-[2-oxo-1-(4-phenyl-butyl)-1,2,5,6-tetrahydro-pyridin-3-yl)-propionic acid,
3-(2-oxo-1-phenethyl-1,2,5,6-tetrahydro-pyridin-3-yl)-propionic acid,
3-(1-benzyl-2-oxo-1,2,5,6-tetrahydro-pyridin-3-yl)-N-pyridin-2-yl-propionamide,
N-(2-amino-phenyl)-3-(1-benzyl-2-oxo-1,2,5,6-tetrahydro-pyridin-3-yl)-propionamide,
N-(2-amino-phenyl)-3-[1-(2-methyl-benzyl)-2-oxo-1,2,5,6-tetrahydro-pyridin-3-yl)-propionamide,
N-(2-amino-phenyl)-3-[1-(2-methyl-benzyl)-2-oxo-1,2,5,6-tetrahydro-pyridin-3-yl)-propionamide,
N-benzyloxy-3-(2-oxo-1-phenethyl-1,2,5,6-tetrahydro-pyridin-3-yl)-propionamide,
3-[1-(4-acetylamino-benzyl)-2-oxo-1,2,5,6-tetrahydro-pyridin-3-yl)-N-hydroxy-propionamide,
N-4-[5-(2-hydroxycarbamoyl-ethyl)-6-oxo-3,6-dihydro-2-pyridin-1-yl-methyl]-phenyl-benzamide,
N-hydroxy-3-[1-(4-dimethylsulfonylamino-benzyl)-2-oxo-1,2,5,6-tetrahydro-pyridin-3-yl]-propionamide,
N-hydroxy-3-2-oxo-1-[4-(toluene-4-sulfonylamino)-benzyl-1,2,5,6-tetrahydro-pyridin-3-yl]-propionamide,
3-[1-(4-acetylamino-benzyl)-2-oxo-1,2,5,6-tetrahydro-pyridin-3-yl]-propionic acid,
3-[1-(4-benzoylamino-benzyl)-2-oxo-1,2,5,6-tetrahydro-pyridin-3-yl]-propionic acid,
3-2-oxo-1-[4-(toluene-4-sulfonylamino)-benzyl]-2-oxo-1,2,5,6-tetrahydro-pyridin-3-yl]-propionic acid,
N-hydroxy-3-(2-oxo-1-phenethyl-piperidine-3-yl)-propionamide,
2-[1-(2,4-dimethoxy-benzyl)-2-oxo-1,2,5,6-tetrahydro-pyridin-3-yl]-N-hydroxy-acetamide,
2-(1-benzyl-2-oxo-1,2,5,6-tetrahydro-pyridin-3-yl)-N-hydroxy-acetamide,
N-hydroxy-2-[1-(4-nitro-benzyl)-2-oxo-1,2,5,6-tetrahydro-pyridin-3-yl]-N-hydroxy-acetamide,
N-hydroxy-2-[2-oxo-1-(3-phenyl-propyl)-1,2,5,6-tetrahydro-pyridin-3-yl]-N-hydroxy-acetamide,
N-hydroxy-2-[2-oxo-1-(4-phenyl-butyl)-1,2,5,6-tetrahydro-pyridin-3-yl]-N-hydroxy-acetamide,
[1-(2,4-dimethoxy-benzyl)-2-oxo-1,2,5,6-tetrahydro-pyridin-3-yl]-acetic acid,
(1-benzyl-2-oxo-1,2,5,6-tetrahydro-pyridin-3-yl)-acetic acid,
(2-oxo-1-phenethyl-1,2,5,6-tetrahydro-pyridin-3-yl)-acetic acid,
[2-oxo-1-(3-phenyl-propyl)-1,2,5,6-tetrahydro-pyridin-3-yl)-acetic acid,
[2-oxo-1-(4-phenyl-butyl)-1,2,5,6-tetrahydro-pyridin-3-yl)-acetic acid,
2-[1-(2,4-dimethoxy-benzyl)-2-oxo-piperidine-3-yl]-N-hydroxy-acetamide,
(2-oxo-1-phenethyl-piperidine-3-yl)-acetic acid,
[2-oxo-1-(3-phenyl-propyl)-piperidine-3-yl]-acetic acid,
4-[1-(4-methoxy-benzyl)-2-oxo-1,2,5,6-tetrahydro-pyridin-3-yl]-N-hydroxy-butylamide,
4-(1-phenethyl-2-oxo-1,2,5,6-tetrahydro-pyridin-3-yl)-N-hydroxy-butylamide,
N-hydroxy-4-[2-oxo-1-(3-phenyl-propyl)-1,2,5,6-tetrahydro-pyridin-3-yl]-butylamide,
N-hydroxy-4-[2-oxo-1-(3-phenyl-butyl)-1,2,5,6-tetrahydro-pyridin-3-yl]-butylamide.

In preferred embodiment, the present invention also provides the compounds represented by following general formula (V), the pharmaceutically acceptable salt or the isomer thereof:

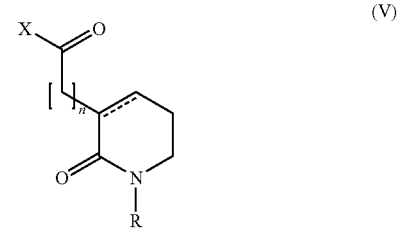

(V)

wherein
X is a hydroxyl group, —NHOH, —NHOCH₂Ph,

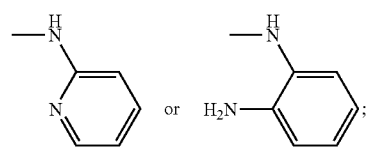

R is a lower alkyl, lower alkenyl, lower alkynyl, lower allyl group having C1 to C5 carbon atoms, a heterocyclic group or aromatic aryl group, preferably, the group selected from thiophenyl group, naphtyl group, pyrrolyl group, furyl group and biphenyl group;

n is an integer of 1 to 5;

dotted line (.....) means single bond or double bond.

The preferred compounds of general formula (V) is one selected from the group consisting of;

3-(2-oxo-1,2,5,6-tetrahydro-pyridin-3-yl)-propionic acid,

N-Benzyloxy-3-(2-oxo-1,2,5,6-tetrahydro-pyridin-3-yl)-propionamide, 3-(1-Allyl-2-oxo-1,2,5,6-tetrahydro-pyridin-3-yl)-N-hydroxy-propionamide, N-hydroxy-3-(1-methyl-2-oxo-1,2,5,6-tetrahydro-pyridin-3-yl)-propionamide, N-hydroxy-3-[1-(naphthalene-2-yl-methyl)-2-oxo-1,2,5,6-tetrahydro-pyridin-3-yl]-propionamide, N-hydroxy-3-[2-oxo-1-(2-thiophen-2-yl-ethyl)-1,2,5,6-tetrahydro-pyridin-3-yl]-propionamide.

It is another object of the present invention to provide the pharmaceutical composition comprising an efficient amount of the compound represented by general formula (I) to (V) or the pharmaceutically acceptable salt thereof as an active ingredient in amount effective to alleviate or treat pain diseases or inflammatory diseases together with pharmaceutically acceptable carriers or diluents.

The inventive compounds represented by general formula (I) to (V) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluenesulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by general formula (I) to (V) comprise all the acidic or basic salt, which may be presented at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate (mesylate) salt and p-toluenesulfonate (tosylate) salt etc, which can be prepared by the conventional method well known in the art.

There may exist in the form of optically different diastereomers since the compounds represented by general formula (I) to (V) have unsymmetrical centers, accordingly, the compounds of the present invention comprise all the optically active isomers, R or S stereoisomers and the mixtures thereof. Present invention also comprises all the uses of racemic mixture, more than one optically active isomer or the mixtures thereof as well as all the preparation or isolation method of the diastereomer well known in the art.

The compounds of the invention of formula (I) to (V) may be chemically synthesized by the methods explained by following reaction schemes hereinafter, which are merely exemplary and in no way limit the invention. The reaction schemes show the steps for preparing the representative compounds of the present invention, and other compounds also may be produced by the following steps with appropriate modifications of reagents and starting materials, which are envisaged by those skilled in the art.

General Synthetic Procedures

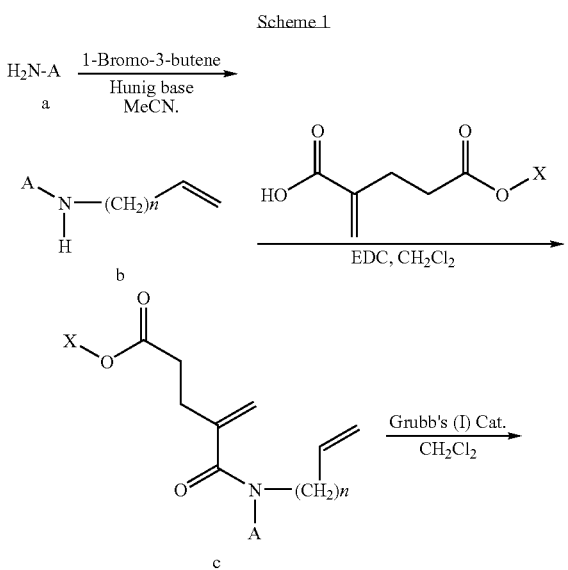

Scheme 1

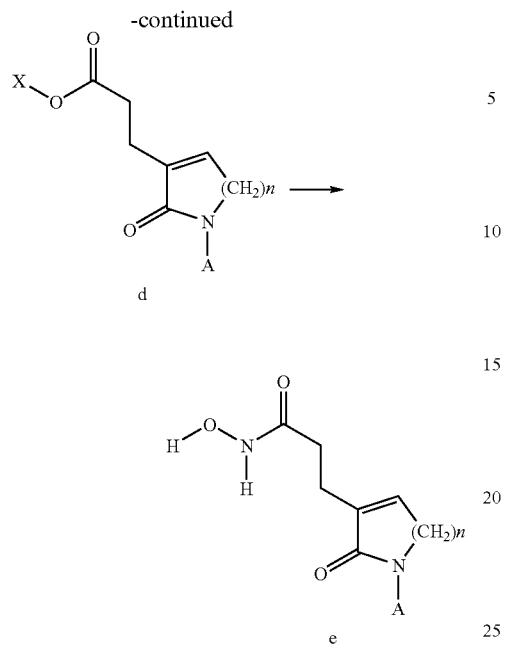

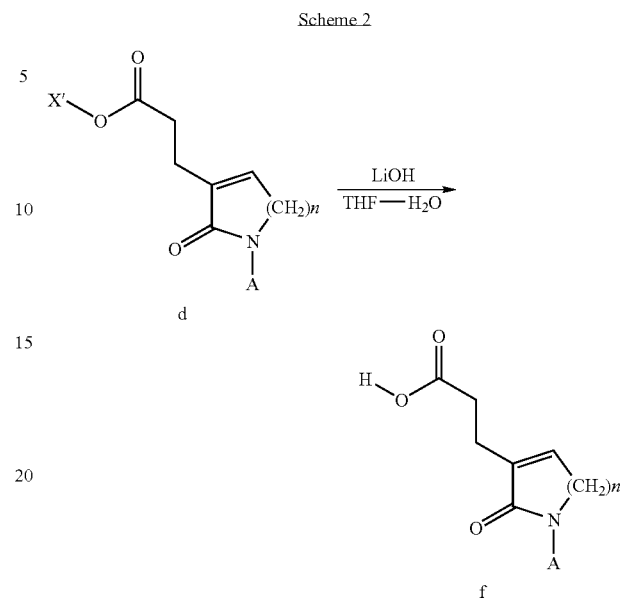

As depicted in above Scheme 1, the scheme explains the process for preparing hydroxamic acid compound (e) consisting of 4 steps;

At the $1^{st}$ step, compound (a) is reacted with 1-bromo-3-butene under organic solvent in the presence of Hunig base to synthesize compound (b). In this step, an organic solvent such as acetonitrile, dichloromethane etc is preferable and diethylisopropylamine can be used as a Hunig base in the amount of 2 to 3 equivalents to the compound (a). It is preferable the reaction is performed at the temperature ranging from 0° C. to room temperature (RT).

At the $2^{nd}$ step, the compound (b) obtained in step 1 is reacted with mono acid in the presence of 1-[3-(dimethylamino)propyl]-3-ethylcarbodiimide (EDC) under an organic solvent to synthesize the compound (c). In this step, an organic solvent such as dichloromethane, THF etc are preferable and the mono acid such as 2-methylene-pentandionic acis-5-methyl ester in the amount of 1 to 1.2 equivalents to the compound (b) is preferable. It is preferable the reaction is performed at the temperature ranging from 0° C. to RT.

At the $3^{rd}$ step, the compound (c) obtained in step 2 is converted into the compound (d) in the presence of Grubb's (1) catalyst such as Ruthenium catalyst under organic solvent. In this step, it is preferable to use the catalyst in the amount of 0.02 to 0.1 equivalents to the compound (c) at the temperature ranging from 0° C. to RT.

At the $4^{th}$ step, the compound (d) obtained in step 3 is reacted with amine salt to synthesize hydroxamic acid compound (e) in case that X is NHOH in general formula I compounds. In this step, it is preferable to use potassium hydroxyamide ($KONH_2$) in the amount of 2 to 3 equivalents to the compound (d) at the temperature ranging from 0° C. to RT.

As depicted in the above Scheme 2, the ester compounds (d) is reacted with hydroxide metal salt under the organic solvent such as THF to synthesize the carboxylic acid (f). In the reaction, it is preferable to use LiOH in the amount of 2 to 3 equivalents to the compound (d) at the temperature ranging from 0° C. to RT.

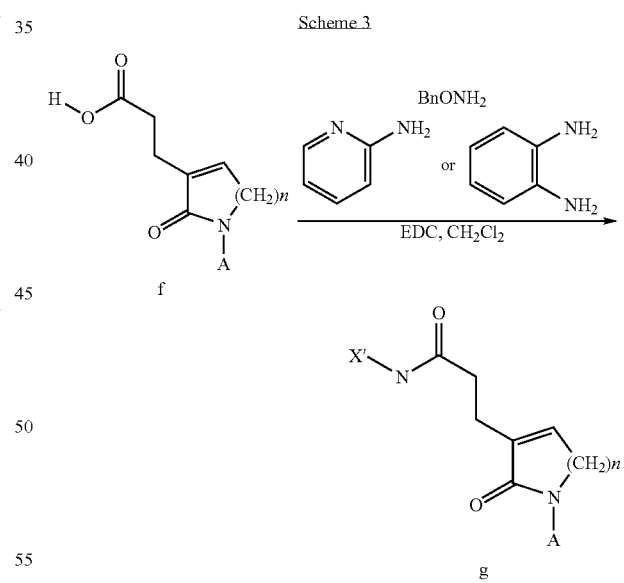

As depicted in the above Scheme 3, the carboxylic acid compound (f) obtained in Scheme 2 is reacted with benzyloxyamine ($BnONH_2$), pyridylamine or diaminobenzene in the presence of 1-[3-(dimethylamino)propyl]-3-ethylcarbodiimide (EDC) under organic solvent to synthesize the amide compounds of which X is benzyloxyamine ($BnONH_2$), pyridylamine or diaminobenzene group. In the reaction, it is preferable to use benzyloxyamine ($BnONH_2$), pyridylamine or diaminobenzene in the amount of 1 to 1.5 equivalents to the compound (f) at the temperature ranging from 0° C. to RT.

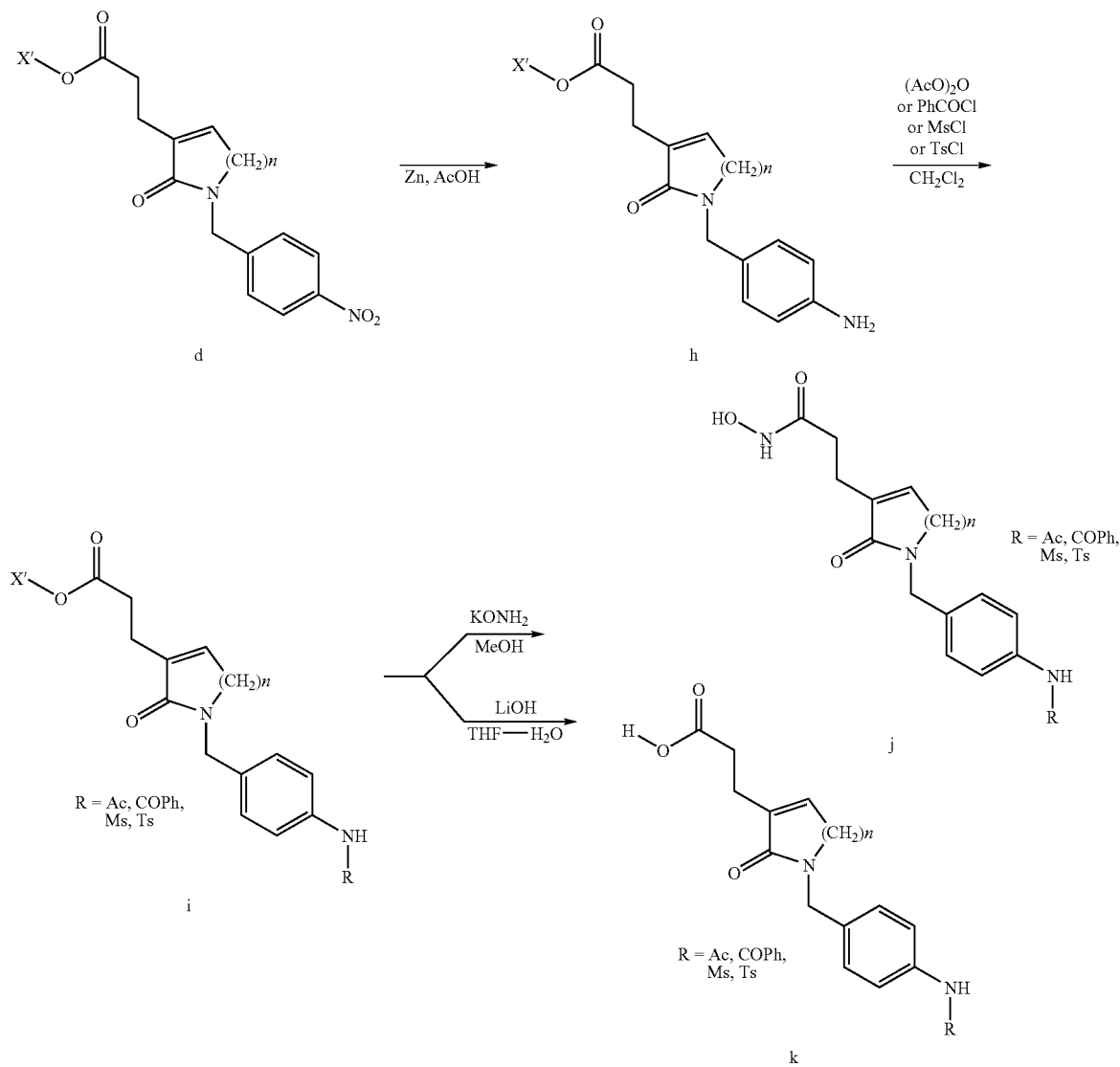

Scheme 4

As shown in the above Scheme 4, the hydroxyamide compound H) and carboxylic acid compound (k) are prepared by following procedure from the ester compounds (d):

At the $1^{st}$ step, the compound (d) prepared from Scheme 2 is reacted with zinc dust under organic solvent to synthesize the compound (h). In this step, it is preferable to use the zinc in the amount of 2 to 5 equivalents of the compound (h).

At the $2^{nd}$ step, the compound (h) obtained in step 1 is reacted with (AcO)$_2$O, PhCOCl, MsCl or TsCl to synthesize the compound (i). In the reaction, it is preferable to use (AcO)$_2$O, PhCOCl, MsCl or TsCl in the amount of 1 to 3 equivalents to the compound (h).

At the $3^{rd}$ step, the compound (i) obtained in step 2 is reacted with azine salt under the organic solvent such as methanol to produce the hydroxyamide compound (j), i.e., the general formula I compound wherein X is NHOH where the amine salt is preferably used in the amount of 2 to 3 equivalents to the compound (i), or with hydroxide metal salt such as LiOH under the organic solvent such as THF to produce the carboxylic acid compound k), i.e., the general formula I compound wherein X is OH where the metal salt is preferably used in the amount of 2 to 3 equivalents to the compound (i).

Scheme 5

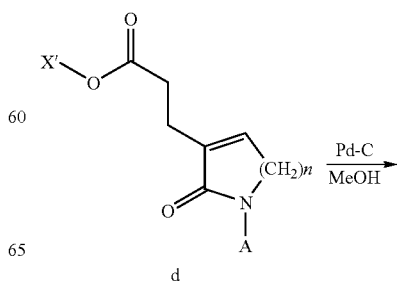

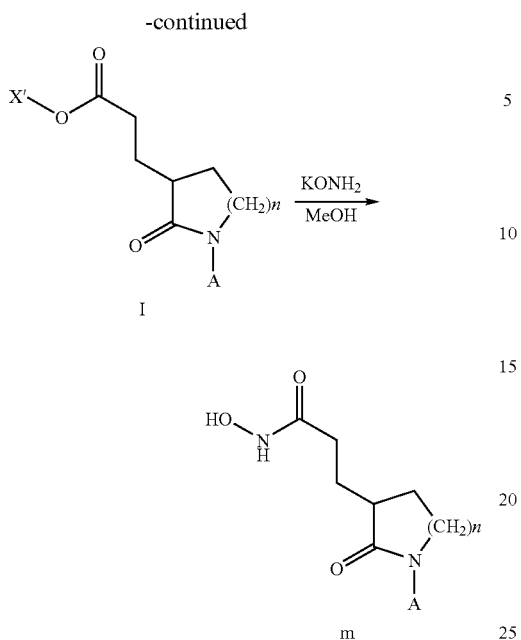

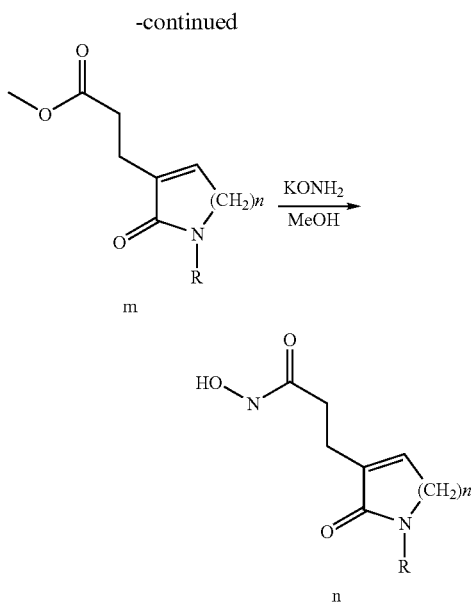

As shown in Scheme 5, the 1,2,5,6-dihydropyridine compound (d) is reduced to the piperidine compound (I) by reacting with palladium-carbon (Pd/C) under alcohol solvent in the amount of 0.1 to 0.2 equivalents of compound (d) and furthermore the piperidine compound (I) is reacted with $KONH_2$ in MeOH to synthesize the compound (m). In the reaction, it is preferable to use the amine salt in the amount of 2 to 3 equivalents to the compound (m) at the temperature ranging from 0° C. to RT.

As shown in Scheme 6, the benzyl compound (d) is reacted with trifluoroacetic acid (TFA) in the presence of the amount of 1 to 1.5 equivalent of the compound (d) to produce the compound (I). The compound (I) is further reacted with hexamethyldisilylazide sodium (NaHMDS) in THF solvent and subsequently reacted with R—X (R: ally, methyl etc, X: halogen atom) to produce the compound (m). In this reaction, it is preferable to use the NaHMDS in the amount of 1 to 1.5 equivalents to the compound (I).

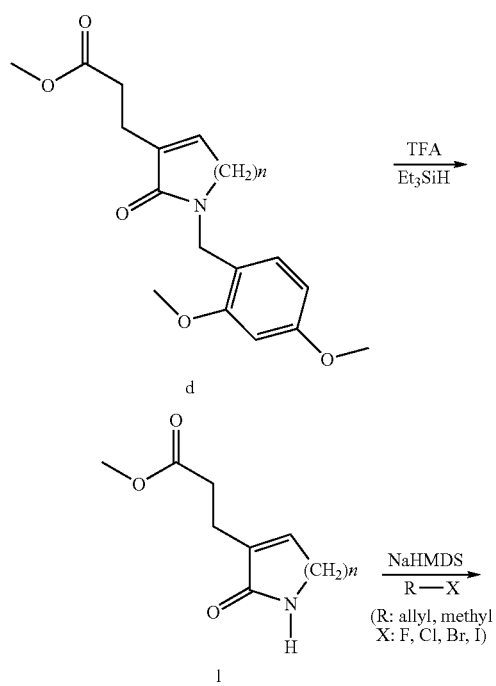

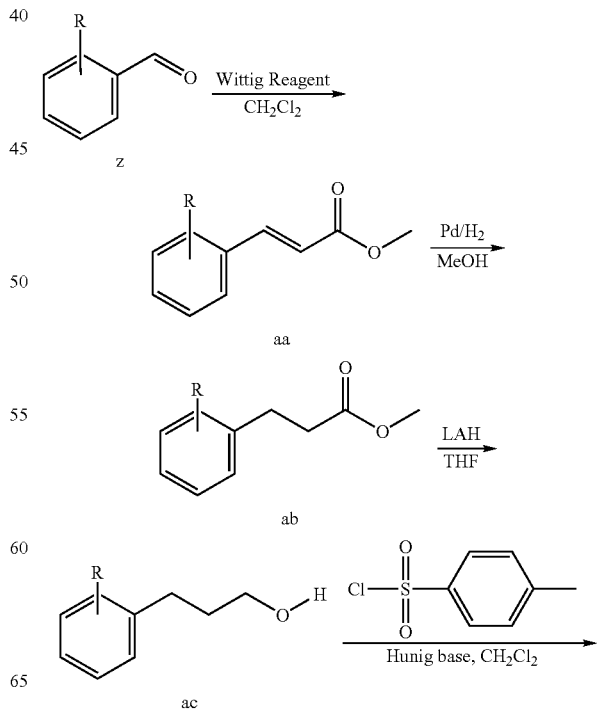

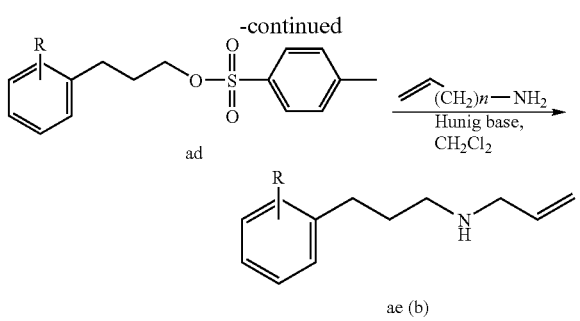

ae (b)

As shown in Scheme 7, the compound (b) as a starting material is prepared by following procedure: At the $1^{st}$ step, the compound (z) which can be procure by conventional market or chemical company is reacted with Wittig reagent under the organic solvent such as dichloromethane to synthesize to the compound (aa). In this step, it is preferable to use the Wittig reagent in the amount of 1.5 to 2 equivalents of the compound (z) at the temperature ranging from 60 to 70° C.

At the $2^{nd}$ step, the compound (aa) obtained in step 1 is reacted with Pd/C under $H_2$ atmosphere in the amount of 0.1 to 0.2 equivalents of the compound (aa) under ethyl alcohol solvent to synthesize the compound (ab).

At the $3^{rd}$ step, the compound (ab) obtained in step 2 is reacted with lithium aluminum hydride (LAH) under the organic solvent such as THF to produce the compound (ac) at 0° C.

At the $4^{th}$ step, the compound (ac) is subsequently reacted with p-toluenesulfonylchloride in the presence of diisopropylethylamine or 4-(dimethylamino)pyridine in the amount of 0.1 to 0.2 equivalents of the compound (aa) under ethyl alcohol solvent to synthesize the compound (ab).

At the $5^{th}$ step, both of allyl amine and Hunig base (diisopropylethylamine) are added to the compound (ad) dissolved in acetonitrile, mixed and stirred for six hours at 80° C. to produce the compound (ae), one of the compound (b).

The present invention also provides a pharmaceutical composition comprising an efficient amount of the compound represented by general formula (I) to (V) or the pharmaceutically acceptable salt thereof as an active ingredient in amount effective to treat or prevent inflammatory diseases together with pharmaceutically acceptable carriers or.

The compound of formula (I) to (V) according to the present invention can be provided as a pharmaceutical composition containing pharmaceutically acceptable carriers, adjuvants or diluents. For example, the compounds of the present invention can be dissolved in oils, propylene glycol or other solvents, which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The pharmaceutical compositions comprising the compound of the present invention can be treat and prevent the inflammatory disease comprising the pain or inflammation caused by rheumatic disease, for example, rheumatoid arthritis, spondyloarthopathies, gout, osteoarthritis, systemic lupus erythematosus and juvenile arthritis, and inflammatory syndrome for example, from myositis, gingivitis, synovitis, ankylosing spondylitis, burstitis, burns and scar, inflammatory Crohn's disease, Types I diabetes.

The compound of the present invention has potent anti-inflammatory activity, and the pharmaceutical composition of the present invention thus may be employed to treat or prevent the inflammatory disease comprising the pain or inflammation caused by rheumatic disease and inflammatory syndrome.

The present invention also provides a method of preventing or treating the inflammatory disease comprising the pain or inflammation caused by rheumatic disease and inflammatory syndrome which comprises administering compound selected from the group consisting of compounds of formula (I) to (V) or pharmaceutical acceptable salts thereof in need of such prevention or treatment a therapeutically effective amount of the salt or a pharmaceutically acceptable hydrate thereof as an anti-inflammatory agent.

The present invention also provides a use of the compounds as an active ingredient in medicines for treating or preventing the inflammatory disease comprising the pain or inflammation caused by rheumatic disease and inflammatory syndrome.

Hereinafter, the following formulation methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compounds varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001-100 mg/kg by weight/day of the inventive compounds of the present invention. The dose may be administered in single or divided into several times per day. In terms of composition, the compounds should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

The present invention is more specifically explained by the following examples. However, it should be understood that the present invention is not limited to these examples in any manner.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of 3-[1-(2,4-Dimethoxybenzyl)-2-oxo-2,5-dihydro-1H-pyrrol-3-yl]-N-hydroxypropionamide (1e)

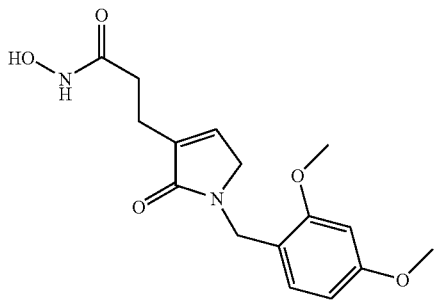

Step 1. Preparation of allyl-(2,4-dimethoxybenzyl)amine (1b)

0.32 ml of allylbromide (3.66 mmol) and 0.7 ml of diisopropyl ethylamine (3.99 mmol) were added to the reaction solution containing 500 mg of 2,4-dimethoxybenzylamine (3.33 mmol) dissolved in methylene chloride with stirring and the solution was left alone at room temperature. After the reaction mixture was neutralized with 10% NaOH solution, the mixture was extracted with chloroform, washed with saturated NaCl solution, dried over $MgSO_4$, filtered, and concentrated in vacuo. The resulting compound was purified with Silica gel column chromatography with a solvent mixture mixed with methanol and chloroform (1:9) as an eluant to give 276 mg of allyl-(2,4-dimethoxybenzyl)amine (1b) (yield: 40%).

$^1$H-NMR (300 MHz, $CDCl_3$) δ 7.12 (d, J=8.1 Hz, 1H), 6.44-6.39 (m, 2H), 5.99-5.86 (m, 1H), 5.21-5.09 (m, 2H), 3.79 (d, J=6.0 Hz, 6H), 3.74 (s, 2H), 3.23 (d, J=6.0 Hz, 2H)

Step 2. Preparation of 4-[allyl-(2,4-dimethoxy-benzyl)-carbamoyl]-pent-4-enoic acid methyl ester (1c)

253 mg of 2-methylene-pentane dionate-5-methyl ester (1.6 mmol), 331 mg of [3-(dimethylamino)propyl]-3-ethylcarbodiimide (1.73 mmol) and 48 mg of 4-(dimethylamino)pyridine (0.39 mmol) were added to 0.5 M of reaction solution dissolving the compound (1b) prepared by above step 1 in methylene chloride and the mixture was stirred for 10 hrs at room temperature. After the resulting mixture was washed with 5% HCl solution (10 ml), the mixture was extracted with ethylacetate, washed with saturated NaCl. And then the extracts were washed with saturated 10 ml of $NaHCO_3$ solution and NaCl solution to separate into an organic layer and water layer. The organic layer was dried over anhydrous $MgSO_4$, filtered and concentrated in vacuo. The resultant was purified by Silica gel column chromatography with a solvent mixture mixed with EtOAc and hexanes (1:2) as an eluant to give 324 mg of 4-[allyl-(2,4-dimethoxy-benzyl)-carbamoyl]-pent-4-enoic acid methyl ester (1c) (yield: 70%).

$^1$H-NMR (300 MHz, $CDCl_3$) δ 7.14 (s, 1H), 6.44 (d, 2H), 5.72 (s, 1H), 5.12 (s, 4H), 4.56-4.81 (m, 2H), 3.91-3.83 (m, 2H), 3.78 (d, J=5.3 Hz, 6), 3.65 (d, J=1.4 Hz, 3H), 2.63 (t, J=5.7 Hz, 2H), 2.54 (t, J=5.4 Hz, 2H)

Step 3. Preparation of 3-[1-(2,4-dimethoxybenzyl)-2-oxo-2,5-dihydro-1H-pyrrol-3-yl]-propionic acid methyl ester (1d)

324 mg of the compound (1c) (0.933 mmol) prepared by the above Step 2 was added to the catalyst solution containing 74 mg of ruthenium (0.09 mmol) dissolved in 93 ml of $CH_2Cl_2$. Then the mixture was stirred for 24 hrs at room temperature, filtered and concentrated in vacuo. The resultant was purified by Silica gel column chromatography with a solvent mixture mixed with EtOAc and hexanes (1:1) as an eluant to give 268 mg of 3-[1-(2,4-dimethoxybenzyl)-2-oxo-2,5-dihydro-1H-pyrrole-3-yl]-propionic acid methyl ester (1d) (yield: 90%).

$^1$H-NMR (300 MHz, $CDCl_3$) δ 7.11 (d, J=9.0 Hz, 1H), 6.61 (br t, 1H), 6.43 (s, 1H), 6.40 (d, J=2.7 Hz, 1H), 4.56 (s, 2H), 3.78 (d, J=5.4 Hz, 9H), 3.65 (s, 2H), 2.61 (s, 4H)

Step 4. Preparation of 3-[1-(2,4-dimethoxy-benzyl)-2-oxo-2,5-dihydro-1H-pyrrol-3-yl]-N-hydroxy-propionamide (1e)

100 mg of compound (d) prepared by the above Step 3 was dissolved in methanol solution (0.313 mmol) and then 1.7 M methanolic suspension solution containing $NH_2OK$ (0.27 ml, 0.47 mmol) was added thereto at 0° C. and the resulting mixture was stirred for 4 hrs at room temperature. The resulting mixture was neutralized with 0.02 ml of acetic acid, diluted with methanol/chloroform solution, filtered and concentrated in vacuo. The resulting compound was purified by Silica gel column chromatography with a solvent mixture mixed with methanol and chloroform (1:9) as an eluant to give 50 mg of 3-[1-(2,4-dimethoxy-benzyl)-2-oxo-2,5-dihydro-1H-pyrrol-3-yl]-N-hydroxy-propionamide (1e) (yield: 50%).

$^1$H-NMR (300 MHz, $CDCl_3$) δ 7.04 (d, J=8.1 Hz, 1H), 6.83 (s, 1H), 6.53-6.44 (m, 2H), 4.54 (s, 2H), 3.81 (t, J=2.0 Hz, 6H), 2.56 (t, J=7.2 Hz, 2H), 2.34 (t, J=7.4 Hz, 2H), 1.9 (s, 3H)

Example 2

Preparation of 3-(1-benzyl-2-oxo-2,5-dihydro-1H-pyrrol-3-yl)-N-hydroxy-propionamide (2e)

3-(1-benzyl-2-oxo-2,5-dihydro-1H-pyrrol-3-yl)-N-hydroxy-propionamide (2e) was prepared by the similar procedure described in above Example 1 (See Table 1a).

Example 3

Preparation of N-hydroxy-3-(2-oxo-1-phenethyl-2,5-dihydro-1H-pyrrol-3-yl)-propionamide (3e)

N-hydroxy-3-(2-oxo-1-phenethyl-2,5-dihydro-1H-pyrrol-3-yl)-propionamide (3e) was prepared by the similar procedure described in above Example 1 (See Table 1a).

Example 4

Preparation of N-hydroxy-3-[2-oxo-1-(3-phenyl-propyl)-2,5-dihydro-1H-pyrrol-3-yl]-propionamide (4e)

N-hydroxy-3-[2-oxo-1-(3-phenyl-propyl)-2,5-dihydro-1H-pyrrol-3-yl]-propionamide (4e) was prepared by the similar procedure described in above Example 1 (See Table 1a).

Example 5

Preparation of N-hydroxy-3-[2-oxo-1-(4-phenyl-butyl)-2,5-dihydro-1H-pyrrol-3-yl]-propionamide (5e)

N-hydroxy-3-[2-oxo-1-(4-phenyl-butyl)-2,5-dihydro-1H-pyrrol-3-yl]-propionamide (5e) was prepared by the similar procedure described in above Example 1 (See Table 1a).

Example 6

Preparation of N-hydroxy-3-[1-(2-methyl-benzyl)-2-oxo-2,5-dihydro-1H-pyrrol-3-yl]-propionamide (6e)

N-hydroxy-3-[1-(2-methyl-benzyl)-2-oxo-2,5-dihydro-1H-pyrrol-3-yl]-propionamide (6e) was prepared by the similar procedure described in above Example 1 (See Table 1a).

Example 7

Preparation of N-hydroxy-3-[1-(3-methyl-benzyl)-2-oxo-2,5-dihydro-1H-pyrrol-3-yl]-propionamide (7e)

N-hydroxy-3-[1-(3-methyl-benzyl)-2-oxo-2,5-dihydro-1H-pyrrol-3-yl]-propionamide (7e) was prepared by the similar procedure described in above Example 1 (See Table 1a).

Example 8

Preparation of N-hydroxy-3-[1-(4-methyl-benzyl)-2-oxo-2,5-dihydro-1H-pyrrol-3-yl]-propionamide (8e)

N-hydroxy-3-[1-(4-methyl-benzyl)-2-oxo-2,5-dihydro-1H-pyrrol-3-yl]-propionamide (8e) was prepared by the similar procedure described in above Example 1 (See Table 1a).

Example 9

Preparation of N-hydroxy-3-[1-(2-methoxy-benzyl)-2-oxo-2,5-dihydro-1H-pyrrol-3-yl]-propionamide (9e)

N-hydroxy-3-[1-(2-methoxy-benzyl)-2-oxo-2,5-dihydro-1H-pyrrol-3-yl]-propionamide (9e) was prepared by the similar procedure described in above Example 1 (See Table 1b).

Example 10

Preparation of N-hydroxy-3-[1-(3-methoxy-benzyl)-2-oxo-2,5-dihydro-1H-pyrrol-3-yl]-propionamide (10e)

N-hydroxy-3-[1-(3-methoxy-benzyl)-2-oxo-2,5-dihydro-1H-pyrrol-3-yl]-propionamide (10e) was prepared by the similar procedure described in above Example 1 (See Table 1b).

Example 11

Preparation of N-hydroxy-3-[1-(4-methoxy-benzyl)-2-oxo-2,5-dihydro-1H-pyrrol-3-yl]-propionamide (11e)

N-hydroxy-3-[1-(4-methoxy-benzyl)-2-oxo-2,5-dihydro-1H-pyrrol-3-yl]-propionamide (11e) was prepared by the similar procedure described in above Example 1 (See Table 1b).

Example 12

Preparation of 3-[1-(4-bromo-benzyl)-2-oxo-2,5-dihydro-1H-pyrrol-3-yl]-N-hydroxy-propionamide (12e)

3-[1-(4-bromo-benzyl)-2-oxo-2,5-dihydro-1H-pyrrol-3-yl]-N-hydroxy-propionamide (12e) was prepared by the similar procedure described in above Example 1 (See Table 1b).

Example 13

Preparation of 3-[1-(4-chloro-benzyl)-2-oxo-2,5-dihydro-1H-pyrrol-3-yl]-N-hydroxy-propionamide (13e)

3-[1-(4-chloro-benzyl)-2-oxo-2,5-dihydro-1H-pyrrol-3-yl]-N-hydroxy-propionamide (13e) was prepared by the similar procedure described in above Example 1 (See Table 1b).

Example 14

Preparation of 3-[1-(4-benzyloxy-benzyl)-2-oxo-2,5-dihydro-1H-pyrrol-3-yl]-N-hydroxy-propionamide (14e)

3-[1-(4-benzyloxy-benzyl)-2-oxo-2,5-dihydro-1H-pyrrol-3-yl]-N-hydroxy-propionamide (14e) was prepared by the similar procedure described in above Example 1 (See Table 1b).

Example 15

Preparation of N-hydroxy-3-[1-(4-nitro-benzyl)-2-oxo-2,5-dihydro-1H-pyrrol-3-yl]-propionamide (15e)

N-hydroxy-3-[1-(4-nitro-benzyl)-2-oxo-2,5-dihydro-1H-pyrrol-3-yl]-propionamide (15e) was prepared by the similar procedure described in above Example 1 (See Table 1b).

TABLE 1a
| Example | Chemical structure | NMR spectrum |
|---|---|---|
| 2 | 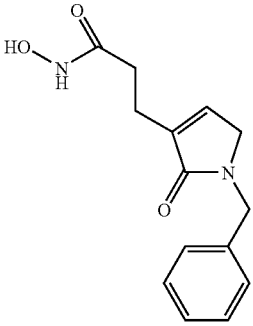 | 7.30-7.14 (m, 5H), 6.71 (d, J=18.3 Hz, 1H) 4.59 (d, J=7.8 Hz, 2H), 3.73 (s, 2H), 2.63 (s, 4H). |
| 3 | 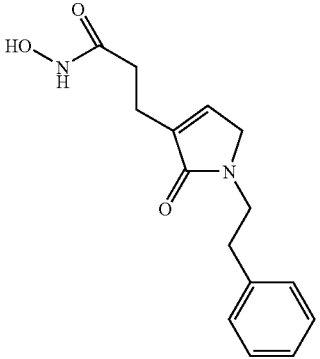 | 7.25-7.09 (m, 5H), 6.64 (s, 1H), 3.62 (t, J'=6.1 Hz, 4H), 2.81 (t, J=7.3 Hz, 2H), 2.52 (s, 2H), 2.30 (d, J=6.6 Hz, 2H) |
| 4 | 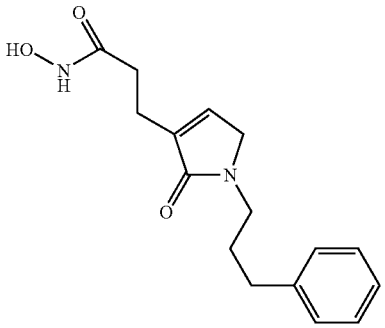 | 7.21 (d, J=7.5 Hz, 2H), 7.12 (d, J=6.6 Hz, 3H), 6.72 (s, 1H), 3.75 (s, 2H), 3.41 (s, 2H), 2.57 (d, J=6.3 Hz, 6H), 2.44 (s, 1H), 1.82 (s, 2H) |
| 5 | 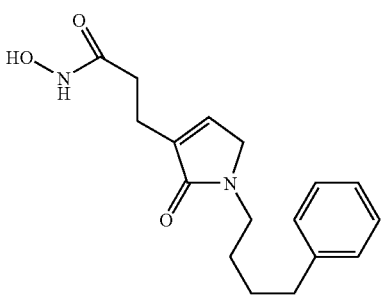 | 7.28-7.12 (m, 5H), 6.73 (s, 1H), 3.78 (d, J=9.0 Hz, 2H), 3.43 (s, 2H), 2.61 (s, 5H), 1.58 (s, 5H) |

TABLE 1a-continued

| Example | Chemical structure | NMR spectrum |
|---|---|---|
| 6 | 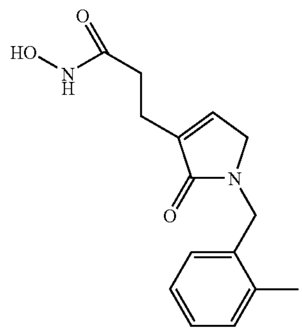 | 7.12 (s, 5H), 6.67 (s, 1H), 4.58 (d, J= 8.4 Hz, 2H), 3.64 (s, 2H), 2.61 (s, 4H), 2.34-2.22 (m, 3H) |
| 7 | 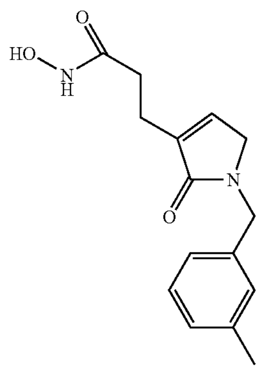 | 7.15 (d, J=6.9 Hz, 1H), 7.02-6.95 (m, 3H), 6.74 (s, 1H), 4.52 (d, J=8.4 Hz, 2H), 3.70, (s, 2H), 2.60 (s, 3H), 2.27 (d, J=4.8 Hz, 4H) |
| 8 | 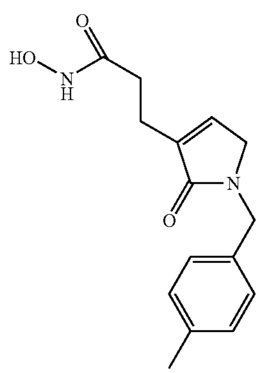 | 7.09-7.03 (m, 4H), 6.70 (d, J=18.3 Hz, 1H), 4.54 (d, J=7.2 Hz, 2H), 3.70 (s, 2H), 2.61 (s, 3H), 2.45 (s, 1H), 2.28 (d, J=13.5 Hz, 3H) |

TABLE 1b

| Example | Chemical structure | NMR spectrum or LC-MS data |
|---|---|---|
| 9 | 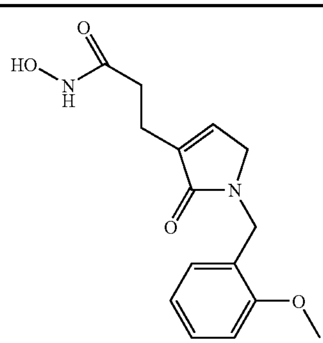 | 7.23-7.18 (m, 1H); 7.08 (d, J=3.5 Hz, 1H), 6.84 (dd, J=5.8 Hz, 2H), 6.72 (s, 1H), 4.59 (s, 2H), 3.78 (s, 3H), 3.75 (s, 2H), 2.60 (s, 2H), 2.44 (s, 2H) |

TABLE 1b-continued

| Example | Chemical structure | NMR spectrum or LC-MS data |
|---------|-------------------|----------------------------|
| 10 | 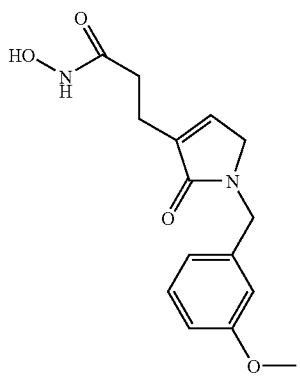 | 7.16 (t, J=4.8 Hz, 1H), 6.73 (t, J=5.4 Hz, 3H), 6.68 (s, 1H), 4.53 (d, J=10.5 Hz, 2H), 3.72 (t, J=5.2 Hz, 5H), 2.59 (s, 2H), 2.43 (s, 2H) |
| 11 | 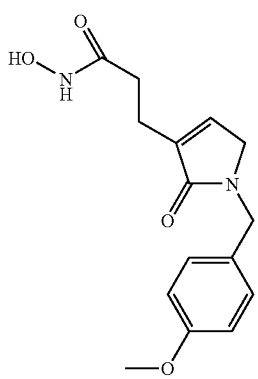 | 7.06-7.014 (m, 4H), 6.71 (s, 1H), 4.49 (s, 2H), 3.66 (s, 2H), 2.59 (s, 2H), 2.43 (s, 2H), 2.25 (s, 3H) |
| 12 | 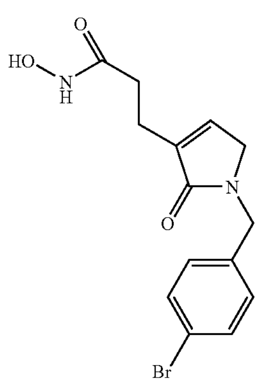 | 7.40 (d, J=7.8 Hz, 2H), 7.05 (d, J=8.4 Hz, 2H), 6.78 (s, 1H), 4.53 (s, 2H), 4.39 (s, 2H), 3.76 (s, 2H), 2.57 (t, J=5.7 Hz, 2H), 2.31 (t, J=7.2 Hz, 2H) |
| 13 | 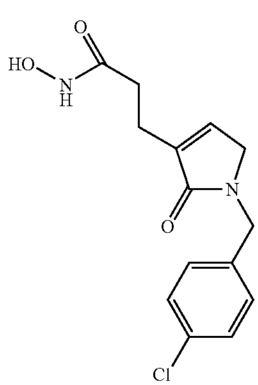 | 7.28-7.07 (m, 2H), 6.95 (t, J=8.2 Hz, 2H), 6.74 (s, 1H), 4.52 (s, 2H), 3.60 (s, 2H), 2.54 (s, 2H), 2.31 (d, J=7.2 Hz, 2H) |

TABLE 1b-continued

| Example | Chemical structure | NMR spectrum or LC-MS data |
|---|---|---|
| 14 | 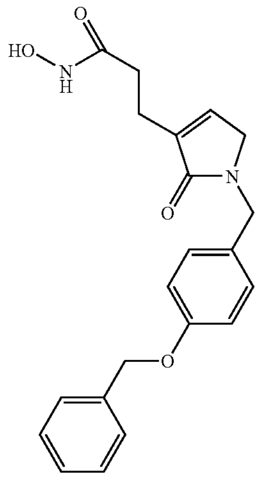 | 7.41-7.30 (m, 5H), 7.14 (d, J=Hz, 2H), 6.91 (d, J=8.4 Hz, 2H), 6.367 (s, 1H), 5.02 (s, 2H), 4.55 (s, 2H), 3.72 (s, 2H), 2.65 (2, 4H) |
| 15 | 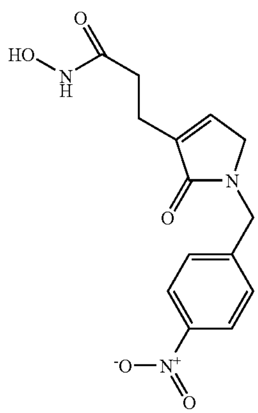 | RT: 3.82-4.54 (Mass; 306.1) |

Example 16

Preparation of 3-[1-(2,4-dimethoxy-benzyl)-2-oxo-2,5-dihydro-1H-pyrrol-3-yl]-propionic acid (16f)

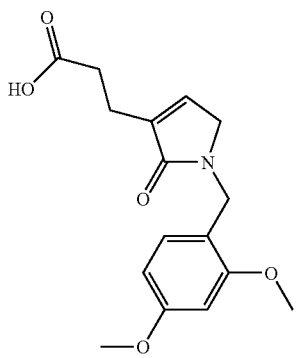

10.8 mg of LiOH.H$_2$O solution (0.25 mmol) was added to 0.86 ml of THF solution containing 55 mg of 3-[1-(2,4-dimethoxy benzyl)-2-oxo-2,5-dihydro-1H-pyrrol-3-yl]-propionic acid methyl ester (0.17 mmol) in a dropwise manner at 0° C. The reaction mixture was stirred for 2 hrs at 0° C. and 5% HCl was added to pH 1. Then the mixture was extracted three times with 10 ml of ethyl acetate, the organic layer was washed with 15 ml of saturated NaCl solution, dried over anhydrous MgSO$_4$, filtered and concentrated in vacuo. The resulting compound was purified with Silica gel column chromatography with a solvent mixture mixed with methanol and chloroform (1:9) as an eluant to give 41 mg of 3-[1-(2,4-dimethoxy-benzyl)-2-oxo-2,5-dihydro-1H-pyrrol-3-yl]-propionic acid (16f) (yield: 80%).

$^1$H-NMR (300 MHz, CDCl$_3$) δ 7.11 (d, J=9.0 Hz, 1H), 6.65 (br t, 1H), 6.41 (ab, J=6.5 Hz, 1.1 Hz, 2H), 4.57 (s, 2H), 3.81-3.76 (m, 8H), 2.63 (s, 4H)

Example 17

Preparation of 3-(1-benzyl-2-oxo-2,5-dihydro-1H-pyrrol-3-yl)-propionic acid (17f)

3-(1-benzyl-2-oxo-2,5-dihydro-1H-pyrrol-3-yl)-propionic acid (17f) was prepared by the similar procedure described in above Example 16 (See Table 2).

TABLE 2

| Example | Chemical structure | NMR spectrum data |
|---|---|---|
| 17 | (structure) | 7.33-7.19 (m, 5H), 6.69 (br t, 1H), 4.62 (s, 2H), 3.74 (s, 2H), 2.66 (s, 4H) |

Example 18

Preparation of N-{4-[3-(2-hydroxycarbamoyl-ethyl)-2-oxo-2,5-dihydro-pyrrole-1-yl-methyl]-phenyl}-benzamide (18j)

Step 1. Preparation of 3-[1-(4-amino-benzyl-2-oxo-2,5-dihydro-1H-pyrrol-3-yl]-propionic acid methyl ester (h)

90 mg of 3-[1-(4-nitro-benzyl)-2-oxo-2,5-dihydro-1H-pyrrol-3-yl]-propionic acid methyl ester (0.3 mmol) was dissolved in methanol solution at room temperature. And then 290 mg of Zn (4.44 mmol) and 0.02 ml of acetic acid (0.3 mmol) were added thereto and the mixture was stirred for 48 hrs at room temperature. The resulting compound was purified by Silica gel column chromatography with ethylacetate as an eluant to give 20 mg of 3-[1-(4-amino-benzyl)-2-oxo-2,5-dihydro-1H-pyrrol-3-yl]-propionic acid methyl ester (h) (yield: 25%).

$^1$H-NMR (300 MHz, CDCl$_3$) δ 7.01 (d, J=8.4 Hz, 2H), 6.62 (d, J=1.8 Hz, 2H), 6.60 (br t, 1H) 4.48 (s, 2H), 3.68 (d, J=1.2 Hz, 3H), 3.65 (s, 4H), 2.66-2.58 (m, 4H)

Step 2. Preparation of 3-[1-(4-benzoylamino-benzyl)-2-oxo-2,5-dihydro-1H-pyrrol-3-yl]-propionic acid methyl ester (i)

10 mg of 3-[1-(4-amino-benzyl)-2-oxo-2,5-dihydro-1H-pyrrol-3-yl]-propionic acid methyl ester (h) prepared by above Step 1 was dissolved in methylene chloride solution (0.04 mmol) at room temperature. And then 8.5 µl of benzoyl chloride (0.07 mmol) and 19.1 µl of diisopropylamine (0.11 mmol) were added thereto and the mixture was stirred for 2 hrs at 0° C. The reaction was quenched with methanol and the mixture was extracted three times with 10 ml of ethyl acetate. The organic layer was washed with saturated NaCl solution, dried over anhydrous MgSO$_4$, filtered and concentrated in vacuo. The resulting compound was purified with Silica gel column chromatography with a solvent mixture mixed with ethyl acetate and hexane (1:2) as an eluant to give 12 mg of 3-[1-(4-benzoylamino-benzyl)-2-oxo-2,5-dihydro-1H-pyrrol-3-yl]-propionic acid methyl ester (i) (yield: 87%).

$^1$H-NMR (300 MHz, CDCl$_3$) δ 7.88-7.83 (m, 3H), 7.62-7.47 (m, 6H), 6.68 (br t, 1H), 4.62 (S, 2H), 3.75 (d, 2H), 3.68 (s, 3H), 2.67-2.64 (m, 4H)

Step 3. Preparation of N-{4-[3-(2-hydroxycarbamoyl-ethyl)-2-oxo-2,5-dihydro-pyrrole-1-yl-methyl]-phenyl}-benzamide (j)

7 mg of compound (i) prepared by the above Step 2 was dissolved in methanol solution (0.02 mmol) and then 1.7 M methanolic suspension solution containing NH$_2$OK (0.4 ml, 0.68 mmol) was added thereto at 0° C. and the resulting mixture was stirred for 8 hrs at room temperature. The resulting mixture was neutralized with 0.01 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 3.2 mg of N-{4-[3-(2-hydroxycarbamoyl-ethyl)-2-oxo-2,5-dihydro-pyrrole-1-yl-methyl]-phenyl}-benzamide (j) (yield: 46%).

$^1$H-NMR (300 MHz, CDCl$_3$) δ 7.86 (d, J=6.6 Hz, 2H), 7.62 (d, J=8.7 Hz, 2H), 7.53-7.39 (m, 4H), 7.17 (d, J=8.4 Hz, 2H), 6.77 (br t, 1H), 4.57 (s, 2H), 3.77 (s, 2H), 2.58 (t, J=7.3 Hz, 2H), 2.31 (t, J=7.2 Hz, 2H)

Example 19

Preparation of N-hydroxy-3-{2-oxo-1-[4-(toluene-4-sulfonylamino)-benzyl]-2,5-dihydro-1H-pyrrol-3-yl}-propionamide (19j)

N-hydroxy-3-{2-oxo-1-[4-(toluene-4-sulfonylamino)-benzyl]-2,5-dihydro-1H-pyrrol-3-yl}-propionamide (19j) was prepared by the similar procedure described in above Example 18 (See Table 3).

TABLE 3

| Example | Chemical structure | NMR spectrum data |
|---|---|---|
| 19 | (structure) | 7.61 (t, J=7.0 Hz, 3H), 7.05-6.89 (m, 6H), 4.54 (s, 3H), 3.74 (s, 3H), 3.39 (s, 3H), 2.37 (s, 3H), RT: 3.87-4.34 (Mass: 430.0) |

Example 20

Preparation of 2-(1-benzyl-2-oxo-2,5-dihydro-1H-pyrrol-3-yl)-N-hydroxy-acetamide (20q)

Step 1. Preparation of 3-(allyl-benzyl-carbamoyl)-but-3-enoic acid methyl ester (o)

587 mg of 2-methylene-succinate 4-methyl ester (4.07 mmol), 781 mg of 1-[3-(dimethylamino)propyl]-3-ethylcarbodiimide (4.07 mmol) and 75 mg of 4-(dimethylamino) pyridine (0.61 mmol) were added to the reaction solution containing 300 mg of allylbenzylamine (2.04 mmol) dissolved in methylene chloride solution (0.5 M) with stirring for 10 hrs at room temperature. After the resulting mixture was washed with 5% HCl solution (10 ml), the mixture was diluted with ethyl acetate, washed with 10 ml of solution mixture mixed with saturated $NaHCO_3$ solution and saturated NaCl solution to separate into an organic layer and water layer. The organic layer was dried over anhydrous $MgSO_4$, filtered and concentrated in vacuo. The resultant was purified by Silica gel column chromatography with a solvent mixture mixed with EtOAc and hexanes (1:1) as an eluant to give 272 mg of 3-(allyl-benzyl-carbamoyl)-but-3-enoic acid methyl ester (o) (yield: 49%).

$^1$H-NMR (300 MHz, $CDCl_3$) δ 7.30-7.22 (m, 5H), 5.84-5.71 (m, 1H), 5.37-5.15 (m, 4H), 4.75-4.65 (m, 2H), 4.02 (s, 2H), 3.63 (s, 3H), 3.48 (s, 2H)

Step 2. Preparation of (1-benzyl-2-oxo-2,5-dihydro-1H-pyrrol-3-yl)-acetic acid methyl ester (p)

234 mg of 3-(allyl-benzyl-carbamoyl)-but-3-enoic acid methyl ester (o) (0.1 mmol) prepared by the above Step 1 was added to the catalyst solution containing 36 mg of Grubb's (I) catalyst (0.04 mmol) such as ruthenium dissolved in $CH_2Cl_2$ under Ar atmosphere. Then the mixture was stirred for 24 hrs at room temperature, filtered and concentrated in vacuo. The resultant was purified by Silica gel column chromatography with a solvent mixture mixed with EtOAc and hexanes (1:2) as an eluant to give 180 mg of (1-benzyl-2-oxo-2,5-dihydro-1H-pyrrol-3-yl)-acetic acid methyl ester (p) (yield: 85%).

$^1$H-NMR (300 MHz, $CDCl_3$) δ 7.33-7.18 (m, 5H), 6.94 (t, J=1.5 Hz, 1H), 4.61 (s, 2H), 3.79 (d, J=0.7 Hz, 2H), 3.70 (s, 3H), 3.37 (d, J=1.5 Hz, 2H)

Step 3. Preparation of 2-(1-benzyl-2-oxo-2,5-dihydro-1H-pyrrol-3-yl)-N-hydroxy-acetamide (q)

24 mg of (1-benzyl-2-oxo-2,5-dihydro-1H-pyrrol-3-yl)-acetic acid methyl ester (p) prepared by the above Step 2 was dissolved in methanol solution (0.1 mmol) and then 1.7 M methanolic suspension solution containing $NH_2OK$ (0.4 ml, 0.68 mmol) was added thereto at 0° C. and the resulting mixture was stirred for 4 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 12 mg of 2-(1-benzyl-2-oxo-2,5-dihydro-1H-pyrrol-3-yl)-N-hydroxy-acetamide (q) (yield: 48%).

$^1$H-NMR (300 MHz, $CDCl_3$) δ 7.35-7.21 (m, 5H), 7.05 (br t, 1H), 4.63 (s, 2H), 3.90 (s, 2H), 3.30 (t, J=1.5 Hz, 1H), 3.13 (s, 2H)

Example 21

Preparation of 2-[1-(2,4-dimethoxy-benzyl)-2-oxo-2,5-dihydro-1H-pyrrol-3-yl]-N-hydroxy-acetamide (21q)

2-[1-(2,4-dimethoxy-benzyl)-2-oxo-2,5-dihydro-1H-pyrrol-3-yl]-N-hydroxy-acetamide (21q) was prepared by the similar procedure described in above Example 20 (See Table 4).

Example 22

Preparation of N-hydroxy-2-(2-oxo-1-phenethyl-2,5-dihydro-1H-pyrrol-3-yl)-acetamide (22q)

N-hydroxy-2-(2-oxo-1-phenethyl-2,5-dihydro-1H-pyrrol-3-yl)-acetamide (22q) was prepared by the similar procedure described in above Example 20 (See Table 4).

Example 23

Preparation of N-hydroxy-2-[2-oxo-1-(4-phenyl-butyl)-2,5-dihydro-1H-pyrrol-3-yl]-acetamide (23q)

N-hydroxy-2-[2-oxo-1-(4-phenyl-butyl)-2,5-dihydro-1H-pyrrol-3-yl]-acetamide (23q) was prepared by the similar procedure described in above Example 20 (See Table 4).

Example 24

Preparation of 2-[1-(4-benzyloxy-benzyl)-2-oxo-2,5-dihydro-1H-pyrrol-3-yl]-N-hydroxy-acetamide (24q)

2-[1-(4-benzyloxy-benzyl)-2-oxo-2,5-dihydro-1H-pyrrol-3-yl]-N-hydroxy-acetamide (24q) was prepared by the similar procedure described in above Example 20 (See Table 4).

TABLE 4

| Example | Chemical structure | NMR spectrum data |
|---|---|---|
| 21 | 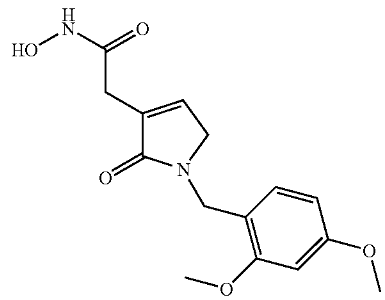 | 7.12 (d, J=8.4 Hz, 2H), 6.90(d, J=20.7 Hz, 1H), 6.43 (d, J=6.0 Hz), 4.57 (d, J= 2.7 Hz, 2H), 3.86 (d, J=15.9 Hz, 2H), (d, J=3.0 Hz, 6H) |

TABLE 4-continued

| Example | Chemical structure | NMR spectrum data |
|---|---|---|
| 22 | 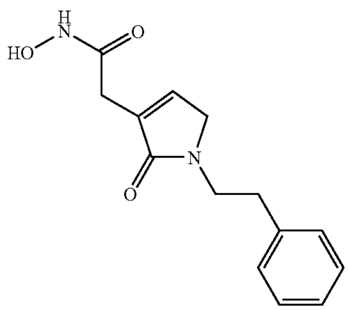 | 7.29-7.14 (m, 5H), 6.90 (br t, 1H), 3.75-3.65 (m, 4H), 3.23 (s, 1H), 2.92-2.84 (m, 2H) |
| 23 | 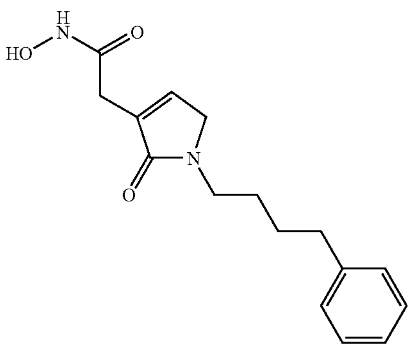 | 7.21 (t, J=7.4 Hz, 2H), 7.11 (d, J=7.8 Hz, 3H), 6.76 (br t, 1H), 5.22 (s, 1H), 3.30 (t, J=3.3 Hz, 1H), 2.58 (t, J=7.0 Hz, 2H), 2.04 (s, 3H), 1.82 (s, 3H), 1.57 (s, 4H) |
| 24 | 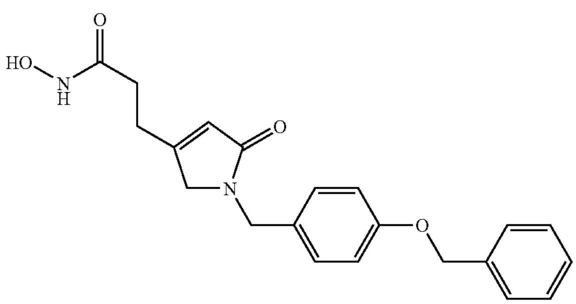 | 7.39-7.31 (m, 5H), 7.13 (d, J=8.4 Hz, 2H), 6.92 (d, J=8.7 Hz, 3H), 5.03 (s, 2H), 4.56 (s, 2H), 3.82 (d, J=13.8 Hz, 2H), 3.53 (s, 1H), 3.31 (s, 1H) |

Example 25

Preparation of 2-(1-benzyl-2-oxo-pyrrolidin-3-yl)-N-hydroxy-acetamide (25s)

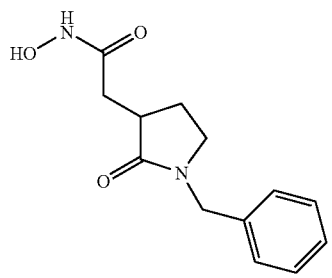

Step 1. Preparation of (2-oxo-1-phenethyl-pyrrolidin-3-yl)-acetic acid methyl ester (25r)

30 mg of (1-benzyl-2-oxo-2,5-dihydro-1H-pyrrol-3-yl)-acetic acid methyl ester was dissolved in methanol solution (0.12 mmol) under nitrogen atmosphere. Then 2.6 mg of Pd—C (0.02 mmol) was added thereto, and hydrogenated under a hydrogen balloon for 1 to 2 hrs at room temperature. The reaction mixture was filtered and concentrated in vacuo. The resulting compound was purified with Silica gel column chromatography with a solvent mixture mixed with BtOAc and hexane (1:1) as an eluant to give (2-oxo-1-phenethyl-pyrrolidin-3-yl)-acetic acid methyl ester (25r) (yield: 95%).

$^1$H-NMR (300 MHz, CDCl$_3$) δ 7.34-7.19 (m, 5H), 4.44 (ab, J=19.8 Hz, 7.4 Hz, 2H), 3.67 (s, 3H), 3.21-3.16 (m, 2H), 2.9 6 (m, 2H), 2.43 (dd, J=8.7 Hz, 7.9 Hz, 1H), 2.34-2.23 (m, 1H), 1.76-1.65 (m, 1H)

Step 2. Preparation of 2-(1-benzyl-2-oxo-pyrrolidin-3-yl)-N-hydroxy-acetamide (25s)

12 mg of (2-oxo-1-phenethyl-pyrrolidin-3-yl)-acetic acid methyl ester (25r) prepared by the above Step 1 was dissolved in methanol solution (0.04 mmol) and then 1.7 M methanolic suspension solution containing NH$_2$OK (0.07 ml, 0.12 mmol) was added thereto at 0° C. and the resulting mixture was stirred for 4 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 1.6 mg of 2-(1-benzyl-2-oxo-pyrrolidin-3-yl)-N-hydroxy-acetamide (25s) (yield: 8%).

$^1$H-NMR (300 MHz, CDCl$_3$) δ 7.34-7.19 (m, 5H), 4.46 (d, J=8.1 Hz, 2H), 3.35-3.20 (m, 2H), 3.01-2.71 (m, 2H), 2.66-2.44 (m, 2H), 2.35-2.22 (m, 2H), 1.81-1.58 (m, 2H)

Example 26

Preparation of 2-[1-(2,4-dimethoxy-benzyl)-2-oxo-pyrrolidin-3-yl]-N-hydroxy-acetamide (26s)

2-[1-(2,4-dimethoxy-benzyl)-2-oxo-pyrrolidin-3-yl]-N-hydroxy-acetamide (26s) was prepared by the similar procedure described in above Example 25 (See Table 5).

Example 27

Preparation of N-hydroxy-2-(2-oxo-1-phenethyl-pyrrolidin-3-yl)-acetamide (27s)

N-hydroxy-2-(2-oxo-1-phenethyl-pyrrolidin-3-yl)-acetamide (27s) was prepared by the similar procedure described in above Example 25 (See Table 5).

Example 28

Preparation of 3-{1-[2-(2-fluoro-phenyl)-ethyl]-2-oxo-2,5-dihydro-1H-pyrrol-3-yl}-N-hydroxy-propionamide (28y)

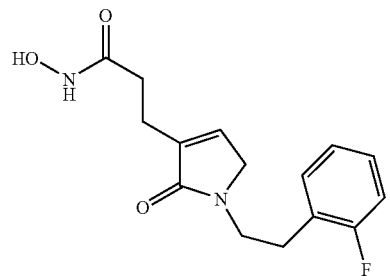

Step 1. Preparation of toluen-4-sulfonate-2-(2-fluoro-phenyl)-ethyl ester (u)

1.02 g of p-toluenesulfonyl chloride (5.35 mM), 1.24 ml of diisopropyl ethylamine (7.13 mmol) and 86 mg of 4-(dimethylamino)pyridine (0.71 mmol) were added to the reaction solution (3.57 mmol) containing 500 mg of 2-(2-fluoro-phenyl)-ethanol (3.57 mmol) dissolved in methylene chloride solution with stirring for 6 hrs at 0° C. under Ar atmosphere, and then the reaction mixture was stirred for 12 hrs at room temperature. The resulting mixture was neutralized with ammonium chloride, extracted with ethyl acetate and washed with saturated NaCl solution to separate into an organic layer and water layer. The organic layer was dried over anhydrous

TABLE 5

| Example | Chemical structure | NMR spectrum data |
|---|---|---|
| 26 | 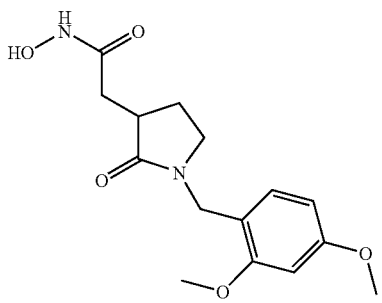 | 7.10 (t, J=9.3 Hz, 1H), 6.44 (t, J=2.6 Hz, 2H), 4.43 (dd, J=14.3 Hz, 14.8 Hz, 2H), 3.78 (s, 6H), 3.31-3.21 (m, 2H), 2.88-2.68 (m, 1H), 2.56-2.49 (m, 1H), 2.26-2.22 (m, 1H), 1.71-1.60 (m, 1H) |
| 27 | 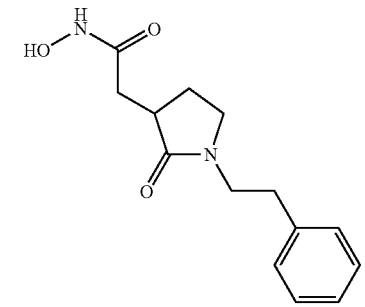 | 7.30-7.15 (m, 5H), 3.50(t, J=7.1 Hz, 2H), 3.25-3.11 (m, 2H), 2.86-2.66 (m, 3H), 2.57-2.44 (m, 1H), 2.32-2.21 (m, 2H), 1.77-1.62 (m, 1H) |

MgSO$_4$, filtered and concentrated in vacuo. The resultant was purified by Silica gel column chromatography with a solvent mixture mixed with methanol and chloroform (1:7) as an eluant to give 740 mg of toluen-4-sulfonate-2-(2-fluoro-phenyl)-ethyl ester (u) (yield: 70%).

Step 2. Preparation of allyl-[2-(2-fluoro-phenyl)-ethyl]-amine (v)

0.89 ml of allylamine (11.9 mmol) and 0.311 ml of diisopropyl ethylamine (1.78 mM) were added to the reaction solution (1.2 mmol) containing 350 mg of toluen-4-sulfonate-2-(2-fluoro-phenyl)-ethyl ester (u) prepared by above Step 1 dissolved in acetonitrile solution with stirring for 6 hrs at 80° C. After the reaction mixture was neutralized with 10% NaOH solution, the mixture was extracted with chloroform, washed with saturated NaCl solution, dried over MgSO$_4$, filtered, and concentrated in vacuo. The resultant was purified by Silica gel column chromatography with a solvent mixture mixed with methanol and chloroform (1:9) as an eluant to give 141 mg of allyl-[2-(2-fluoro-phenyl)-ethyl]-amine (v) (yield: 66%).

Step 3. Preparation of 4-{allyl-[2-(3-fluoro-phenyl)-ethyl]-carbamoyl}-pent-4-enoic acid methyl ester (w)

106 mg of 2-methylene-pentane dionate-5-methyl ester (0.67 mmol), 139 mg of 1-[3-(dimethylamino)propyl]-3-ethylcarbodiimide (0.73 mmol) and 20 mg of 4-(dimethylamino)pyridine (0.17 mmol) were added to reaction solution (0.56 mmol) dissolving 100 mg of allyl-[2-(2-fluoro-phenyl)-ethyl]-amine (v) prepared by above step 2 in methylene chloride and the mixture was stirred for 10 hrs at room temperature. After the resulting mixture was washed with 5% HCl solution (10 ml), the mixture was extracted with ethylacetate, washed with saturated NaCl. And then the extracts were washed with 10 ml of saturated NaHCO$_3$ solution and NaCl solution to separate into an organic layer and water layer. The organic layer was dried over anhydrous MgSO$_4$, filtered and concentrated in vacuo. The resultant was purified by Silica gel column chromatography with a solvent mixture mixed with EtOAc and hexanes (1:2) as an eluant to give 128 mg of 4-{allyl-[2-(3-fluoro-phenyl)-ethyl]-carbamoyl}-pent-4-enoic acid methyl ester (w) (yield: 72%).

$^1$H-NMR (300 MHz, CDCl$_3$) δ 7.19-7.09 (m, 1H), 7.04-6.94 (m, 3H), 5.84-5.57 (m, 1H), 5.13 (t, J=10.7 Hz, 4H), 5.06-4.94 (m, 2H), 3.79 (s, 2H), 3.62 (s, 4H), 3.53 (d, J=5.4 Hz, 3H), 2.89 (d, J=6.0 Hz, 3H)

Step 4. Preparation of 3-{1-[2-(2-fluoro-phenyl)-ethyl]-2-oxo-2,5-dihydro-1H-pyrrol-3-yl}-propionic acid methyl ester (x)

100 mg of 4-{allyl-[2-(3-fluoro-phenyl)-ethyl]-carbamoyl}-pent-4-enoic acid methyl ester (w) (0.31 mmol) prepared by the above Step 3 was added to the catalyst solution containing 27 mg of ruthenium catalyst (0.03 mmol) dissolved in 31.3 ml of CH$_2$Cl$_2$ under Ar atmosphere. Then the mixture was stirred for 24 hrs at room temperature, filtered and concentrated in vacuo. The resultant was purified by Silica gel column chromatography with a solvent mixture mixed with EtOAc and hexanes (1:1) as an eluant to give 69 mg of 3-{1-[2-(2-fluoro-phenyl)-ethyl]-2-oxo-2,5-dihydro-1H-pyrrol-3-yl}-propionic acid methyl ester (x) (yield: 75%).

$^1$H-NMR (300 MHz, CDCl$_3$) δ 7.16-7.12 (m, 2H), 7.03-6.93 (m, 2H), 6.59 (br t, 1H), 3.67-3.65 (m, 4H), 3.62 (s, 3H), 2.89 (t, J=7.3 Hz, 2H), 2.56 (s, 4H)

Step 5. Preparation of 3-{1-[2-(2-fluoro-phenyl)-ethyl]-2-oxo-2,5-dihydro-1H-pyrrol-3-yl}-N-hydroxy-propionamide (28y)

38 mg of 3-{1-[2-(2-fluoro-phenyl)-ethyl]-2-oxo-2,5-dihydro-1H-pyrrol-3-yl}-propionic acid methyl ester (x) prepared by the above Step 4 was dissolved in methanol solution (0.13 mmol) and then 1.7 M methanolic suspension solution containing NH$_2$OK (0.38 ml, 0.65 mmol) was added thereto at 0° C. and the resulting mixture was stirred for 8 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 25 mg of 3-{1-[2-(2-fluoro-phenyl)-ethyl]-2-oxo-2,5-dihydro-1H-pyrrol-3-yl}-N-hydroxy-propionamide (28y) (yield: 65%).

$^1$H-NMR (300 MHz, CDCl$_3$) δ 7.19-7.08 (m, 2H), 7.02-6.92 (m, 2H), 6.69 (br t, 1H), 3.69 (s, 2H), 3.63 (t, J=7.0 Hz, 2H), 2.87 (t, J=7.0 Hz, 2H), 2.51 (t, J=7.0 Hz, 2H), 2.25 (t, J=7.3 Hz, 2H)

Example 29

Preparation of 3-{1-[2-(3-fluoro-phenyl)-ethyl]-2-oxo-2,5-dihydro-1H-pyrrol-3-yl}-N-hydroxy-propionamide (29y)

3-{1-[2-(3-fluoro-phenyl)-ethyl]-2-oxo-2,5-dihydro-1H-pyrrol-3-yl}-N-hydroxy-propionamide (29y) was prepared by the similar procedure described in above Example 28 (See Table 6a).

Example 30

Preparation of 3-{1-[2-(4-fluoro-phenyl)-ethyl]-2-oxo-2,5-dihydro-1H-pyrrol-3-yl}-N-hydroxy-propionamide (30y)

3-{1-[2-(4-fluoro-phenyl)-ethyl]-2-oxo-2,5-dihydro-1H-pyrrol-3-yl}-N-hydroxy-propionamide (30y) was prepared by the similar procedure described in above Example 28 (See Table 6a).

Example 31

Preparation of N-hydroxy-3-{1-[2-(2-nitro-phenyl)-ethyl]-2-oxo-2,5-dihydro-1H-pyrrol-3-yl}-propionamide (31y)

N-hydroxy-3-{1-[2-(2-nitro-phenyl)-ethyl]-2-oxo-2,5-dihydro-1H-pyrrol-3-yl}-propionamide (31y) was prepared by the similar procedure described in above Example 28 (See Table 6a).

Example 32

Preparation of N-hydroxy-3-{1-[2-(3-nitro-phenyl)-ethyl]-2-oxo-2,5-dihydro-1H-pyrrol-3-yl}-propionamide (32y)

N-hydroxy-3-{1-[2-(3-nitro-phenyl)-ethyl]-2-oxo-2,5-dihydro-1H-pyrrol-3-yl}-propionamide (32y) was prepared by the similar procedure described in above Example 28 (See Table 6a).

Example 33

Preparation of N-hydroxy-3-{1-[2-(4-nitro-phenyl)-ethyl]-2-oxo-2,5-dihydro-1H-pyrrol-3-yl}-propionamide (33y)

N-hydroxy-3-{1-[2-(4-nitro-phenyl)-ethyl]-2-oxo-2,5-dihydro-1H-pyrrol-3-yl}-propionamide (33y) was prepared by the similar procedure described in above Example 28 (See Table 6a).

Example 34

Preparation of 3-{1-[2-(2-bromo-phenyl)-ethyl]-2-oxo-2,5-dihydro-1H-pyrrol-3-yl}-N-hydroxy-propionamide (34y)

3-{1-[2-(2-bromo-phenyl)-ethyl]-2-oxo-2,5-dihydro-1H-pyrrol-3-yl}-N-hydroxy-propionamide (34y) was prepared by the similar procedure described in above Example 28 (See Table 6a).

Example 35

Preparation of 3-{1-[2-(4-bromo-phenyl)-ethyl]-2-oxo-2,5-dihydro-1H-pyrrol-3-yl}-N-hydroxy-propionamide (35y)

3-{1-[2-(4-bromo-phenyl)-ethyl]-2-oxo-2,5-dihydro-1H-pyrrol-3-yl}-N-hydroxy-propionamide (35y) was prepared by the similar procedure described in above Example 28 (See Table 6b).

Example 36

Preparation of N-hydroxy-3-{1-[2-(2-methoxy-phenyl)-ethyl]-2-oxo-2,5-dihydro-1H-pyrrol-3-yl}-propionamide (36y)

N-hydroxy-3-{1-[2-(2-methoxy-phenyl)-ethyl]-2-oxo-2,5-dihydro-1H-pyrrol-3-yl}-propionamide (36y) was prepared by the similar procedure described in above Example 28 (See Table 6b).

Example 37

Preparation of N-hydroxy-3-{1-[2-(3-methoxy-phenyl)-ethyl]-2-oxo-2,5-dihydro-1H-pyrrol-3-yl}-propionamide (37y)

N-hydroxy-3-{1-[2-(3-methoxy-phenyl)-ethyl]-2-oxo-2,5-dihydro-1H-pyrrol-3-yl}-propionamide (37y) was prepared by the similar procedure described in above Example 28 (See Table 6b).

Example 38

Preparation of N-hydroxy-3-{1-[2-(4-methoxy-phenyl)ethyl]-2-oxo-2,5-dihydro-1H-pyrrol-3-yl}-propionamide (38y)

N-hydroxy-3-{1-[2-(4-methoxy-phenyl)-ethyl]-2-oxo-2,5-dihydro-1H-pyrrol-3-yl}-propionamide (38y) was prepared by the similar procedure described in above Example 28 (See Table 6b).

Example 39

Preparation of N-hydroxy-3-[2-oxo-1-(2-p-tolyl-ethyl)-2,5-dihydro-1H-pyrrol-3-yl]-propionamide (39y)

N-hydroxy-3-[2-oxo-1-(2-p-tolyl-ethyl)-2,5-dihydro-1H-pyrrol-3-yl]-propionamide (39y) was prepared by the similar procedure described in above Example 28 (See Table 6b).

TABLE 6a

| Example | Chemical structure | NMR spectrum data |
|---|---|---|
| 29 | 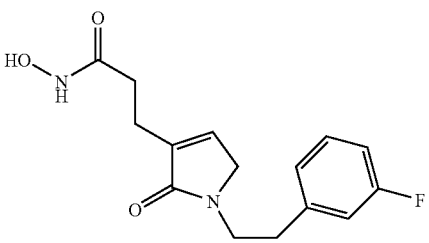 | 7.25-7.18 (m, 1H), 6.90 (ab, J=18.3 Hz, 4.3 Hz, 3H), 6.71 (br t, 1H), 3.65 (t, J= 6.9 Hz, 4H), 2.85 (t, J=6.9 Hz, 2H), 2.61 (s, 2H), 2.45 (s, 2H) |
| 30 | 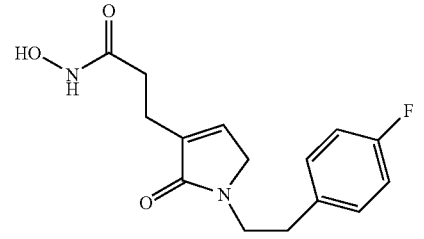 | 7.11-6.94 (m, 4H), 6.70 (br t, 1H), 3.65 (s, 4H), 2.82 (s, 3H), 2.68-2.60 (m, 3H) |

TABLE 6a-continued

| Example | Chemical structure | NMR spectrum data |
|---|---|---|
| 31 | 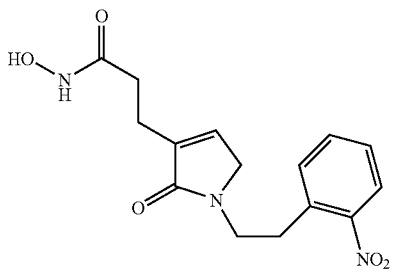 | 7.93 (d, J=7.8 Hz, 1H), 7.56 (t, J=6.7 Hz, 1H), 7.44-7.36 (m, 2H), 6.81 (br t, 1H), 3.85 (s, 2H), 3.76 (t, J=7.3 Hz, 2H), 3.15 (t, J=7.1 Hz, 2H), 2.54 (t, J=7.1 Hz, 2H), 2.30 (t, J=7.4 Hz, 2H) |
| 32 | 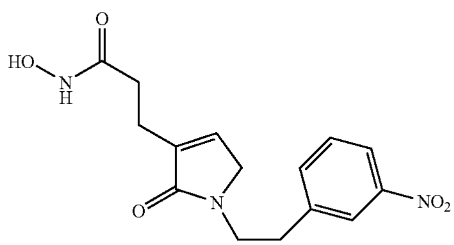 | 8.00 (d, J=7.2 Hz, 2H), 7.49-7.38 (m, 2H), 6.70 (br t, 1H), 3.72 (s, 2H), 3.64 (t, J=7.2 Hz, 2H), 2.93 (t, J=7.4 Hz, 2H), 2.48 (t, J=7.3 Hz, 2H), 2.22 (t, J=7.7 Hz, 2H) |
| 33 | 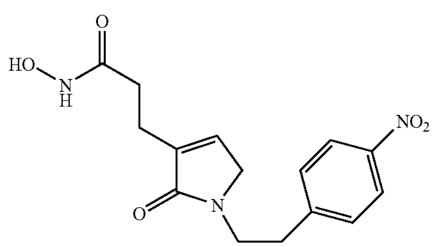 | 8.09 (d, J=8.4 Hz, 2H), 7.36 (d, J=9.6 Hz, 2H), 6.74 (br t, 1H), 3.76 (d, J=1.2 Hz, 1H), 3.69 (t, J=7.1 Hz, 1H), 3.29 (d, J=7.8 Hz, 1H), 3.26 (dd, J=1.2 Hz, 1.5 Hz, 1H), 2.97 (t, J=7.3 Hz, 2H), 2.49 (t, J=6.9 Hz, 2H), 2.25 (t, J=7.6 Hz, 2H) |
| 34 | 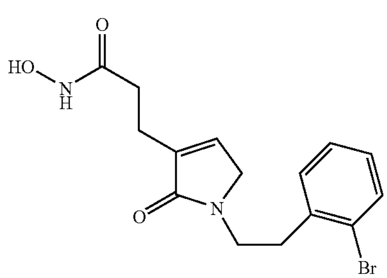 | 7.48 (d, J=8.1 Hz, 2H), 7.21-7.13 (m, 2H), 7.07-7.02 (m, 1H), 6.71 (br t, 1H), 3.70-3.62 (m, 4H), 2.98 (t, J=7.3 Hz, 2H), 2.52 (t, J=7.3 Hz, 2H), 2.27 (t, J=7.6 Hz, 2H) |

TABLE 6b

| Example | Chemical structure | NMR spectrum data |
|---|---|---|
| 35 | 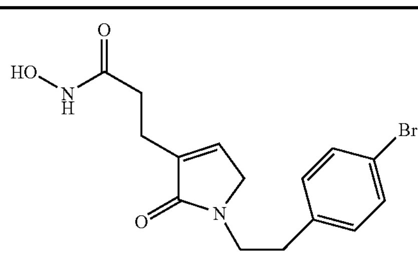 | 7.40 (d, J=8.4 Hz, 2H), 7.10 (d, J=8.1 Hz, 2H), 6.79 (br t, 1H), 3.78 (d, J=1.2 Hz, 2H), 3.66 (t, J=7.3 Hz, 2H), 2.85 (t, J=7.1 Hz, 2H), 2.54 (t, J=7.1 Hz, 2H), 2.30 (t, J=7.4 Hz, 2H) |

TABLE 6b-continued

| Example | Chemical structure | NMR spectrum data |
|---|---|---|
| 36 | 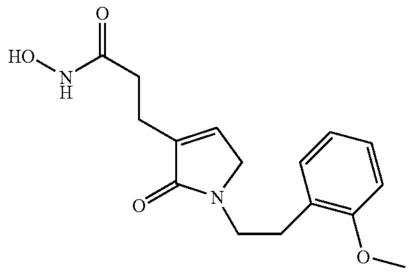 | 7.19-7.13 (m, 1H), 7.03-7.01 (m, 1H), 6.81(t, J=7.4 Hz, 2H), 6.70 (br t, 3.78(s, 3H), 3.69 (s, 2H), 3.63 (t, 1H), Hz, 2H), 2.85 (t, J=7.1 Hz, 2H), 2.52 (t, J=7.7 Hz, 2H), 2.27 (t, J=7.6 Hz, 2H) |
| 37 | 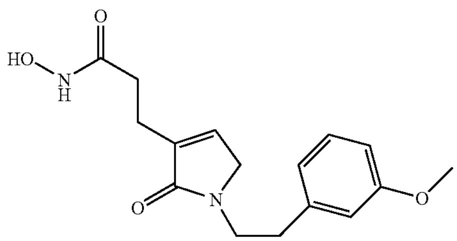 | 7.14(t, J=7.6 Hz, 1H), 6.72-6.67 (m, 4H), 3.12 (s, 3H), 3.65 (s, 2H), 3.60 (br t, 2H), 2.80 (t, J=7.1 Hz, 2H), 2.51 (t, J=7.3 Hz, 2H), 2.25 (t, J=7.3 Hz, 2H) |
| 38 | 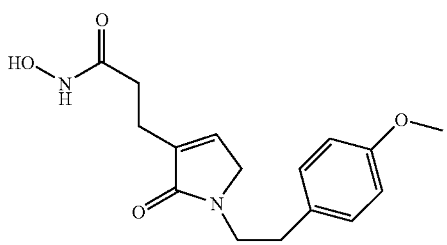 | 7.02 (d, J=8.7 Hz, 2H), 6.76 (d, J= 8.4 Hz, 2H), 6.66 (br t, 1H), 3.72 (s, 3H), 3.62-3.56 (m, 4H), 2.76 (t, J=7.3 Hz, 2H), 2.51 (t, J=7.3 Hz, 2H), 2.25 (t, J=7.6 Hz, 2H) |
| 39 | 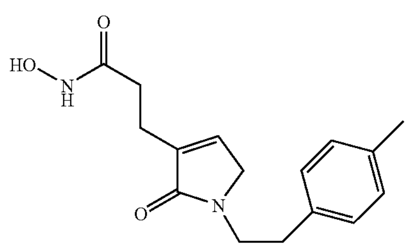 | 7.05 (s, 4H), 6.74 (br t, 1H), 3.72 (d, J=1.2 Hz, 2H), 3.64 (t, J=7.3 Hz, 2H), 3.31-3.29, (m, 2H), 2.82 (t, J=7.3 Hz, 2H), 2.54 (t, J=7.1 Hz, 2H), 2.31 (d, J= 7.8 Hz, 2H), 2.27 (s, 3H). |

Example 40

Preparation of N-hydroxy-3-{1-[3-(4-methoxy-phenyl)-propyl]-2-oxo-2,5-dihydro-1H-pyrrol-3-yl}-propionamide (40ah)

Step 1. Preparation of 3-p-tolyl-acrylic acid methyl ester (40aa)

1.0 g of p-tolualdehyde (8.3 mmol) and 4.16 g of triphenyl phosphanyliden-acetic acid methyl ester (12.45 mmol) were dissolved in methylene chloride, the reaction solution was stirred at 90° C. for overnight. After the resulting mixture was concentrated under reduced pressure, a solvent mixture mixed with EtOAc and hexane (1:7) was added thereto with stirring for 1 hr. And then white solid was removed on filter, the residue was filtered and concentrated in vacuo to give 1.39 g of 3-p-tolyl-acrylic acid methyl ester (40aa) (yield: 95%).

Step 2. Preparation of 3-p-tolyl-propionic acid methyl ester (40ab)

1.39 g of 3-p-tolyl-acrylic acid methyl ester (40aa) prepared by above Step 1 was dissolved in methanol solution (7.9 mmol) under argon atmosphere. Then Pd—C was added thereto, hydrogenated under a hydrogen balloon for 1 to 2 hrs at room temperature. The reaction mixture was filtered and concentrated in vacuo. The resulting compound was purified with Silica gel column chromatography with a solvent mixture mixed with EtOAc and hexane (1:10) as an eluant to give 1.24 g of 3-p-tolyl-propionic acid methyl ester (40ab) (yield: 95%).

Step 3. Preparation of 3-p-tolyl-propane-1-ol (40ac)

1.24 g of 3-p-tolyl-propionic acid methyl ester (40ab) prepared by above Step 2 was dissolved in 100 ml of tetrahydrofuran under Argon atmosphere. Then 27 ml of lithium aluminium-hydride was added thereto with stirring for 2 hrs at 0° C. After 3 ml of distilled water, 3 ml of NaOH (1N) and 9 ml of distilled water were added to the reaction mixture sequentially, the mixture was stirred for 30 min and filtered using cellite in glass filter and concentrated in vacuo. The resultant was purified by Silica gel column chromatography with a solvent mixture mixed with methanol and chloroform (1:2) as an eluant to give 971 mg of 3-p-tolyl-propane-1-ol (40ac) (yield: 93%).

Step 4. Preparation of toluene-4-sulfonate-3-p-tolyl-propyl ester (40ad)

2.46 g of tosyl chloride (13 mmol), 3.4 ml of diisopropylamine (19.4 mmol) and 158 mg of 4-(dimethylamino)pyridine (1.29 mmol) were added to reaction solution (6.46 mmol) dissolving 971 mg of 3-p-tolyl-propane-1-ol (40ac) prepared by above step 3 in methylene chloride at 0° C. under Ar atmosphere with stirring for 6 hrs, and the reaction mixture was stirred for 12 hrs at room temperature. After the reaction mixture was neutralized with ammonium chloride, the mixture was extracted with ethyl acetate, washed with saturated NaCl solution, dried over $MgSO_4$, filtered, and concentrated in vacuo. The resultant was purified by Silica gel column chromatography with a solvent mixture mixed with methanol and chloroform (1:7) as an eluant to give 1.3 g of toluene-4-sulfonate-3-p-tolyl-propyl ester (40ad) (yield: 70%).

Step 5. Preparation of allyl-(3-p-tolyl-propyl)-amine (4ae)

1.6 ml of allylamine (21.4 mmol) and 0.97 ml of diisopropyl ethylamine (5.5 mM) were added to the reaction solution (4.27 mmol) containing 1.3 g of allyl-(3-p-tolyl-propyl)-amine (40ae) prepared by above Step 4 dissolved in acetonitrile solution with stirring for 6 hrs at 100° C. After the reaction mixture was neutralized with 10% NaOH solution, the mixture was extracted with chloroform, washed with saturated NaCl solution, dried over $MgSO_4$, filtered, and concentrated in vacuo. The resultant was purified by Silica gel column chromatography with a solvent mixture mixed with methanol and chloroform (1:9) as an eluant to give 687 mg of allyl-(3-p-tolyl-propyl)-amine (40ae) (yield: 85%).

Step 6. Preparation of 4-[allyl-(3-p-tolyl-propyl)-carbamoyl]-pent-4-enoic acid methyl ester (40af)

683 mg of 2-methylene-pentane dionate-5-methyl ester (4.3 mmol), 902 mg of 1-[3-(dimethylamino)propyl]-3-ethylcarbodiimide (4.7 mmol) and 133 mg of 4-(dimethylamino) pyridine (1.09 mmol) were added to reaction solution (3.62 mmol) dissolving 687 mg allyl-(3-p-tolyl-propyl)-amine (40ae) prepared by above step 5 in 0.5 M of methylene chloride solution under Ar atmosphere and the mixture was stirred for 10 hrs at room temperature. After the resulting mixture was washed with 5% HCl solution (10 ml), the mixture was extracted with ethylacetate, washed with saturated NaCl. And then the extracts were washed with saturated 10 ml of $NaHCO_3$ solution and NaCl solution to separate into an organic layer and water layer. The organic layer was dried over anhydrous $MgSO_4$, filtered and concentrated in vacuo. The resultant was purified by Silica gel column chromatography with a solvent mixture mixed with EtOAc and hexanes (1:2) as an eluant to give 797 mg of 4-[allyl-(3-p-tolyl-propyl)-carbamoyl]-pent-4-enoic acid methyl ester (40af) (yield: 73%).

$^1$H-NMR (300 MHz, $CDCl_3$) δ7.05 (s, 4H), 5.70 (s, 1H), 5.16-5.07 (m, 4H), 3.94 (s, 2H), 3.64 (t, J=3.3 Hz, 3H), 3.36 (s, 2H), 2.67-2.51 (m, 6H), 2.28 (s, 3H), 1.83 (t, J=7.7 Hz, 2H)

Step 7. Preparation of 3-[2-oxo-1-(3-p-tolyl-propyl)-2,5-dihydro-1H-pyrrol-3-yl]-propionic acid methyl ester (40ag)

797 mg of 4-[allyl-(3-p-tolyl-propyl)-carbamoyl]-pent-4-enoic acid methyl ester (40af) (2.6 mmol) prepared by the above Step 6 was added to the catalyst solution containing 180 mg of ruthenium catalyst (0.1 mmol) dissolved in 200 ml of $CH_2Cl_2$ under Ar atmosphere. Then the mixture was stirred for 24 hrs at room temperature, filtered and concentrated in vacuo. The resultant was purified by Silica gel column chromatography with a solvent mixture mixed with EtOAc and hexanes (1:1) as an eluant to give 391 mg of 3-[2-oxo-1-(3-p-tolyl-propyl)-2,5-dihydro-1H-pyrrol-3-yl]-propionic acid methyl ester (40ag) (yield: 50%).

$^1$H-NMR (300 MHz, $CDCl_3$) δ 6.96 (s, 4H), 6.56 (s, 1H), 3.67 (s, 2H), 3.55 (s, 3H), 3.37 (t, J=7.2 Hz, 2H), 2.48 (t, J=8.2 Hz, 6H), 2.19 (s, 3H), 1.76 (t, J=7.6 Hz, 2H)

Step 8. Preparation of N-hydroxy-3-[2-oxo-1-(3-p-tolyl-propyl)-2,5-dihydro-1H-pyrrol-3-yl]-propionamide (40ah)

100 mg of 3-[2-oxo-1-(3-p-tolyl-propyl)-2,5-dihydro-1H-pyrrol-3-yl]-propionic acid methyl ester (40ag) prepared by the above Step 7 was dissolved in methanol solution (0.33 mmol) and then 1.7 M methanolic suspension solution containing $NH_2OK$ (0.82 ml, 5.0 mmol) was added thereto at 0° C. and the resulting mixture was stirred for 8 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 50 mg of N-hydroxy-3-[2-oxo-1-(3-p-tolyl-propyl)-2,5-dihydro-1H-pyrrol-3-yl]-propionamide (40ah) (yield: 50%).

$^1$H-NMR (300 MHz, $CDCl_3$) δ 7.21 (s, 4H), 6.95 (s, 1H), 3.96 (s, 2H), 3.60 (s, 2H), 2.72 (s, 5H), 2.45 (s, 3H), 1.99 (s, 2H)

Example 41

Preparation of N-hydroxy-3-[2-oxo-1-(3-o-tolyl-propyl)-2,5-dihydro-1H-pyrrol-3-yl]-propionamide (41ah)

N-hydroxy-3-[2-oxo-1-(3-o-tolyl-propyl)-2,5-dihydro-1H-pyrrol-3-yl]-propionamide (41ah) was prepared by the similar procedure described in above Example 40 (See Table 7).

Example 42

Preparation of N-hydroxy-3-[2-oxo-1-(3-m-tolyl-propyl)-2,5-dihydro-1H-pyrrol-3-yl]-propionamide (42ah)

N-hydroxy-3-[2-oxo-1-(3-m-tolyl-propyl)-2,5-dihydro-1H-pyrrol-3-yl]-propionamide (42ah) was prepared by the similar procedure described in above Example 40 (See Table 7).

Example 43

Preparation of N-hydroxy-3-{1-[3-(4-isopropyl-phenyl)-propyl]-2-oxo-2,5-dihydro-1H-pyrrol-3-yl]-propionamide (43ah)

N-hydroxy-3-{1-[3-(4-isopropyl-phenyl)-propyl]-2-oxo-2,5-dihydro-1H-pyrrol-3-yl]-propionamide (43ah) was prepared by the similar procedure described in above Example 40 (See Table 7).

Example 44

Preparation of 3-{1-[3-(4-bromo-phenyl)-propyl]-2-oxo-2,5-dihydro-1H-pyrrol-3-yl]-N-hydroxy-propionamide (44ah)

3-{1-[3-(4-bromo-phenyl)-propyl]-2-oxo-2,5-dihydro-1H-pyrrol-3-yl]-N-hydroxy-propionamide (44ah) was prepared by the similar procedure described in above Example 40 (See Table 7).

Example 45

Preparation of 3-{1-[3-(4-chloro-phenyl)-propyl]-2-oxo-2,5-dihydro-1H-pyrrol-3-yl]-N-hydroxy-propionamide (45ah)

3-{1-[3-(4-chloro-phenyl)-propyl]-2-oxo-2,5-dihydro-1H-pyrrol-3-yl]-N-hydroxy-propionamide (45ah) was prepared by the similar procedure described in above Example 40 (See Table 7).

Example 46

Preparation of N-hydroxy-3-{1-[3-(4-methoxy-phenyl)-propyl]-2-oxo-2,5-dihydro-1H-pyrrol-3-yl]-propionamide (46ah)

N-hydroxy-3-{1-[3-(4-methoxy-phenyl)-propyl]-2-oxo-2,5-dihydro-1H-pyrrol-3-yl]-propionamide (46ah) was prepared by the similar procedure described in above Example 40 (See Table 7).

Example 47

Preparation of N-hydroxy-3-{1-[3-(2-methoxy-phenyl)-propyl]-2-oxo-2,5-dihydro-1H-pyrrol-3-yl]-propionamide (47ah)

N-hydroxy-3-{1-[3-(2-methoxy-phenyl)-propyl]-2-oxo-2,5-dihydro-1H-pyrrol-3-yl]-propionamide (47ah) was prepared by the similar procedure described in above Example 40 (See Table 7).

Example 48

Preparation of N-hydroxy-3-{1-[3-(3-methoxy-phenyl)-propyl]-2-oxo-2,5-dihydro-1H-pyrrol-3-yl]-propionamide (48ah)

N-hydroxy-3-{1-[3-(3-methoxy-phenyl)-propyl]-2-oxo-2,5-dihydro-1H-pyrrol-3-yl]-propionamide (48ah) was prepared by the similar procedure described in above Example 40 (See Table 7).

TABLE 7

| Example | Chemical structure | NMR spectrum data |
| --- | --- | --- |
| 41 | 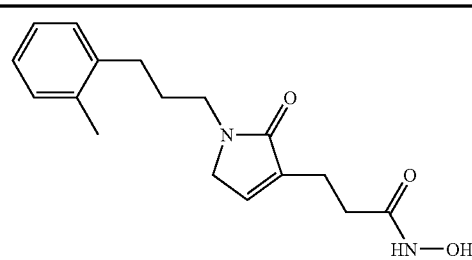 | 7.08 (d, J=4.2 Hz, 4H), 6.69 (s, 1H), 3.80 (s, 2H), 3.48 (d, J=6.6 Hz, 2H), 2.57 (d, J=9.0 Hz, 6H), 2.25 (d, J=6.3 Hz, 2H), 1.79 (s, 2H) |
| 42 | 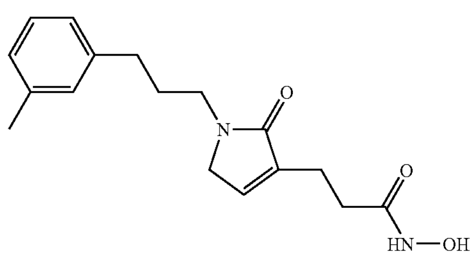 | 7.02-6.97 (m, 1H), 6.81 (d, J=8.4 Hz, 3H), 6.64 (s, 1H), 4.07 (s, 2H), 3.71 (s, 2H), 3.32 (t, J=7.4 Hz, 2H), 2.43 (t, J=7.7 Hz, 5H), 2.17 (t, J=6.5 Hz, 4H), 1.78-1.68 (m, 2H) |
| 43 | 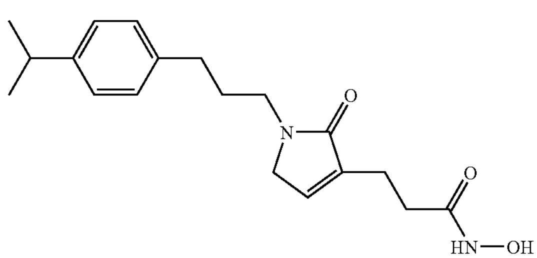 | 10.23 (s, 1H), 7.09 (dd, J=6.0 Hz, 4H), 6.73 (s, 1H), 3.79 (s, 2H), 3.45 (t, J=5.1 Hz, 2H), 2.87-2.80 (m, 1H), 2.61 (s, 1H), 2.56 (t, J=5.9 Hz, 2H), 2.46 (s, 2H), 1.88-1.81 (m, 2H), 1.26-1.19 (m, 6H) |

TABLE 7-continued

| Example | Chemical structure | NMR spectrum data |
|---|---|---|
| 44 | 4-Br-C6H4-(CH2)3-N(pyrrolinone)-CH2CH2C(O)NHOH | 7.23 (t, J=5.5 Hz, 1H), 7.14 (t, J=5.5 Hz, 3H), 6.73 (s, 1H), 3.77 (s, 2H), 3.43 (t, 5.0 Hz, 2H), 2.58 (t, J=5.7 Hz, 4H), 2.45 (s, 2H), 1.88-1.81 (m, 2H) |
| 45 | 4-Cl-C6H4-(CH2)3-N(pyrrolinone)-CH2CH2C(O)NHOH | 7.23-7.04 (m, 4H), 6.73 (s, 1H), 3.77 (s, 2H), 3.43 (t, J=5.7 Hz, 2H), 2.56 (t, J=12.9 Hz, 3H), 2.42 (s, 2H), 1.83 (t, J=6.7 Hz, 2H) |
| 46 | 4-MeO-C6H4-(CH2)3-N(pyrrolinone)-CH2CH2C(O)NHOH | 7.03 (d, J=8.7 Hz, 2H), 6.79-6.75 (m, 2H), 6.72 (s, 1H), 3.72 (d, J=9.9 Hz, 5H), 3.40 (t, J=7.3 Hz, 2H), 2.58-2.42 (m, 6H), 1.78 (t, J=7.4 Hz, 2H) |
| 47 | 2-MeO-C6H4-(CH2)3-N(pyrrolinone)-CH2CH2C(O)NHOH | 7.16-7.06 (m, 2H), 6.84-6.67 (m, 3H), 3.79 (t, J=5.5 Hz, 2H), 3.75 (t, J=3.4 Hz, 3H), 3.50-3.41 (m, 2H), 2.55 (t, J=7.7 Hz, 3H), 2.43 (s, 1H), 1.87 (s, 2H), 1.84-1.77 (m, 2H) |
| 48 | 3-MeO-C6H4-(CH2)3-N(pyrrolinone)-CH2CH2C(O)NHOH | 7.19-7.10 (m, 1H), 6.71 (d, J=10.8 Hz, 4H), 3.75 (s, 5H), 3.49-3.40 (m, 2H), 2.55 (t, J=7.7 Hz, 4H), 2.43 (s, 2H), 1.88-1.84 (m, 2H) |

Example 49

Preparation of N-hydroxy-3-(1-naphthalene-2-ylm-ethyl)-2-oxo-2,5-dihydro-1H-pyrrol-3-yl)-propiona-mide (1e')

N-hydroxy-3-(1-naphthalene-2-ylmethyl-2-oxo-2,5-dihydro-1H-pyrrol-3-yl)-propionamide (1e') was prepared by the similar procedure described in above Example 1 (See Table 8).

TABLE 8

| Example | Chemical structure | NMR spectrum or LC-MS data |
|---|---|---|
| 49 | 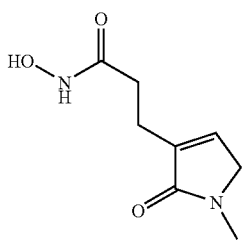 | RT: 393-5.93 (Mass: 311.2) |

Example 50

Preparation of N-hydroxy-3-(1-methyl-2-oxo-2,5-dihydro-1H-pyrrol-3-yl)-propionamide (2h')

Step 1. Preparation of 3-(2-oxo-2,5-dihydro-1H-pyrrol-3-yl)-propionic acid methyl ester (2f)

0.1 ml of triethylsilane (0.63 mmol) was added to the reaction solution containing 200 mg of 3-[1-(2,4-dimethoxy-benzyl)-2-oxo-2,5-dihydro-1H-pyrrol-3-yl]-propionic acid methyl ester (0.63 mmol) dissolved in 0.7 ml of trifluoroacetic acid solution at 0° C. After the reaction mixture was heated for 1 hr, the mixture was filtered and concentrated in vacuo to remove solvent. Then the resulting mixture was dissolved in 20 ml of chloroform solution to separate into an organic layer and water layer. The organic layer was washed with 5 ml of saturated NaHCO$_3$ solution and 5 ml of saturated NaCl solution, dried over anhydrous MgSO$_4$, filtered and concentrated in vacuo. The resultant was purified by Silica gel column chromatography with a solvent mixture mixed with EtOAc and hexanes (19:1) as an eluant to give 50 mg of 3-(2-oxo-2,5-dihydro-1H-pyrrol-3-yl)-propionic acid methyl ester (2f) (yield: 47%).

$^1$H-NMR (300 MHz, CDCl$_3$) δ 6.76 (br t, 1H), 3.89 (d, J=1.3 Hz, 2H), 3.63 (t, J=1.9 Hz, 3H), 2.58 (s, 4H)

Step 2. Preparation of 3-(1-methyl-2-oxo-2,5-dihydro-1H-pyrrol-3-yl)-propionic acid methyl ester (2g)

0.33 ml of NaHMDS solution (1.0 M in THF, 0.33 mmol) was added to 0.6 ml of THF solution containing 50 mg of 3-(2-oxo-2,5-dihydro-1H-pyrrol-3-yl)-propionic acid methyl ester (2f) (0.30 mmol) prepared by the Step 1 in a dropwise manner at −79° C. and stirred for 30 mins. After 0.3 ml of dimethyl sulfate 0.36 mmol) was added thereto, the reaction mixture was stirred for 4 hrs at 0° C. Then the resulting mixture was dissolved in 2 ml of saturated NH$_4$Cl solution and extracted with 7 ml of ethyl acetate to separate into an organic layer and water layer. The organic layer was washed with 2 ml of saturated NaHCO$_3$ solution and 2 ml of saturated NaCl solution, dried over anhydrous MgSO$_4$, filtered and concentrated in vacuo. The resultant was purified by Silica gel column chromatography with EtOAc as an eluant to give 18 mg of 3-(1-methyl-2-oxo-2,5-dihydro-1H-pyrrol-3-yl)-propionic acid methyl ester (2g) (yield: 33%).

$^1$H-NMR (300 MHz, CDCl$_3$) δ 6.65 (br t, 1H), 3.81 (s, 1H), 3.64 (s, 3H), 3.01 (s, 3H), 2.60 (t, 4H).

Step 3. Preparation of N-hydroxy-3-(1-methyl-2-oxo-2,5-dihydro-1H-pyrrol-3-yl)-propionamide (2h)

18 mg of 3-(1-methyl-2-oxo-2,5-dihydro-1H-pyrrol-3-yl)-propionic acid methyl ester (2g) prepared by the above Step 2 was dissolved in methanol solution (0.1 mmol) and then 1.7 M methanolic suspension solution containing NH$_2$OK (0.09 ml, 0.15 mmol) was added thereto at 0° C. and the resulting mixture was stirred for 1 hr at room temperature. The resulting mixture was neutralized with 0.03 ml of acetic acid, diluted with 10% methanol/chloroform solution, filtered and concentrated in vacuo. The resulting compound was purified by Silica gel column chromatography with a solvent mixture mixed with EtOAc and methanol (5:2) as an eluant to give 11 mg of N-hydroxy-3-(1-methyl-2-oxo-2,5-dihydro-1H-pyrrol-3-yl)-propionamide (2h) (yield: 59%).

$^1$H-NMR (300 MHz, CDCl$_3$) δ 6.76 (br t, 1H), 3.84 (s, 2H), 3.00 (s, 3H), 2.59 (t, J=7.2 Hz, 2H), 2.42 (t, J=7.2 Hz, 2H)

Example 51

Preparation of 3-(1-allyl-2-oxo-2,5-dihydro-1H-pyrrol-3-yl)-N-hydroxy-propionamide (3h')

3-(1-allyl-2-oxo-2,5-dihydro-1H-pyrrol-3-yl)-N-hydroxy-propionamide (3h') was prepared by the similar procedure described in above Example 50 (See Table 9).

TABLE 9

| Example | Chemical structure | NMR spectrum data |
| --- | --- | --- |
| 51 | (structure) | 6.89(br t, 1H), 5.98-5.67(m, 2H), 5.10-5.08 (m, 1H), 3.36(t, J=1.8 Hz, 2H), 2.61(s, 2H), 2.06(s, 2H), 1.87(s, 2H) |

Example 52

Preparation of N-hydroxy-3-[1-(2-naphthalene-1-yl-ethyl)-2-oxo-2,5-dihydro-1H-pyrrol-3-yl]-propionamide (4n')

N-hydroxy-3-[1-(2-naphthalene-1-yl-ethyl)-2-oxo-2,5-dihydro-1H-pyrrol-3-yl]-propionamide (4n') was prepared by the similar procedure described in above Example 28 (See Table 10).

Example 53

Preparation of N-hydroxy-3-[1-(2-naphthalene-2-yl-ethyl)-2-oxo-2,5-dihydro-1H-pyrrol-3-yl]-propionamide (5n')

N-hydroxy-3-[1-(2-naphthalene-2-yl-ethyl)-2-oxo-2,5-dihydro-1H-pyrrol-3-yl]-propionamide (5n') was prepared by the similar procedure described in above Example 28 (See Table 10).

Example 54

Preparation of N-hydroxy-3-[2-oxo-1-(2-thiophen-2-yl-ethyl)-2,5-dihydro-1H-pyrrol-3-yl]-propionamide (6n')

N-hydroxy-3-[2-oxo-1-(2-thiophen-2-yl-ethyl)-2,5-dihydro-1H-pyrrol-3-yl]-propionamide (6n') was prepared by the similar procedure described in above Example 28 (See Table 10).

TABLE 10

| Example | Chemical structure | NMR spectrum data |
| --- | --- | --- |
| 52 | (structure) | 8.01(d, J=8.1 Hz, 1H), 7.77(d, J=8.7 Hz, 1H), 7.66(d, J=8.1 Hz, 1H), 7.48-7.20(m, 4H), 6.62(br t, 1H), 3.56(s, 2H), 3.30-3.25(m, 2H), 2.51(t, J=7.3 Hz, 2H), 2.25(t, J=7.3 Hz, 2H) |
| 53 | (structure) | 7.73-7.66(m, 3H), 7.53(s, 1H), 7.40-7.32 (m, 2H), 7.22(s, 1H), 6.61(br t, 1H), 3.69(t, J=7.3 Hz, 2H), 3.60(s, 2H), 2.97(t, J=7.0 Hz, 2H), 2.49(t, J=7.2 Hz, 2H), 2.24(t, J= 7.3 Hz, 2H) |

TABLE 10-continued

| Example | Chemical structure | NMR spectrum data |
|---|---|---|
| 54 | (structure) | 7.08(br t, 1H), 6.85(t, J=4.0 Hz, 1H), 6.74(s, 1H), 6.68(br t, 1H), 3.65(s, 4H), 3.37-3.29(m, 1H), 3.05(t, J=6.1 Hz, 2H), 2.51(d, J=4.8 Hz, 2H), 2.28(s, 1H) |

Example 55

Preparation of 3-[1-(3-biphenyl-4-yl-propyl)-2-oxo-2,5-dihydro-1H-pyrrol-3-yl]-N-hydroxy-propionamide (7w')

3-[1-(3-biphenyl-4-yl-propyl)-2-oxo-2,5-dihydro-1H-pyrrol-3-yl]-N-hydroxy-propionamide (7w') was prepared by the similar procedure described in above Example 40 (See Table 11).

Example 56

Preparation of N-hydroxy-3-[1-(3-naphthalene-2-yl-propyl)-2-oxo-2,5-dihydro-1H-pyrrol-3-yl]-propionamide (8w')

N-hydroxy-3-[1-(3-naphthalene-2-yl-propyl)-2-oxo-2,5-dihydro-1H-pyrrol-3-yl]-propionamide (8w') was prepared by the similar procedure described in above Example 40 (See Table 11).

Example 57

Preparation of 3-[1-(2,4-Dimethoxybenzyl)-2-oxo-1,2,5,6-tetrahydropyridin-3-yl]N-hydroxypropionamide (e1)

Step 1. Preparation of But-3-enyl-(2,4-dimethoxybenzyl)amine (b)

0.5 ml of 1-Bromo-3-butene (4.93 mmol) and 0.94 ml of diisopropyl ethylamine (5.40 mmol) were added to the reaction solution containing 0.74 ml of 2,4-dimethoxybenzylamine (a) (4.93 mmol) dissolved in methylene chloride with stirring and the mixture was stirred at room temperature for overnight. The reaction mixture was washed with saturated NaCl solution, dried over $MgSO_4$, filtered and concentrated in vacuo. The resulting compound was purified with Silica gel column chromatography with EtOAc solvent as an eluant to give 436 mg of the pure title compound (b) (yield: 40%).

TABLE 11

| Example | Chemical structure | NMR spectrum data |
|---|---|---|
| 55 | (structure) | 7.51(dd, J=8.0 Hz, 4H), 7.37(t, J=7.4 Hz, 2H), 7.26(q, J=7.2 Hz, 3H), 6.81(s, 1H), 4.79(s, 2H), 3.89(s, 2H), 3.48(t, J=7.1 Hz, 2H), 2.64(t, J=7.7 Hz, 2H), 2.56(t, J=5.1 Hz, 2H), 2.32(t, J=6.9 Hz, 1H) |
| 56 | (structure) | 10.54(s, 1H), 7.71(dd, J=7.9 Hz, 3H), 7.54(s, 1H), 7.41-7.33(m, 2H), 7.24(d, J=7.8 Hz, 1H), 6.64(s, 1H), 3.67(s, 2H), 3.40(s, 2H), 2.69(t, J=6.7 Hz, 2H), 2.57(s, 2H), 2.41(s, 2H), 1.86(s, 2H) |

¹H-NMR (300 MHz, CDCl₃) δ 7.10 (d, J=8.1 Hz, 1H), 6.41 (m, 2H), 5.75 (m, 1H), 5.01 (m, 2H), 3.78 (s, 3H), 3.77 (s, 3H), 3.70 (s, 2H), 2.63 (t, J=7.5 Hz, 2H), 2.24 (m, 2H)

Step 2. Preparation of 4-[But-3-enyl-(2,4-dimethoxy-benzyl)-carbamoyl]-pent-4-enoic acid methyl ester (c)

714 mg of 2-methylene-pentane dionate-5-methyl ester (4.52 mmol), 953 mg of EDC (4.97 mmol) and 110 mg of DMAP (0.9 mmol) were added to 0.5 M of reaction solution dissolving the compound (b) prepared by above step 1 in methylene chloride and the mixture was stirred for 5 hrs at room temperature. The resulting mixture was diluted with ethyl acetate, and washed with 5% HCl solution (10 ml) and 10 ml of saturated NaHCO₃ solution to separate into an organic layer and water layer. The organic layer was dried over anhydrous MgSO₄, filtered and concentrated in vacuo. The resultant was purified by Silica gel column chromatography with a solvent mixture mixed with EtOAc and hexanes (1:2) as an eluant to give 1.39 g of 4-[but-3-enyl-(2,4-dimethoxybenzyl)-carbamoyl]-pent-4-enoic acid methyl ester (c) (yield: 40%).

Step 3. Preparation of 3-[1-(2,4-dimethoxybenzyl-2-oxo-1,2,5,6-tetrahydro-pyridin-3-yl]-propionic acid methyl ester (d)

130 mg of the compound (c) (0.360 mmol) prepared by the above Step 2 was added to the catalyst solution containing 20 mg of ruthenium (0.024 mmol) dissolved in CH₂Cl₂. Then the mixture was stirred for 24 hrs at room temperature, filtered and concentrated in vacuo. The resultant was purified by Silica gel column chromatography with methanol/chloroform (1:10) solvent mixture as an eluant to give 108 mg of the title compound (d) (yield: 90%).

¹H-NMR (300 MHz, CDCl₃) δ 7.17 (d, J=8.9 Hz, 1H), 6.41 (m, 2H), 6.26 (t, J=4.3 Hz, 1H), 4.53 (s, 2H), 3.77 (s, 3H), 3.76 (s, 3H), 3.62 (s, 3H), 3.28 (t, J=7.1 Hz, 2H), 2.61-2.47 (m, 4H), 2.22 (m, 2H)

¹³C-NMR (75 MHz, CDCl₃) δ 173.6, 164.8, 160.2, 158.5, 134.2, 133.9, 130.4, 118.0, 104.1, 98.3, 55.2, 51.3, 45.0, 44.3, 33.3, 26.6, 23.9

Step 4. Preparation of 3-[1-(2,4-dimethoxybenzyl)-2-oxo-1,2,5,6-tetrahydro-pyridin-3-yl]-N-hydroxy-propionamide (e1)

46 mg of compound (d) prepared by the above Step 3 was dissolved in methanol solution (0.138 mmol) and then 1.7 M methanolic suspension solution containing NH₂OK (0.122 ml, 0.207 mmol) was added thereto at 0° C. and the resulting mixture was stirred for 3 hrs at room temperature. The resulting mixture was neutralized with 0.02 ml of acetic acid, diluted with 10 ml of ethyl acetate solution, filtered and concentrated in vacuo. The resulting compound was purified by column chromatography on Silica gel with methanol/chloroform (1:10) solvent mixture as an eluant to give 32 mg of the title compound (e1) (yield: 73%).

¹H-NMR (300 MHz, CDCl₃) δ 7.122 (d, J=9.0 Hz, 1H), 6.415-6.331 (m, 3H), 4.505 (s, 2H), 3.750 (s, 3H), 3.744 (s, 3H), 3.271 (t, J=6.9 Hz, 2H), 2.552 (m, 2H), 2.381 (m, 2H), 2.220 (m, 2H)

¹³C-NMR (75 MHz, CDCl₃) δ 170.1, 165.4, 160.2, 158.5, 135.8, 133.5, 130.4, 117.5, 104.2, 98.3, 55.3, 44.9, 44.6, 32.8, 27.1, 23.8

Example 58

Preparation of N-hydroxy-3-(1-benzyl-2-oxo-1,2,5,6-tetrahydro-pyridin-3-yl)-propionic acid (e2)

N-hydroxy-3-(1-benzyl-2-oxo-1,2,5,6-tetrahydro-pyridin-3-yl)-propionic acid (e2) was prepared by the similar procedure described in above Example 57 (See Table 12).

Example 59

Preparation of N-hydroxy-3-[1-(4-nitro-benzyl)-2-oxo-1,2,5,6-tetrahydro-pyridin-3-yl)-propionamide (e3)

N-hydroxy-3-[1-(4-nitro-benzyl)-2-oxo-1,2,5,6-tetrahydro-pyridin-3-yl]-propionamide (e3) was prepared by the similar procedure described in above Example 57 (See Table 12).

Example 60

Preparation of 3-(1-benzyl-2-oxo-1,2,5,6-tetrahydro-pyridin-3-yl)-N-hydroxy propionamide (e4)

3-(1-benzyl-2-oxo-1,2,5,6-tetrahydro-pyridin-3-yl)-N-hydroxy propionamide (e4) was prepared by the similar procedure described in above Example 57 (See Table 12).

Example 61

Preparation of N-hydroxy-3-[2-oxo-1-(4-phenyl-butyl)-1,2,5,6-tetrahydro-pyridin-3-yl]-propionamide (e5)

N-hydroxy-3-[2-oxo-1-(4-phenyl-butyl)-1,2,5,6-tetrahydro-pyridin-3-yl]-propionamide (e5) was prepared by the similar procedure described in above Example 57 (See Table 12).

Example 62

Preparation of N-hydroxy-3-(2-oxo-1-phenethyl-1,2,5,6-tetrahydro-pyridin-3-yl)-propionamide (e6)

N-hydroxy-3-(2-oxo-1-phenethyl-1,2,5,6-tetrahydro-pyridin-3-yl)-propionamide (e6) was prepared by the similar procedure described in above Example 57 (See Table 12).

TABLE 12

| Example | Chemical structure | NMR spectrum data |
| --- | --- | --- |
| 58 | 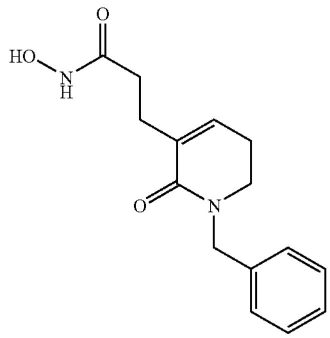 | 7.28(m, 5H), 6.44(t, J=4.3 Hz, 1H), 4.61(s, 2H), 3.33(m, 2H), 2.57(t, J=7.5 Hz, 2H), 2.28(m, 4H) |
| 59 | 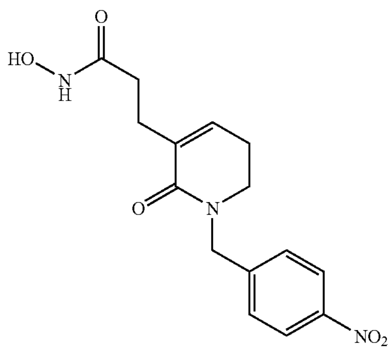 | 8.14(d J=8.4 Hz 2H), 7.40(t J=7.2 Hz 2H), 6.42(br t 1H), 4.67(s 2H), 3.32(t J=6.3 Hz 2H), 2.67-2.32(m 6H) |
| 60 | 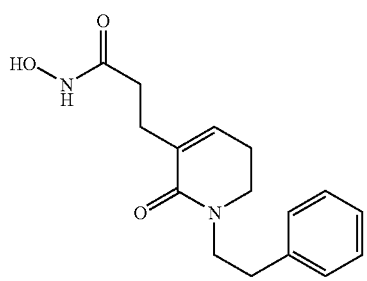 | 7.29-7.18(m 5H) 6.40(br t 1H), 3.62(t J=7.2 Hz 2H), 3.19(t J=7.1 Hz 2H), 2.85(t J=7.1 Hz 2H), 2.54-2.44(m 2H), 2.18-2.15(m 4H) |
| 61 | 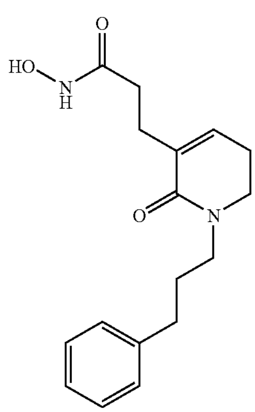 | 7.24-7.11(m, 5H), 6.31(br t, 1H), 3.35(br t, 2H), 3.23(br t, 2H), 2.55(d, J=6.6 Hz, 4H), 2.33(s, 2H), 2.18(s, 2H), 1.80(br t, 2H) |
| 62 | 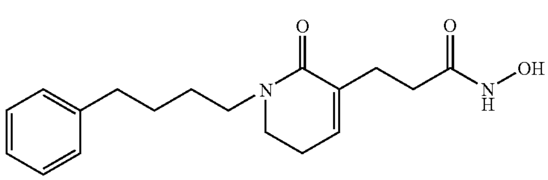 | 7.28-7.13(m, 5H), 6.36(t, J=3.9, 1H), 3.39(t, J=6.75, 2H), 3.29(t, J=7.05, 2H), 2.62(t, J=7.05, 2H), 2.54(t, J=6.75, 2H), 2.40(t, J=6.75, 2H), 2.27(ab, J=6.0, 5.4, 2H), 1.58(t, J=2.7, 4H) |

Example 63

Preparation of 3-[1-(2,4-dimethoxybenzyl)-2-oxo-1,2,5,6-tetrahydro-pyridin-3-yl]-propionic acid (f1)

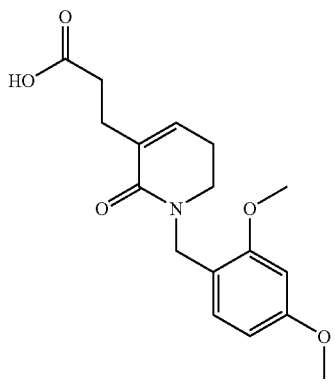

11 mg of LiOH.H$_2$O solution (0.26 mmol) was added to 0.75 ml of THF solution containing 58 mg of 3-[1-(2,4-dimethoxy benzyl)-2-oxo-1,2,5,6-tetrahydro pyridine-3-yl]-propionic acid methyl ester (d) (0.17 mmol) in a dropwise manner at 0° C. After the reaction mixture was stirred for 2 hrs at 0° C. and for 1 hr at room temperature, 5% HCl was added to the mixture to pH 2. Then the mixture was extracted three times with 10 ml of ethyl acetate, the organic layer was washed with saturated NaCl solution, dried over anhydrous MgSO$_4$, filtered and concentrated in vacuo. The resulting compound was purified with Silica gel column chromatography with methanol/chloroform (1:10) solvent mixture as an eluant to give 44 mg of the title compound (f1) (yield: 80%).

$^1$H-NMR (300 MHz, CDCl$_3$) δ 7.16 (d, J=8.9 Hz, 1H), 6.42 (m, 2H), 6.29 (t, J=4.3 Hz, 1H), 4.54 (s, 2H), 3.76 (s, 3H), 3.76 (s, 3H), 3.29 (t, J=7.2 Hz, 2H), 2.56 (m, 4H), 2.22 (m, 2H)

$^{13}$C-NMR (75 MHz, CDCl$_3$) δ 177.7, 165.1, 160.1, 158.5, 134.6, 133.9, 130.5, 117.7, 104.1, 98.3, 55.2, 44.9, 44.5, 33.5, 26.3, 23.8

Example 64

Preparation of 3-(1-benzyl-2-oxo-1,2,5,6-tetrahydro-pyridin-3-yl)-propionic acid (f2)

3-(1-benzyl-2-oxo-1,2,5,6-tetrahydro-pyridin-3-yl)-propionic acid (f2) was prepared by the similar procedure described in above Example 63 (See Table 13).

Example 65

Preparation of 3-[1-(4-nitro-benzyl)-2-oxo-1,2,5,6-tetrahydro-pyridin-3-yl]-propionic acid (f3)

3-[1-(4-nitro-benzyl)-2-oxo-1,2,5,6-tetrahydro-pyridin-3-yl]-propionic acid (f3) was prepared by the similar procedure described in above Example 63 (See Table 13).

Example 66

Preparation of 3-[2-oxo-1-(3-phenyl-propyl)-1,2,5,6-tetrahydro-pyridin-3-yl]-propionic acid (f4)

3-[2-oxo-1-(3-phenyl-propyl)-1,2,5,6-tetrahydro-pyridin-3-yl]-propionic acid (f4) was prepared by the similar procedure described in above Example 63 (See Table 13).

Example 67

Preparation of 3-[2-oxo-1-(4-phenyl-butyl)-1,2,5,6-tetrahydro-pyridin-3-yl]-propionic acid (f5)

3-[2-oxo-1-(4-phenyl-butyl)-1,2,5,6-tetrahydro-pyridin-3-yl]-propionic acid (f5) was prepared by the similar procedure described in above Example 63 (See Table 13).

Example 68

Preparation of 3-(2-oxo-1-phenethyl-1,2,5,6-tetrahydro-pyridin-3-yl)-propionic acid (f6)

3-(2-oxo-1-phenethyl-1,2,5,6-tetrahydro-pyridin-3-yl)-propionic acid (f6) was prepared by the similar procedure described in above Example 63 (See Table 13).

TABLE 13

| Example | Chemical structure | NMR spectrum data |
| --- | --- | --- |
| 64 | 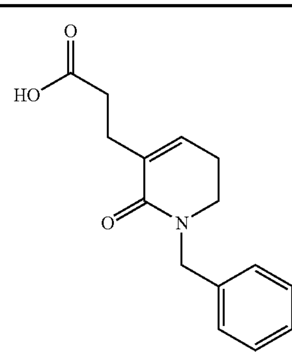 | 7.25(m, 5H), 6.34(t, J=4.2 Hz, 1H), 4.60(s, 2H), 3.26(t, J=7.1 Hz, 2H), 2.59(m, 4H), 2.25(m, 2H) |

TABLE 13-continued

| Example | Chemical structure | NMR spectrum data |
|---|---|---|
| 65 | 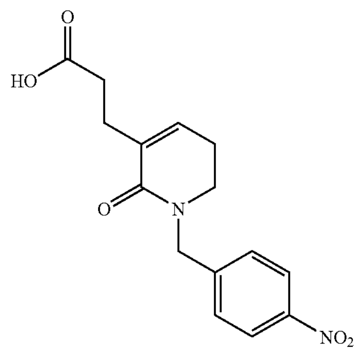 | 8.16(d J=8.7 Hz 2H), 7.42(d, J=8.6 Hz, 2H), 6.39(t J=4.3 Hz, 1H)4.69(s, 2H)3.32(t, J=7.2 Hz, 2H)2.64-2.53(m, 4H), 2.33(dd J=6.9 Hz, 5.7 Hz, 2H) |
| 66 | 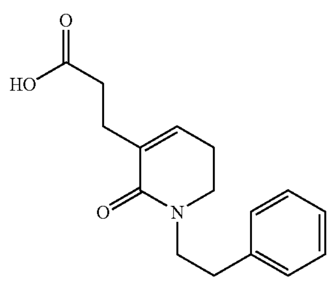 | 9.92(br s 1H), 7.28-7.15(m, 5H), 6.28(t, J=4.4, 1H), 3.60(t J=7.4, 2H)3.16(t, J=7.2, 2H), 2.84(t, J=7.4, 2H)2.58-2.48(m, 4H) 2.15(AB, J=11.4, 6.8, 2H) |
| 67 | 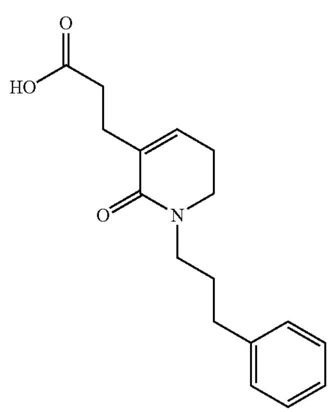 | 7.28-7.10(m, 5H), 6.28(br, t, 1H), 5.75-5.60(m, 1H), 5.01(d, J=16.5 Hz, 2H), 3.41-3.26(m, 3H) 2.63-2.26(m, 7H)1.84(t, J=6.8 Hz, 2H) |
| 68 | 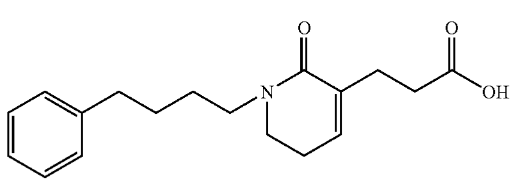 | 7.256-7.138(m, 5H), 6.33(br, t, 1H), 3.42(t, J=6.9, 2H), 3.32(t, J=7.35, 2H), 2.63(t, J=7.05, 2H), 2.547(d, J=2.4, 4H), 2.30(d, J=4.5, 2H), 1.61(q, J=1.5, 4H) |

Example 69

Preparation of 3-(1-benzyl-2-oxo-1,2,5,6-tetrahydro-pyridin-3-yl)-N-pyridin-2-yl-propionamide (g1)

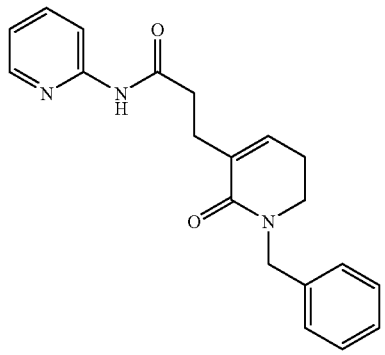

Pyridyl amine was added to organic solvent dissolving of 3-(1-benzyl-2-oxo-1,2,5,6-tetrahydro-pyridin-3-yl)-propionic acid (0.12 mmol) in EDC. The resulting compound was purified by Silica gel column chromatography with methanol/chloroform (1:20) solvent mixture as an eluant to give 16 mg of the title compound (g1) (yield: 39%).

Example 70

Preparation of N-(2-amino-phenyl)-3-(1-benzyl-2-oxo-1,2,5,6-tetrahydro-pyridin-3-yl)-propionamide (g2)

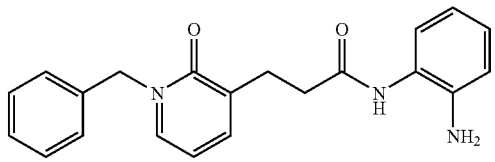

40 mg of 1,2-phenylenediamine (0.37 mmol), 77 mg of EDC (0.4 mmol) and 1 mg of DMAP (3 M %) were added to reaction solution dissolving 3-(1-benzyl-2-oxo-1,2,5,6-tetrahydro-pyridin-3-yl)-propionic acid prepared by above Example 8 in 1 ml of methylene chloride under Argon atmosphere. After the mixture was stirred for 13 hrs at room temperature, the resulting mixture was diluted with ethyl acetate and washed with 10% NaOH solution (10 ml). Then the residue was extracted with 50 ml of chloroform, dried over anhydrous $MgSO_4$, filtered and concentrated in vacuo. The resultant was purified by Silica gel column chromatography with a solvent mixture mixed with methanol and chloroform (1:20) as an eluant to give 96 mg of N-(2-amino-phenyl)-3-(1-benzyl-2-oxo-1,2,5,6-tetrahydro-pyridin-3-yl)-propionamide (g2) (yield: 91%).

$^1$H-NMR (300 MHz, $CDCl_3$) δ8.29 (s, 1H), 7.29-7.19 (m, 5H), 7.13 (d, 1H, J=7.8 Hz), 6.99-6.94 (m, 1H), 6.68 (t, 2H, J=7.9 Hz), 6.37 (t, 1H, J=8.4 Hz), 4.57 (t, 2H, J=7.4 Hz), 3.88 (s, 2H), 3.29-3.21 (m, 2H), 2.68 (t, 2H, J=6.5 Hz), 2.59 (t, 2H, 6.5 Hz), 2.26-2.217 (m, 2H)

Example 71

Preparation of N-(2-amino-phenyl)-3-[1-(2-methyl-benzyl)-2-oxo-1,2,5,6-tetrahydro-pyridin-3-yl)-propionamide (g3)

N-(2-amino-phenyl)-3-[1-(2-methyl-benzyl)-2-oxo-1,2,5,6-tetrahydro-pyridin-3-yl)-propionamide (g3) was prepared by the similar procedure described in above Example 69 and 70 (See Table 14).

Example 72

Preparation of N-(2-amino-phenyl)-3-[1-(2-methyl-benzyl)-2-oxo-1,2,5,6-tetrahydro-pyridin-3-yl)-propionamide (g4)

N-(2-amino-phenyl)-3-[1-(2-methyl-benzyl)-2-oxo-1,2,5,6-tetrahydro-pyridin-3-yl)-propionamide (g4) was prepared by the similar procedure described in above Example 69 and 70 (See Table 14).

TABLE 14

| Example | Chemical structure | NMR spectrum data |
|---|---|---|
| 71 | 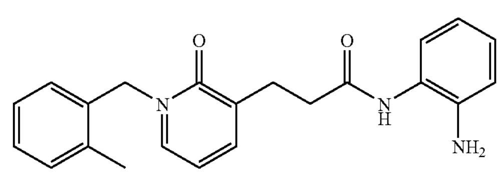 | 8.23(s, 1H), 7.12(dd, 5H, J=6.6 Hz), 6.979(t, 1H, J=7.5 Hz), 6.697(t, 2H, J=8.9 Hz), 6.408(t, 1H, J=7.4 Hz), 4.602(s, 2H), 3.874(s, 2H), 3.239(t, 2H, J=7.1 Hz), 2.702(t, 2H, J=6.8 Hz), 2.604(t, 2H, J=6.3 Hz), 2.260(t, 5H, J=6.3 Hz) |
| 72 | 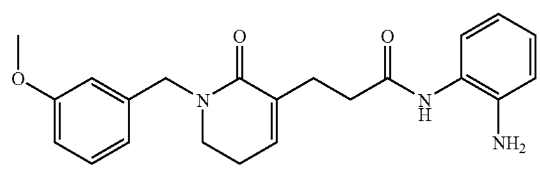 | 8.305(s, 1H), 7.189-7.091(m, 2H), 6.969-6.914(m, 2H), 6.794-6.741(m, 3H), 6.691-6.631(m, 2H), 6.355(t, 1H, J=4.1 Hz), 4.539(s, 2H), 3.965(s, 2H), 3.707(s, 3H), 3.253(t, 2H, J=7.0 Hz), 2.661-2.539(m, 4H), 2.22(dd, 2H, J=7.1 Hz) |

Example 73

Preparation of N-benzyloxy-3-(2-oxo-1-phenethyl-1,2,5,6-tetrahydro-pyridin-3-yl)-propionamide (g5)

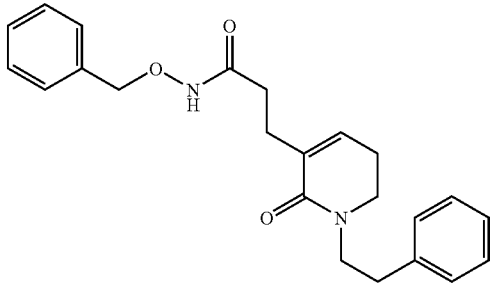

Benzyloxyamine was added to organic solvent dissolving 30 mg of 3-(1-benzyl-2-oxo-1,2,5,6-tetrahydro-pyridin-3-yl)-propionic acid (0.15 mmol) prepared by above Example 12 in EDC. The resulting compound was purified by Silica gel column chromatography with ethylacetate/chloroform (1:1) solvent mixture as an eluant to give 41 mg of the title compound (g5) (yield: 75%).

$^1$H-NMR (300 MHz, CDCl$_3$) δ 7.41-7.15 (m, 1H), 6.34 (br t, 1H), 4.88 (s, 2H), 3.58 (t, J=7.4 Hz, 2H), 3.16 (t, J=7.2 Hz, 2H), 2.82 (t, J=7.2 Hz, 2H), 2.53 (t, J=6.8 Hz, 2H), 2.26 (br s, 1H), 2.19 (dd, J=11.4, 7.1 Hz, 2H)

Example 18

Preparation of 3-[1-(4-acetylamino-benzyl)-2-oxo-1,2,5,6-tetrahydro-pyridin-3-yl]-N-hydroxy-propionamide (j1)

Step 1. Preparation of 3-[1-(4-amino-benzyl)-2-oxo-1,2,5,6-tetrahydro-pyridin-3-yl]-propionic acid methyl ester (h)

50 mg of 3-[1-(2,4-dimethoxybenzyl)-2-oxo-1,2,5,6-tetrahydro-pyridin-3-yl]-propionic acid methyl ester (d) (0.16 mmol) prepared by the Step 3 of above Example 1 was dissolved in methanol solution at room temperature. Then 154 mg of Zn (2.36 mmol) and 0.01 ml of acetic acid (0.16 mmol) were added thereto and the mixture was stirred for 20 hrs at 80° C. The resulting compound was purified by Silica gel column chromatography with a solvent mixture mixed with ethylacetate and hexane (1:1) as an eluant to give 43 mg of 3-[1-(4-amino-benzyl)-2-oxo-1,2,5,6-tetrahydro-pyridin-3-yl]-propionic acid methyl ester (h) (yield: 92%).

$^1$H-NMR (300 MHz, CDCl$_3$) δ 8.22 (d, 1H, J=8.5 Hz), 8.11 (d, 1H, J=8.4 Hz), 7.37 (t, 2H, #: 8.3 Hz), 6.33 (t, 1H, J=4.3 Hz), 4.66 (d, 2H, J=7.5 Hz), 3.63 (s, 3H), 3.29 (t, 2H, J=6.6 Hz), 2.63 (t, 2H, J=6.9 Hz), 2.54 (t, 2H, J=6.6 Hz), 2.28 (t, 2H, J=4.2 Hz)

Step 2. Preparation of 3-[1-(4-acetylamino-benzyl)-2-oxo-1,2,5,6-tetrahydro-pyridin-3-yl]-propionic acid methyl ester (i)

17.5 mg of 3-[1-(4-amino-benzyl)-2-oxo-1,2,5,6-tetrahydro-pyridin-3-yl]-propionic acid methyl ester (h) prepared by above Step 1 was dissolved in methylene chloride solution (0.06 mmol). And then 6 μl of (AcO)$_2$O (0.07 mmol), 0.01 ml of triethylamine (0.08 mmol) and 1.0 mg of DMAP (0.008 mmol) were added thereto and the mixture was stirred for 3 hrs at 0° C. The reaction was stopped by adding methanol and the mixture was extracted three times with 10 ml of ethyl acetate. The organic layer was washed with saturated NaCl solution, dried over anhydrous MgSO$_4$, filtered and concentrated in vacuo. The resulting compound was purified with Silica gel column chromatography with ethylacetate as an eluant to give 46 mg of 3-[1-(4-acetylamino-benzyl)-2-oxo-1,2,5,6-tetrahydro-pyridin-3-yl)-propionic acid methyl ester (i) (yield: 44%).

$^1$H-NMR (300 MHz, CDCl$_3$) δ 8.34 (s, 1H), 7.40 (d, 2H, J=8.4 Hz), 7.10 (d, 2H, J=8.4 Hz), 6.29 (t, 1H, J=4.2 Hz), 4.50 (s, 2H), 3.61 (s, 3H), 3.22 (t, 2H, J=7.1 Hz), 2.59 (t, 2H, J=7.1 Hz), 2.51 (d, 2H, J=6.6 Hz), 2.22 (dd, 2H, J=6.9 Hz), 2.09 (s, 3H)

Step 3. Preparation of 3-[1-(4-acetylamino-benzyl)-2-oxo-1,2,5,6-tetrahydro-pyridin-3-yl)-N-hydroxy-propionamide (j1)

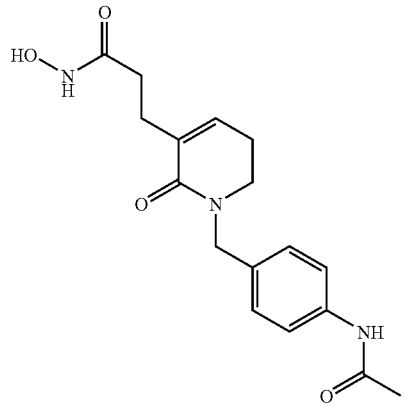

3-[1-(4-acetylamino-benzyl)-2-oxo-1,2,5,6-tetrahydro-pyridin-3-yl)-propionic acid methyl ester (i) prepared by above Step 2 dissolved in organic solvent such as methanol was reacted with amine salt to give 3-[1-(4-acetylamino-benzyl)-2-oxo-1,2,5,6-tetrahydro-pyridin-3-yl]-N-hydroxy-propionamide (j1).

$^1$H-NMR (300 MHz, CDCl$_3$) δ 7.50 (d J=8.0 Hz 2H), 7.23 (d J=8.0 Hz 2H), 6.44 (br t 1H), 4.57 (S 2H), 3.33 (t, J=6.5 Hz, 6H) 2.57 (br t, 2H) 2.30-2.26 (m, 4H) 2.10 (s, 2H)

Example 75

Preparation of N4-[5-(2-hydroxycarbamoyl-ethyl)-6-oxo-3,6-dihydro-2-pyridin-1-yl-methyl]-phenyl-benzamide (j2)

N-4-[5-(2-hydroxycarbamoyl-ethyl)-6-oxo-3,6-dihydro-2-pyridin-1-yl-methyl]-phenyl-benzamide (2) was prepared by the similar procedure described in above Example 74 (See Table 15).

Example 76

Preparation of N-hydroxy-3-[1-(4-dimethylsulfonylamino-benzyl)-2-oxo-1,2,5,6-tetrahydro-pyridin-3-yl]-propionamide (j3)

N-hydroxy-3-[1-(4-dimethylsulfonylamino-benzyl)-2-oxo-1,2,5,6-tetrahydro-pyridin-3-yl]-propionamide (3) was prepared by the similar procedure described in above Example 74 (See Table 15).

Example 77

Preparation of N-hydroxy-3-2-oxo-1-[4-(toluene-4-sulfonylamino)-benzyl-1,2,5,6-tetrahydro-pyridin-3-yl]-propionamide (j4)

N-hydroxy-3-2-oxo-1-[4-(toluene-4-sulfonylamino)-benzyl-1,2,5,6-tetrahydro-pyridin-3-yl]-propionamide (4) was prepared by the similar procedure described in above Example 74 (See Table 15).

TABLE 15

| Example | Chemical structure | NMR spectrum data |
| --- | --- | --- |
| 75 | 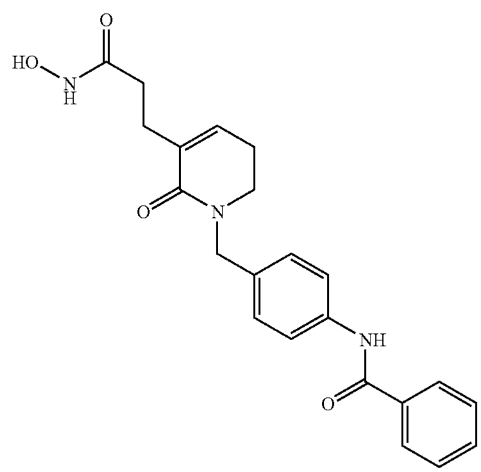 | 7.90(t J=7.05 Hz 2H), 7.67(d, J=8.10 Hz, 2H)7.59-7.47(m, 3H)7.30(d J=8.10 Hz 2H), 6.45(br t, 1H)4.61(s, 2H)3.36(t, J=7.2, 2H)3.30(q, J=1.5 Hz, 4H)2.58(br t, 2H) |
| 76 | 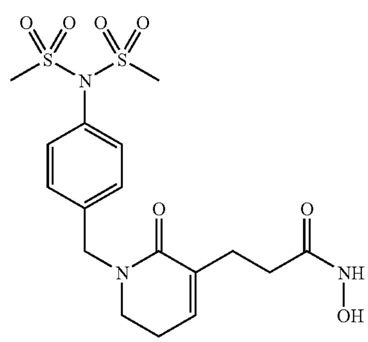 | 7.24(q, J=8.6 Hz, 4H)6.45(br t, 1H)4.58 (s, 2H)3.38-3.29(m, 7H)2.93(s, 3H)2.57 (t, 2H, J=7.1) 2.34-2.24(m, 4H) |
| 77 | 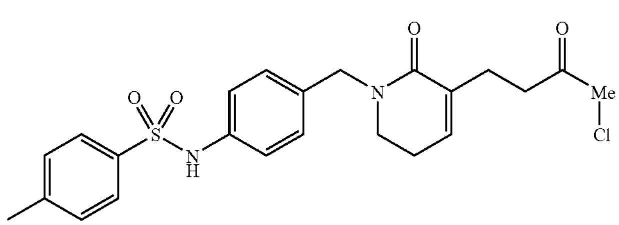 | 7.78(d, J=8.0 Hz, 2H), 7.31(d, J=7.5 Hz, 2H) 7.27-7.21(m, 4H)6.97(t, J=7.2 Hz, 1H)4.61 (d, J=3.5 Hz, 1H)3.47(s, 4H)3.36-3.30 (m, 1H)2.71-2.64(m, 1H)2.51-2.44(m, 3H), 2.32(d, J=4.5 Hz, 1H) |

Example 78

Preparation of 3-[1-(4-acetylamino-benzyl)-2-oxo-1,2,5,6-tetrahydro-pyridin-3-yl]-propionic acid (k)

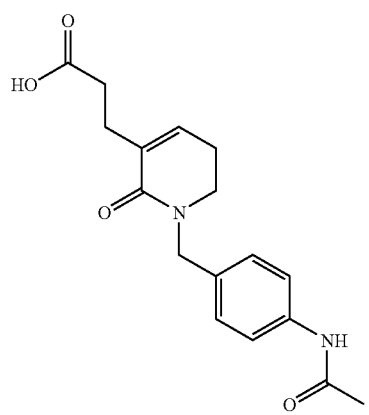

3-[1-(4-acetylamino-benzyl)-2-oxo-1,2,5,6-tetrahydro-pyridin-3-yl]-propionic acid methyl ester (i) prepared by above Step 2 of Example 18 dissolved in organic solvent such as tetrahydrofurane was reacted with LiOH to give 3-[1-(4-acetylamino-benzyl)-2-oxo-1,2,5,6-tetrahydro-pyridin-3-yl]-propionic acid (k).

$^1$H-NMR (300 MHz, CDCl$_3$) δ 7.50 (d J=8.0 Hz 2H), 7.23 (d J=8.6 Hz 2H), 6.45 (t J=4.5 Hz 1H), 4.58 (S 2H), 3.32 (t, J=7.5 Hz, 3H) 2.57 (t, J=7.5 Hz, 2H) 2.46 (t, J=7.5 Hz, 2H)

Example 79

Preparation of 3-[1-(4-benzoylamino-benzyl)-2-oxo-1,2,5,6-tetrahydro-pyridin-3-yl]-propionic acid (k2)

3-[1-(4-benzoylamino-benzyl)-2-oxo-1,2,5,6-tetrahydro-pyridin-3-yl]-propionic acid (k2) was prepared by the similar procedure described in above Example 78 (ee Table 16).

Example 80

Preparation of 3-2-oxo-1-[4-(toluene-4-sulfonylamino)-benzyl]-2-oxo-1,2,5,6-tetrahydro-pyridin-3-yl]-propionic acid (k3)

3-2-oxo-1-[4-(toluenesulfonylamino)-benzyl]-2-oxo-1,2,5,6-tetrahydro-pyridin-3-yl]-propionic acid (k3) was prepared by the similar procedure described in above Example 78 (See Table 16).

TABLE 16

| Example | Chemical structure | NMR spectrum data |
|---|---|---|
| 79 | 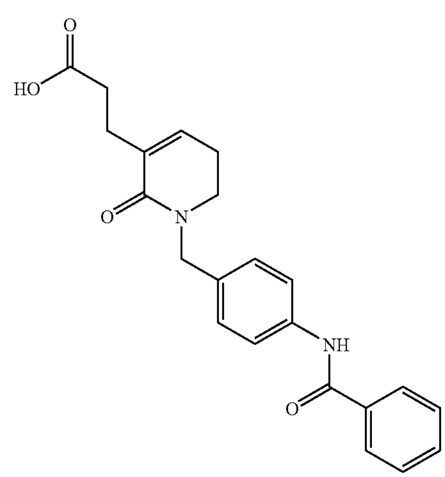 | 7.83(d, J=6.9 Hz, 2H), 7.59(d, J=8.4 Hz, 2H), 7.49-7.37(m, 4H), 7.19(d, J=8.4 Hz, 2H), 6.33(q, J=4.5 Hz, 1H)3.26(t, J=7.2 Hz, 3H)2.54-2.40(m, 4H)2.24(ab, J=11.6 Hz, 3.5 Hz, 2H) |
| 80 | 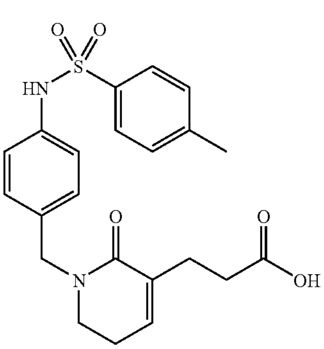 | 7.74(d, J=8.1 Hz, 4H), 7.18(d, J=7.8 Hz, 2H), 6.93(d, J=8.1, 2H), 4.53(s, 2H), 3.20(br t, 2H), 2.40(s, 9H) |

Example 81

Preparation of N-hydroxy-3-(2-oxo-1-phenethyl-piperidine-3-yl)-propionamide (m)

Step 1. Preparation of [1-(2,4-dimethoxybenzyl)-2-oxo-piperidine-3-yl]-acetic acid methyl ester (l)

3-[1-(2,4-dimethoxybenzyl)-2-oxo-1,2,5,6-tetrahydro-pyridin-3-yl]-propionic acid methyl ester was dissolved in alcohol solvent under nitrogen atmosphere. Then Pd—C was added thereto, and the mixture was hydrogenated under a hydrogen balloon for 1 to 2 hrs at room temperature. The reaction mixture was filtered and concentrated in vacuo. The resulting compound was purified with Silica gel column chromatography with a solvent mixture mixed with EtOAc/hexane (1:1) as an eluant to give [1-(2,4-dimethoxy-benzyl)-2-oxo-piperidine-3-yl]-acetic acid methyl ester (l) (yield: 74%).

$^1$H-NMR (300 MHz, CDCl$_3$) δ 7.13 (d, 1H, J=8.4 Hz), 6.42 (d, 2H, J=7.2 Hz), 4.51 (ab, 2H, J=32.9, 7.4 Hz), 3.76 (s, 6H), 3.66 (s, 3H), 3.24-3.18 (m, 2H), 2.93-2.72 (m, 2H), 2.56-2.43 (m, 1H), 1.98-1.55 (m, 4H)

Step 2. Preparation of N-hydroxy-3-(2-oxo-1-phenethyl-piperidine-3-yl)-propionamide (m)

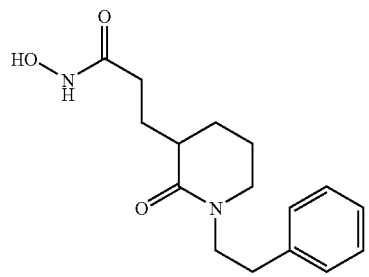

[1-(2,4-dimethoxy-benzyl)-2-oxo-piperidine-3-yl]-acetic acid methyl ester (l) prepared by above Step 1 was reacted with amine salt to give N-hydroxy-3-(2-oxo-1-phenethyl-piperidine-3-yl)-propionamide (m).

$^1$H-NMR (300 MHz, CDCl$_3$) δ 7.26-7.17 (m 5H), 3.61-3.44 (m 2H) 3.08-2.83 (m 4H), 2.56-2.16 (m 4H)

Example 82

Preparation of 2-[1-(2,4-dimethoxy-benzyl)-2-oxo-1,2,5,6-tetrahydro-pyridin-3-yl]-N-hydroxy-acetamide (p1)

Step 1. Preparation of 3-(benzyl-but-3-enyl-carbamoyl)-but-3-enoic acid methyl ester 2-Methylene-pentane dionate-5-methyl ester, EDC and DMAP were added to reaction solution dissolving the but-3-enyl-(2,4-dimethoxybenzyl)amine (b) prepared by above Step 1 of Example 1 in methylene chloride and the mixture was stirred for 5 hrs at room temperature to give 3-(benzyl-but-3-enyl-carbamoyl)-but-3-enoic acid methyl ester (n).

$^1$H-NMR (300 MHz, CDCl$_3$) δ 7.30-7.19 (m, 5H), 5.69 (br t, 1H), 5.23 (s, 2H), 5.00 (t, 2H, J=12.6 Hz), 4.74 (s, 2H), 3.61 (s, 3H), 3.42 (s, 4H), 2.30 (q, 2H, J=7.2 Hz)

Step 2. Preparation of [1-(2,4-dimethoxy-benzyl)-2-oxo-1,2,5,6-tetrahydro-pyridin-3-yl]-acetic acid methyl ester (o)

3-(benzyl-but-3-enyl-carbamoyl)-but-3-enoic acid methyl ester (n) prepared by above Step 1 was added to the catalyst solution containing Gmbb's (I) catalysis such as ruthenium dissolved in organic solvent such as CH$_2$Cl$_2$ to give [1-(2,4-dimethoxy-benzyl)-2-oxo-1,2,5,6-tetrahydro-pyridin-3-yl]-acetic acid methyl ester (o).

$^1$H-NMR (300 MHz, CDCl$_3$) δ 7.17 (d, 1H, J=6.2 Hz), 6.42-6.36 (m, 3H), 4.54 (s, 2H), 3.76 (d, 6H, J=3.0 Hz), 3.66 (s, 3H), 3.35 (t, 2H, J=6.9 Hz), 3.28 (s, 2H), 2.29 (ab, 2H, J=11.3, 3.4 Hz)

Step 3. Preparation of 2-[1-(2,4-dimethoxy-benzyl)-2-oxo-1,2,5,6-tetrahydro-pyridin-3-yl]-N-hydroxy-acetamide (p1)

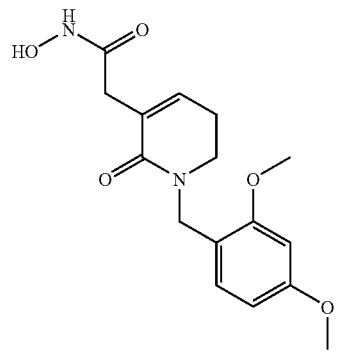

[1-(2,4-dimethoxy-benzyl)-2-oxo-1,2,5,6-tetrahydro-pyridin-3-yl]-acetic acid methyl ester (o) prepared by above Step 2 dissolved in alcohol solvent was reacted with amine salt to give 2-[1-(2,4-dimethoxy-benzyl)-2-oxo-1,2,5,6-tetrahydro-pyridin-3-yl]-N-hydroxy-acetamide (p1).

$^1$H-NMR (300 MHz, CDCl$_3$) δ 7.14 (d, J=8.7 Hz, 1H), 6.54 (br t, 1H) 6.44 (d, J=6.0 Hz, 2H), 4.55 (s, 2H), 3.78 (s, 6H), 3.41-3.32 (m, 2H), 3.20 (s, 2H), 2.0 (d, J=4.5 Hz, 2H)

Example 83

Preparation of 2-(1-benzyl-2-oxo-1,2,5,6-tetrahydro-pyridin-3-yl)-N-hydroxy-acetamide (p2)

2-(1-benzyl-2-oxo-1,2,5,6-tetrahydro-pyridin-3-yl)-N-hydroxy-acetamide (p2) was prepared by the similar procedure described in above Example 82 (See Table 17).

Example 84

Preparation of N-hydroxy-2-[1-(4-nitro-benzyl)-2-oxo-1,2,5,6-tetrahydro-pyridin-3-yl)-N-hydroxy-acetamide (p3)

N-hydroxy-2-[1-(4-nitro-benzyl)-2-oxo-1,2,5,6-tetrahydro-pyridin-3-yl)-N-hydroxy-acetamide (p3) was prepared by the similar procedure described in above Example 82 (See Table 17).

Example 85

Preparation of N-hydroxy-2-[2-oxo-1-(3-phenyl-propyl)-1,2,5,6-tetrahydro-pyridin-3-yl]-N-hydroxy-acetamide (p4)

N-hydroxy-2-[2-oxo-1-(3-phenyl-propyl)-1,2,5,6-tetrahydro-pyridin-3-yl]-N-hydroxy-acetamide (p4) was prepared by the similar procedure described in above Example 82 (See Table 17).

Example 86

Preparation of N-hydroxy-2-[2-oxo-1-(4-phenyl-butyl)-1,2,5,6-tetrahydro-pyridin-3-yl]-N-hydroxy-acetamide (p5)

N-hydroxy-2-[2-oxo-1-(4-phenyl-butyl)-1,2,5,6-tetrahydro-pyridin-3-yl]-N-hydroxy-acetamide (p5) was prepared by the similar procedure described in above Example 82 (See Table 17).

TABLE 17

| Example | Chemical structure | NMR spectrum data |
|---|---|---|
| 83 | 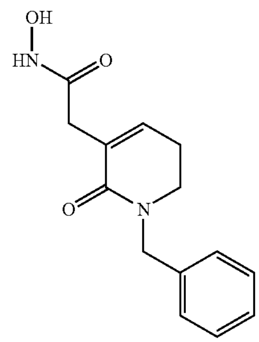 | 7.34-7.22(m, 5H), 6.58(t, J=4.5 Hz, 1H)4.60 (s, 2H)3.39-3.30(m, 3H)3.20(s, 2H)2.39-2.30, (m, 2H) |
| 84 | 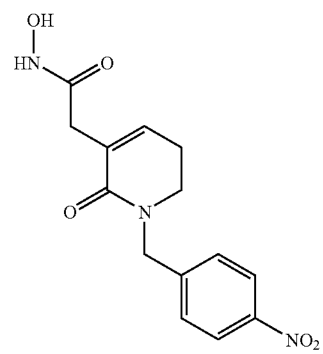 | 8.21(d, J=8.7 Hz, 1H), 7.44(d, J=8.7 Hz, 2H) 6.63(t, J=4.3 Hz, 1H), 4.75(s, 2H), 3.41(ab, J=6.5 Hz, 4H), 2.43(ab, J=6.2 Hz, 2H) |
| 85 | 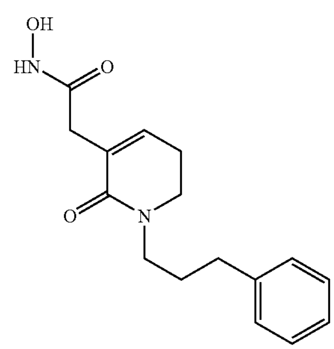 | 7.22(d, J=6.5 Hz, 2H) 7.14(s, 3H), 6.51(br t, 1H)3.43-3.32(m, 5H)3.11(s, 1H)2.59(s, 2H) 2.29(s, 2H)1.84(s, 2H) |
| 86 | 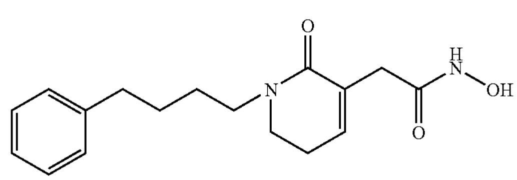 | 7.28-7.13(m, 5H), 6.54(br t, 1H), 3.44-3.31 (m, 5H), 3.14(s, 1H)2.62(t, J=7.1 Hz, 2H), 2.34(s, 2H), 1.58(t, J=3.4 Hz, 4H) |

Example 87

Preparation of [1-(2,4-dimethoxy-benzyl)-2-oxo-1,2,5,6-tetrahydro-pyridin-3-yl]-acetic acid (q1)

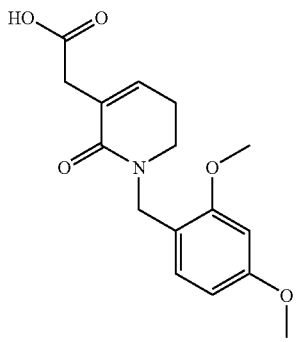

[1-(2,4-dimethoxy-benzyl)-2-oxo-1,2,5,6-tetrahydro-pyridin-3-yl]-acetic acid methyl ester (o) prepared by the Step 2 of Example 26 dissolved in TFA was reacted with LiOH to give [1-(2,4-dimethoxy-benzyl)-2-oxo-1,2,5,6-tetrahydro-pyridin-3-yl]-acetic acid (q1).

$^1$H-NMR (300 MHz, CDCl$_3$) δ7.18 (d, J=8.7 Hz, 1H), 6.54 (t, J=4.3 Hz, 1H), 6.45 (d, J=6.6 Hz, 2H), 4.60 (s, 2H), 3.79 (s, 6H) 3.39 (t, J=7.3 Hz, 2H), 3.34 (s, 2H), 2.32 (ab, J=11.7 Hz, 3.6 Hz, 2H)

Example 88

Preparation of (1-benzyl-2-oxo-1,2,5,6-tetrahydro-pyridin-3-yl)-acetic acid (q2)

(1-benzyl-2-oxo-1,2,5,6-tetrahydro-pyridin-3-yl)-acetic acid (q2) was prepared by the similar procedure described in above Example 87 (See Table 18).

Example 89

Preparation of (2-oxo-1-phenethyl-1,2,5,6-tetrahydro-pyridin-3-yl)-acetic acid (q3)

(2-oxo-1-phenethyl-1,2,5,6-tetrahydro-pyridin-3-yl)-acetic acid (q3) was prepared by the similar procedure described in above Example 87 (See Table 18).

Example 90

Preparation of [2-oxo-1-(3-phenyl-propyl)-1,2,5,6-tetrahydro-pyridin-3-yl]-acetic acid (q4)

[2-oxo-1-(3-phenyl-propyl)-1,2,5,6-tetrahydro-pyridin-3-yl]-acetic acid (q4) was prepared by the similar procedure described in above Example 87 (See Table 18).

Example 91

Preparation of [2-oxo-1-(4-phenyl-butyl)-1,2,5,6-tetrahydro-pyridin-3-yl]-acetic acid (q5)

[2-oxo-1-(4-phenyl-butyl)-1,2,5,6-tetrahydro-pyridin-3-yl]-acetic acid (q5) was prepared by the similar procedure described in above Example 87 (See Table 18).

TABLE 18

| Example | Chemical structure | NMR spectrum data |
|---|---|---|
| 88 | 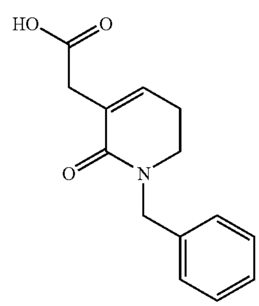 | 7.29-7.18(m 5H)6.50(t, J=4.5 Hz, 1H), 4.58(s, 2H), 3.31(d J=7.2 Hz 4H), 2.29(ab, J=11.0 Hz, 3.5 Hz, 2H) |
| 89 | 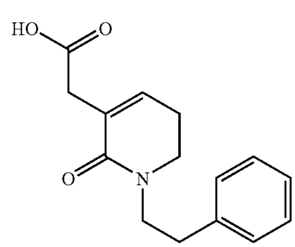 | 7.31-7.18(m, 5H), 6.53(t, J=4.5 Hz, 1H), 3.67(t, J=7.2 Hz, 2H), 3.30(s, 2H), 3.23(t, J=7.2 Hz, 2H)2.90(t, J=7.2 Hz) 2.23(ab, J=11.7 Hz, 3.6 Hz, 2H) |

TABLE 18-continued

| Example | Chemical structure | NMR spectrum data |
|---|---|---|
| 90 | 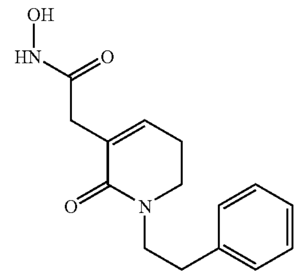 | 7.32-7.12(m, 5H)6.47(br t, 1H)3.56(t, J=10.8 Hz, 2H), 3.11(s, 4H)2.78(d, J=6.0 Hz, 2H)2.14(d, J=10.8 Hz, 2H) |
| 91 | 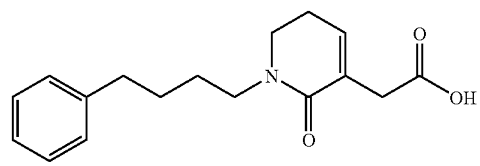 | 7.29-7.14(m, 5H), 6.55(t, J=4.2 Hz, 1H), 3.46(t, J=6.7 Hz, 2H), 3.38(t, J=7.3 Hz, 2H), 3.31(s, 2H)2.64(t, J=7.1 Hz, 2H) 2.37(ab, J=6.3 Hz, 2H)1.67-1.58(m, 4H) |

Example 92

Preparation of 2-[1-(2,4-dimethoxy-benzyl)-2-oxopiperidine-3-yl]-N-hydroxy-acetamide (s1)

Step 1. Preparation of [1-(2,4-dimethoxy-benzyl)-2-oxo-piperidine-3-yl]-acetic acid methyl ester (r)

26 mg of [1-(2,4-dimethoxy-benzyl)-2-oxo-1,2,5,6-tetrahydro-pyridin-3-yl]-acetic acid methyl ester (o) (0.08 mmol) was dissolved in methanol solution under Ar atmosphere. 1.7 mg of 10% Pd—C was added thereto and the mixture was hydrogenated under a hydrogen balloon. The reaction mixture was stirred for 5 hrs at room temperature, filtered and concentrated in vacuo. The resulting compound was purified with Silica gel column chromatography to give 25 mg of [1-(2,4-dimethoxy-benzyl)-2-oxo-piperidine-3-yl]-acetic acid methyl ester (r) (yield: 99%).

$^1$H-NMR (300 MHz, CDCl$_3$) δ 7.13 (d, J=8.4 Hz, 2H), 6.41 (dd, J=8.4 Hz, 2H), 6.41 (s, 1H), 4.51 (dd, J=32.7, 14.9 Hz, 2H), 3.76 (s, 6H), 3.66 (s, 3H), 3.22 (dd, J=7.5, 4.6 Hz, 2H), 2.90 (dd, J=15.9, 5.1 Hz, 1H), 2.76 (m, 1H), 2.52 (dd, J=16.2, 7.5 Hz, 2H), 1.98-1.55 (m, 4H)

Step 2. Preparation of [1-(2,4-dimethoxy-benzyl)-2-oxo-piperidine-3-yl]-N-hydroxy-acetamide (s1)

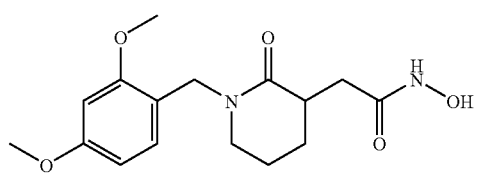

[1-(2,4-dimethoxy-benzyl)-2-oxo-piperidine-3-yl]-acetic acid methyl ester (r) prepared by the Step 1 was reacted with amine salt to give [1-(2,4-dimethoxy-benzyl)-2-oxo-piperidine-3-yl]-N-hydroxy-acetamide (s1).

$^1$H-NMR (300 MHz, CDCl$_3$) δ 7.15 (d, J=9.0 Hz, 1H), 6.46 (t, J=4.65 Hz, 2H), 4.56 (q, J=7.2, 23.7 Hz, 2H), 3.79 (s, 6H), 3.31-3.19 (m, 2H), 2.86-2.69 (m, 2H), 2.41 (d, J=14.1 Hz, 1H), 1.89-1.79 (m, 2H)

Example 93

Preparation of (2-oxo-1-phenethyl-piperidine-3-yl)-N-hydroxy-acetamide (s2)

(2-oxo-1-phenethyl-piperidine-3-yl)-acetic acid (s2) was prepared by the similar procedure described in above Example 92 (See Table 19).

Example 94

Preparation of [2-oxo-1-(3-phenyl-propyl)-piperidine-3-yl]-N-hydroxy-acetamide (s3)

[2-oxo-1-(3-phenyl-propyl)-piperidine-3-yl]-acetic acid (s3) was prepared by the similar procedure described in above Example 92 (See Table 19).

TABLE 19

| Example | Chemical structure | NMR spectrum data |
|---|---|---|
| 93 | 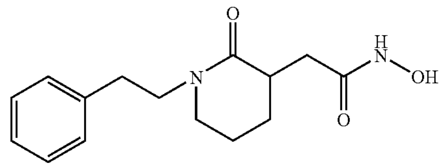 | 7.315-7.169(m, 5H), 3.60(t, J=7.35, 1H) 3.15(dd, J=4.8, 11.1, 1H), 2.917-2.856(m ,1H), 2.728-2.659(m, 1H), 1.698-1.426(m, 4H), 1.23(d, J=7.05, 5H) |
| 94 | 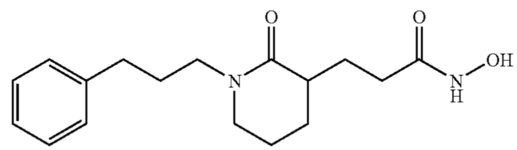 | 7.29-7.12(m, 5H) 3.47-3.35(m, 2H) 3.29-3.23(m, 2H)2.63-2.45(m, 4H) 2.03-1.80(m, 4H) 1.59-1.47(m, 2H), 1.33-1.19(m, 3H) |

Example 95

Preparation of 4-[1-(4-methoxy-benzyl)-2-oxo-1,2,5,6-tetrahydro-pyridin-3-yl]-N-hydroxy-butylamide (v1)

Step 1. Preparation of 5-[(4-methoxy-benzyl)-but-3-enyl-carbamoyl]-hex-5-enoic acid methyl ester (t)

2-Methylene-pentane dionate-5-methyl ester, EDC and DMAP were added to reaction solution dissolving the but-3-enyl-(2,4-dimethoxybenzyl)amine (b) prepared by above Step 1 of Example 1 in methylene chloride solution and the mixture was stirred for 5 hrs at room temperature to give 5-[(4-methoxy-benzyl)-but-3-enyl-carbamoyl]-hex-5-enoic acid methyl ester (t).

Step 2. Preparation of 4-[1-(4-methoxy-benzyl)-2-oxo-1,2,5,6-tetrahydro-pyridin-3-yl]-butyric acid methyl ester (u)

5-[(4-methoxy-benzyl)-but-3-enyl-carbamoyl]-hex-5-enoic acid methyl ester (t) prepared by above Step 1 was added to the catalyst solution containing Grubb's (I) catalysis such as ruthenium dissolved in organic solvent such as $CH_2Cl_2$ to give 4-[1-(4-methoxy-benzyl)-2-oxo-1,2,5,6-tetrahydro-pyridin-3-yl]-butyric acid methyl ester (u).
$^1$H-NMR (300 MHz, $CDCl_3$) δ 7.19 (d, J=8.4 Hz, 2H), 6.83 (d, J=8.4 Hz, 2H), 6.25 (t, J=4.2 Hz, 1H), 4.54 (s, 2H), 3.77 (s, 3H), 3.65 (s, 3H), 3.25 (t, J=6.9 Hz, 2H) 2.33 (t, J=7.3 Hz, 4H), 2.24 (q, J=4.5 Hz, 2H), 1.80 (t, J=7.2 Hz, 2H) 1.56 (s, 2H)

Step 3. Preparation of 4-[1-(4-methoxy-benzyl)-2-oxo-1,2,5,6-tetrahydro-pyridin-3-yl]-N-hydroxy-butylamide (v1)

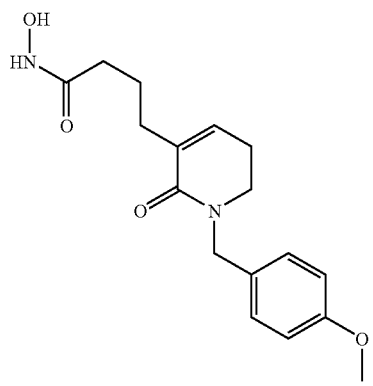

4-[1-(4-methoxy-benzyl)-2-oxo-1,2,5,6-tetrahydro-pyridin-3-yl]-butyric acid methyl ester (u) prepared by Step 2 dissolved in alcohol solvent was reacted with amine salt to give 4-[1-(4-methoxy-benzyl)-2-oxo-1,2,5,6-tetrahydro-pyridin-3-yl]-N-hydroxy-butylamide (v1).
$^1$H-NMR (300 MHz, $CDCl_3$) δ 7.19-7.15 (m, 2H), 6.83 (d, J=7.8 Hz, 2H), 6.28 (br t, 1H), 4.53 (s, 2H), 3.76 (s, 3H), 3.25 (dt, JA=7.5 Hz, JB=1.8 Hz, 2H), 2.38-2.23 (m, 6H), 1.85-1.76 (m, 2H)

Example 96

Preparation of 4 (1-phenethyl-2-oxo-1,2,5,6-tetrahydro-pyridin-3-yl) N-hydroxy-butylamide (v2)

4-(1-phenethyl-2-oxo-1,2,5,6-tetrahydro-pyridin-3-yl)-N-hydroxy-butylamide (v2) was prepared by the similar procedure described in above Example 95 (See Table 20).

Example 97

Preparation of N-hydroxy-4-[2-oxo-1-(3-phenyl-propyl)-1,2,5,6-tetrahydro-pyridin-3-yl]-butylamide (v3)

N-hydroxy-4-[2-oxo-1-(3-phenyl-propyl)-1,2,5,6-tetrahydro-pyridin-3-yl]-butylamide (v3) was prepared by the similar procedure described in above Example 95 (See Table 20).

Example 98

Preparation of N-hydroxy-4-[2-oxo-1-(3-phenyl-butyl)-1,2,5,6-tetrahydro-pyridin-3-yl]-butylamide (v4)

N-hydroxy-4-[2-oxo-1-(3-phenyl-butyl)-1,2,5,6-tetrahydro-pyridin-3-yl]-butylamide (v4) was prepared by the similar procedure described in above Example 95 (See Table 20).

TABLE 20

| Example | Chemical structure | NMR spectrum data |
|---|---|---|
| 96 | (structure) | 7.29-7.13(m, 5H)6.24(br t, 1H), 3.56 (t, J=7.56 Hz, 2H), 3.31-3.29 (m, 1H), 3.16 (t, J=6.9 Hz, 2H), 2.80(t, J=7.2 Hz, 2H), 2.14-2.03 (m, 5H), 1.66-1.61 (m, 2H) |
| 97 | (structure) | 7.29-7.17(m, 5H), 6.32(br t, 1H), 3.46 (t, J=7.3 Hz 2H), 3.35 (t, J=5.9 Hz, 2H), 2.63 (t, J=7.6 Hz, 2H), 2.37-2.28(m, 5H), 1.99-1.73 (m, 5H) |
| 98 | (structure) | 7.29-7.15(m, 5H), 6.31(br t, 1H), 3.45 (t, J=6.5 Hz 2H), 3.32 (t, J=7.1 Hz, 2H), 2.64 (t, J=7.0 Hz, 2H), 2.27(d, J=7.2 Hz, 6H), 1.60 (s, 6H) |

Example 99

Preparation of 3-(2-oxo-1,2,5,6-tetrahydro-pyridin-3-yl)-propionic acid (g)

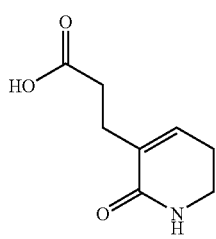

3-(2-oxo-1,2,5,6-tetrahydro-pyridin-3-yl)-propionic acid (g) was dissolved in 0.5 ml of DMF solution. Then BnONH$_2$.HCl (30 mg, 0.188 mmol), diisopropyl methylamine (0.033 ml, 0.189 mmol), EDC (43 mg, 0.224 mmol) and DMAP (5 mg, 0.041 mmol) were added thereto and the mixture was stirred for overnight at room temperature. The mixture was diluted with 7 ml of ethyl acetate and washed with 5% HCl (1 ml) and saturated NaHCO$_3$ solutions (1 ml). The organic layer was dried over anhydrous MgSO$_4$, filtered and concentrated in vacuo. The resulting compound was purified by column chromatography on Silica gel with methanol/chloroform (1:20) solvent mixture as an eluant to give 126 mg (yield: 55%) of the title compound (h).

$^1$H-NMR (300 MHz, CDCl$_3$) δ 9.28 (s, br, 1H), 7.35 (m, 5H), 6.45 (s, br, 1H), 5.70 (s, br, 1H), 4.87 (s, 2H), 3.47 (s, br, 2H), 2.53 (m, 2H), 2.27 (m, 4H)

$^{13}$C-NMR (75 MHz, CDCl$_3$) δ 170.1, 166.9, 137.8, 135.6, 133.0, 129.1, 128.5, 78.0, 39.7, 32.8, 26.9, 24.1

Example 100

Preparation of N-Benzyloxy-3-(2-oxo-1,2,5,6-tetrahydro-pyridin-3-yl)-propionamide (h)

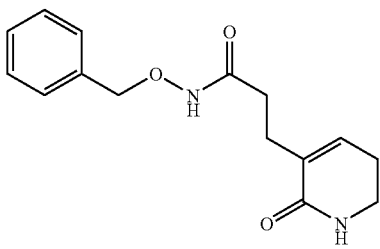

29 mg of 3-(2-oxo-1,2,5,6-tetrahydro-pyridin-3-yl)-propionic acid (g) was dissolved in 0.5 ml of DMF solution (0.171 mM). 30 mg of BnONH$_2$.HCl (0.188 mmol), 0.033 ml of diisopropyl methylamine (0.189 mmol), 43 mg of EDC (0.224 mmol) and 5 mg of DMAP (0.041 mmol) were added thereto and the mixture was stirred for overnight at room temperature. The mixture was diluted with 7 ml of ethyl acetate and washed with 5% HCl (1 ml) and 1 ml of sat. NaHCO$_3$ solution. The organic layer was dried over anhydrous MgSO$_4$, filtered and concentrated in vacuo. The resulting compound was purified by column chromatography on Silica gel with methanol/chloroform (1:20) solvent mixture as an eluant to give 126 mg (yield: 55%) of the title compound (h).

$^1$H-NMR (300 MHz, CDCl$_3$) δ 9.28 (s, br, 1H), 7.35 (m, 5H), 6.45 (s, br, 1H), 5.70 (s, br, 1H), 4.87 (s, 2H), 3.47 (s, br, 2H), 2.53 (m, 2H), 2.27 (m, 4H)

$^{13}$C-NMR (75 MHz, CDCl$_3$) δ 170.1, 166.9, 137.8, 135.6, 133.0, 129.1, 128.5, 78.0, 39.7, 32.8, 26.9, 24.1

Example 101

Preparation of 3-(1-Allyl-2-oxo-1,2,5,6-tetrahydro-pyridin-3-yl)-N-hydroxy-propionamide (j1)

Step 1. Preparation of 3-(2-oxo-1,2,5,6-tetrahydro-pyridin-3-yl)-propionic acid methyl ester (f)

310 mg of 3-[1-(2,4-dimethoxybenzyl)-2-oxo-1,2,5,6-tetrahydro-pyridin-3-yl]-propionic acid methyl ester (d) (0.93 mmol) was dissolved in 3 ml of trifluoroacetic acid solution. Then 0.22 ml of triethyl silane (1.395 mmol) was added thereto and the mixture was heated for 20 min at 80° C. The solvent was removed in vacuo and the remaining residue was diluted in 20 ml of chloroform. The organic layer was washed with 5 ml of sat. NaHCO$_3$ solution and 5 ml of sat. NaCl solution. Then the organic layer was dried over anhydrous MgSO$_4$, filtered and concentrated in vacuo. The resulting compound was purified by column chromatography on Silica gel with EtOAc solvent as an eluant to give 126 mg (yield: 55%) of the title compound (f).

$^1$H-NMR (300 MHz, CDCl$_3$) δ6.64 (s, br, 1H), 6.35 (t, J=3.0 Hz, 1H), 3.59 (s, 3H), 3.31 (m, 2H), 2.48 (m, 4H), 2.26 (m, 2H)

$^{13}$C-NMR (75 MHz, CDCl$_3$) 8173.4, 166.8, 136.1, 133.5, 51.4, 39.5, 33.1, 26.0, 24.0

Step 2. Preparation of 3-(1-allyl-2-oxo-1,2,5,6-tetrahydro-pyridin-3-yl)-propionic acid methyl ester (i1)

0.220 ml of NaHMDS solution (1.0 M in THF, 0.22 mmol) was added to 0.5 ml of the THF solution containing 40 mg of 3-(2-oxo-1,2,5,6-tetrahydro-pyridin-3-yl)-propionic acid methyl ester (0.218 mmol) prepared by the Step 1 in a dropwise manner at −79° C. and stirred at −79° C. for 30 mins. After 0.028 ml of allyl bromide (0.327 mmol) was added to the reaction mixture, the mixture was stirred at 0° C. for 3 hrs. The reaction mixture was quenched by 2 ml of sat. NH$_4$Cl solution, and then the organic layer was extracted with 7 ml of ethyl acetate. The combined organic layer was washed with 2 ml of sat. NH$_4$Cl solution and 2 ml of sat. NaCl solution. Then the organic layer was dried over anhydrous MgSO$_4$, filtered and concentrated in vacuo. The resulting compound was purified by column chromatography on Silica gel with EtOAc/hexane (1:2) solvent mixture as an eluant to give 36 mg (yield: 74%) of the title compound (i1).

$^1$H-NMR (300 MHz, CDCl$_3$) δ 6.28 (m, 1H), 5.74 (m, 1H), 5.14 (m, 2H), 3.99 (d, J=5.7 Hz 2H), 3.61 (s, 3H), 3.27 (t, J=6.9 Hz, 2H), 2.51 (m, 4H), 2.27 (m, 2H)

$^{13}$C-NMR (75 MHz, CDCl$_3$) δ 173.6, 164.6, 134.3, 134.1, 133.3, 117.1, 51.4, 49.0, 44.6, 33.3, 26.6, 23.8

Step 3. Preparation of 3-(1-allyl-2-oxo-1,2,5,6-tetrahydro-pyridin-3-yl)-N-hydroxy-propionamide (j1)

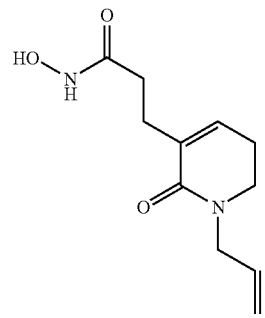

24 mg of 3-(1-allyl-2-oxo-1,2,5,6-tetrahydro-pyridin-3-yl)-propionic acid methyl ester (i1) prepared from the above Step 2 was dissolved in methanol solution (0.11 mmol) and then 0.122 ml of 1.7M NH$_2$OK suspension solution (0.207 mmol) was added thereto at 0° C. and stirred for 3 hrs at room temperature. The resulting mixture was neutralized with 0.02 ml of acetic acid, diluted with 10 ml of ethyl acetate solution, filtered and concentrated in vacuo. The resulting compound was purified by column chromatography on Silica gel with methanol/chloroform (1:10) solvent mixture as an eluant to give 11 mg (yield: 48%) of the title compound (j1).

$^1$H-NMR (300 MHz, CDCl$_3$): δ6.39 (br t, 1H), 5.78-5.67 (m, 1H), 5.17 (d, J=5.4 Hz, 1H), 5.12 (s, 1H), 3.98 (d, J=5.4 Hz, 2H), 3.30 (t, J=7.0 Hz, 2H), 2.54-2.28 (m, 6H)

Example 102

Preparation of N-hydroxy-3-(1-methyl-2-oxo-1,2,5,6-tetrahydro-pyridin-3-yl)-propionamide (i2)

Step 1. Preparation of 3-(1-methyl-2-oxo-1,2,5,6-tetrahydro-pyridin-3-yl)-propionic acid methyl ester (i2)

0.22 ml of 1.0 M NaHMDS solution in THF (0.22 mmol) was added to 0.5 ml of THF solution containing 80 mg 3-(2-oxo-1,2,5,6-tetrahydro-pyridin-3-yl)-propionic acid methyl ester (f) prepared from the step 1 in Example 3 (0.44 mmol) in a dropwise manner at −79° C. and then stirred for 30 min. After 0.48 ml of methyl bromide (0.48 mmol) was added to the reaction mixture, the solution was stirred at 0° C. for 3 hrs. The reaction mixture was quenched by 2 ml of sat. NH$_4$Cl solution and then the organic layer was extracted with ethyl acetate (7 ml). The combined organic layer was washed with 2 ml of sat. NH$_4$Cl solution (2 ml) and 2 ml of sat. NaCl solution subsequently. Then the organic layer was dried over anhydrous MgSO$_4$, filtered and concentrated in vacuo. The resulting compound was purified by column chromatography on Silica gel with EtOAc solvent as an eluant to give 62 mg (yield: 72%) of the title compound (i2).

Step 2. Preparation of N-hydroxy-3-(1-methyl-2-oxo-1,2,5,6-tetrahydro-pyridin-3-yl)-propionamide (j2)

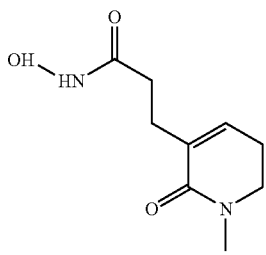

50 mg of 3-(1-methyl-2-oxo-1,2,5,6-tetrahydro-pyridin-3-yl)-propionic acid methyl ester prepared from the above Step 1 was dissolved in methanol (0.25 mmol) and then 0.12 ml of 1.7M $NH_2OK$ suspension solution in methanol (0.21 mmol) was added thereto at 0° C. and the resulting mixture was stirred for 3 hrs at room temperature. The resulting mixture was neutralized with 0.02 ml of acetic acid, diluted with 10 ml of ethyl acetate, filtered and concentrated in vacuo. The resulting compound was purified by column chromatography on Silica gel with methanol/chloroform (1:20) solvent mixture as an eluant to give 19 mg (yield: 35%) of the title compound (j2).

$^1$H-NMR (300 MHz, $CD_3OD$) δ 6.15 (t, J=4.3 Hz, 1H), 3.41 (t, J=7.2 Hz, 2H), 2.97 (s, 3H), 2.51 (t, J=7.5 Hz, 2H), 2.35 (m, 2H), 2.22 (t, J=7.5 Hz, 2H)

Example 103

Preparation of N-hydroxy-3-(1-(naphthalene-2-yl-methyl)-2-oxo-1,2,5,6-tetrahydro-pyridin-3-yl)-propionamide 70 mg of 3-[1-(Naphthyl-2-yl)methyl-2-oxo-1,2,5,6-tetrahydro-pyridin-3-yl]-propionic acid methyl ester was dissolved in methanol solution (0.22 mmol) and then 0.64 ml of 1.7M $NH_2OK$ suspension in methanol (1.08 mmol) was added thereto at 0° C. and the resulting mixture was stirred for 5 hrs at room temperature. The resulting mixture was neutralized with 0.02 ml of acetic acid and concentrated in vacuo. The resulting solid was filtered with 10% methanol/chloroform solvent mixture and concentrated in vacuo. The resulting compound was purified by column chromatography on Silica gel with methanol/chloroform (1:9) solvent mixture as an eluant to give 61 mg (yield: 95%) of the title compound (See Table 21).

Example 104

Preparation of N-hydroxy-3-[2-oxo-1-(2-thiophen-2-yl-ethyl)-1,2,5,6-tetrahydro-pyridin-3-yl]-propionamide 60 mg of 3-[2-oxo-1-(2-thiophen-2-yl)ethyl-1,2,5,6-tetrahydro-pyridin-3-yl]-propionic acid methyl ester was dissolved in methanol to be 0.20 mM solution and then 0.6 ml of 1.7M $NH_2OK$ suspension solution in methanol (1.02 mmol) was added thereto at 0° C. and the resulting mixture was stirred for 5 hrs at room temperature. The resulting mixture was neutralized with 0.02 ml of acetic acid and concentrated in vacuo. The resulting solid was filtered with 10% methanol/chloroform solvent mixture and concentrated in vacuo. The resulting compound was purified by column chromatography on Silica gel with methanol/chloroform (1:9) solvent mixture as an eluant to give 44 mg (yield: 73%) of the title compound (See Table 21).

TABLE 21

| Example | Chemical structure | NMR spectrum data |
| --- | --- | --- |
| 103 | 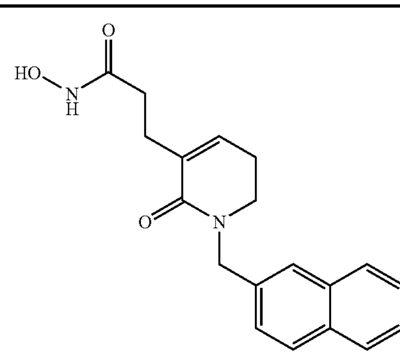 | 8.07-7.99 (m, 1H), 7.83-7.74 (m, 2H), 7.50-7.29 (m, 4H), 6.32 (br t, 1H), 5.01 (s, 2H), 3.44(s, 2H), 3.15 (q, J=6.9 Hz, 2H), 2.71-2.54 (m, 2H), 2.42 (s, 2H), 2.09 (s, 2H) |
| 104 | 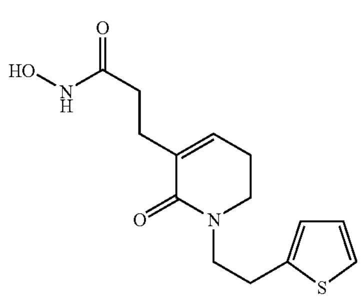 | 7.11 (d, J=4.8 Hz, 1H), 6.89 (t, J=3.9 Hz, 1H), 6.82 (s, 1H), 6.35 (br t, 1H), 3.64-3.59 (m, 2H), 3.22 (t, J=3.22 Hz, 2H), 3.09-3.04 (m, 2H), 2.54-2.50 (m, 2H), 2.35 (s, 2H), 2.20(s, 2H) |

Experimental Example 1

Effect of the Compound of the Present Invention on NO Production

To test the inhibiting activity of the compounds prepared from above Examples 1 to 6 on the production of nitric oxide (NO) caused by activated macrophage by lipopolysaccharide (LPS), the amount of accumulated $NO^{2-}$ in the cells was determined as an indicator of NO production in the medium.

Each 200 µl of RAW 264.7 cells (ATCC, USA), a mouse macrophage cell line was seeded onto each well of 96-well microtiter plate (Nunc, Sweden) to the concentration ranging from $1 \times 10^6$ cells/ml to $5 \times 10^6$ cells/ml, and incubated in DMEM (Dulbeco's modified eagles medium) media containing 5% FBS (fetal bovine serum) at 37° C. in 5% $CO_2$ incubator.

Various concentrations of the compounds of the present invention ranging from 0.10.1 to 10 µM and LPS (Sigma, USA) in the final concentration of 0.3 µg/ml to activate the cell were treated to activate the cell simultaneously. The treated cells were cultured at 37° C. for 24 hours in 5% $CO_2$ incubator and the cultured cells were collected after the cultivation.

And then, to the collected cell culture, an equal volume of Griess reagent (1% sulfanilamide, 0.1% naphthylethylenediamine dihydrochloride, and 2% phosphoric acid) was added and the culture was incubated at room temperature for 10 mins. The amount of nitrite production was determined by measuring the absorbance at 540 nm versus a $NaNO_2$ standard curve. The result was shown in Table 22 (AA: $IC_{50}$'s<1, A: $IC_{50}$'s<5, B: $IC_{50}$'s<10, C: $IC_{50}$'s>10).

As shown in Table 3, it is confirmed that compounds of the present invention effective NO inhibition activity.

TABLE 22

| Example | TNF-alpha inhibition |
|---------|----------------------|
| 1 | B |
| 2 | A |
| 3 | A |
| 4 | AA |
| 5 | A |
| 6 | A |
| 7 | A |
| 8 | A |
| 9 | B |
| 10 | A |
| 11 | AA |
| 12 | AA |
| 13 | A |
| 14 | C |
| 15 | B |
| 16 | C |
| 17 | C |
| 18 | C |
| 19 | B |
| 20 | C |
| 21 | C |
| 22 | C |
| 23 | C |
| 24 | C |
| 25 | C |
| 26 | C |
| 27 | C |
| 28 | A |
| 29 | A |
| 30 | A |
| 31 | C |
| 32 | C |
| 33 | B |
| 34 | A |
| 35 | A |
| 36 | — |
| 37 | — |
| 38 | — |
| 39 | AAA |
| 40 | AA |
| 41 | — |
| 42 | — |
| 43 | A |
| 44 | A |
| 45 | A |
| 46 | B |
| 47 | — |
| 48 | — |
| 49 | AA |
| 50 | C |
| 51 | C |
| 52 | A |
| 53 | AA |
| 54 | A |
| 55 | A |
| 56 | AAA |
| 57 | B |
| 58 | A |
| 59 | A |
| 60 | A |
| 61 | A |
| 62 | AA |
| 63 | C |
| 64 | C |
| 65 | C |
| 66 | C |
| 67 | C |
| 74 | C |
| 75 | C |
| 76 | C |
| 77 | B |
| 78 | A |
| 79 | A |
| 80 | AA |
| 81 | A |
| 82 | A |
| 83 | A |
| 84 | A |
| 85 | B |
| 86 | A |
| 87 | AA |
| 88 | AA |
| 89 | A |
| 90 | C |
| 91 | B |
| 92 | A |
| 93 | A |
| 94 | AA |
| 95 | A |
| 96 | A |
| 97 | A |
| 98 | A |
| 99 | B |
| 100 | A |
| 101 | AA |
| 102 | AA |
| 103 | A |
| 104 | C |

Experimental Example 2

Effect of the Compound of the Present Invention on TNF-alpha

To test the inhibiting activity of the compounds prepared from above Examples on the production of TNF-alpha, the concentration of TNF-alpha in the cell supernatant was measured.

Each 200 μl of RAW 264.7 cells (ATCC, USA), a mouse macrophage cell line was seeded onto each well of 96-well microtiter plate (Nunc, Sweden) to the concentration ranging from $1 \times 10^6$ cells/ml to $5 \times 10^6$ cells/ml, and incubated in DMEM (Dulbeco's modified eagles medium) media containing 5% FBS (fetal bovine serum) at 37° C. in 5% $CO_2$ incubator.

Various concentrations of the compounds of the present invention ranging from 0.10.1 to 10 μM and LPS (Sigma, USA) in the final concentration of 0.3 μg/ml were treated to activated cell simultaneously. The treated cells were cultured at 37° C. for 24 hours in 5% $CO_2$ incubator and the cultured cells were collected after the cultivation And then the concentration of TNF-alpha secreted from the culture supernatant of RAW 264.7 cells was determined by ELISA according to the manufacture's instruction (R&D Systems, Minneapolis, Minn.).

The result was shown in Table 23 (AA: $IC_{50}$'s<1, A: $IC_{50}$'s<5, B: $IC_{50}$'s<10, C: $IC_{50}$'s>10).

As shown in Table 23, it was confirmed that compounds of the present invention showed effective TNF-alpha inhibition activity.

TABLE 23

| Example | TNF-alpha inhibition |
|---|---|
| 1 | B |
| 2 | A |
| 3 | A |
| 4 | AA |
| 5 | A |
| 6 | A |
| 7 | A |
| 8 | A |
| 9 | B |
| 10 | A |
| 11 | AA |
| 12 | AA |
| 13 | A |
| 14 | C |
| 15 | B |
| 16 | C |
| 17 | C |
| 18 | C |
| 19 | B |
| 20 | C |
| 21 | C |
| 22 | C |
| 23 | C |
| 24 | C |
| 25 | C |
| 26 | C |
| 27 | C |
| 28 | A |
| 29 | A |
| 30 | A |
| 31 | C |
| 32 | C |
| 33 | B |
| 34 | A |
| 35 | A |
| 36 | — |
| 37 | — |
| 38 | — |
| 39 | AAA |
| 40 | AA |
| 41 | — |
| 42 | — |
| 43 | A |
| 44 | A |
| 45 | A |
| 46 | B |
| 47 | — |
| 48 | — |
| 49 | AA |
| 50 | C |
| 51 | C |
| 52 | A |
| 53 | AA |
| 54 | A |
| 55 | A |
| 56 | AAA |
| 57 | B |
| 58 | A |
| 59 | A |
| 60 | A |
| 61 | A |
| 62 | AA |
| 63 | C |
| 64 | C |
| 65 | C |
| 66 | C |
| 67 | C |
| 74 | C |
| 75 | C |
| 76 | C |
| 77 | B |
| 78 | A |
| 79 | A |
| 80 | AA |
| 81 | A |
| 82 | A |
| 83 | A |
| 84 | A |
| 85 | B |
| 86 | A |
| 87 | AA |
| 88 | AA |
| 89 | A |
| 90 | C |
| 91 | B |
| 92 | A |
| 93 | A |
| 94 | AA |
| 95 | A |
| 96 | A |
| 97 | A |
| 98 | A |
| 99 | B |
| 100 | A |
| 101 | AA |
| 102 | AA |
| 103 | A |
| 104 | C |

Experimental Example 3

Toxicity Test

Methods

The acute toxicity tests on ICR mice (mean body weight 25±5 g) and Sprague-Dawley rats (235±10 g, Jung-Ang Lab Animal Inc.) were performed using the compounds of example 80. Four group consisting of 10 mice or rats was administrated orally with 4 mg/kg, 40 mg/kg, 400 mg/kg and 4,000 mg/kg of test sample or solvents (0.2 ml, i.p.) respectively and observed for 2 weeks.

Results

There were no treatment-related effects on mortality, clinical signs, body weight changes and gross findings in any group or either gender. These results suggested that the extract prepared in the present invention were potent and safe.

Hereinafter, the formulating methods and kinds of excipients will be described, but the present invention is not limited to them. The representative preparation examples were described as follows.

| Preparation of powder | |
|---|---|
| the compounds of example 80 | 50 mg |
| Lactose | 100 mg |
| Talc | 10 mg |

Powder preparation was prepared by mixing above components and filling sealed package.

| Preparation of tablet | |
|---|---|
| the compounds of example 80 | 50 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| the compounds of example 80 | 50 mg |
| Corn starch | 100 mg |
| Lactose | 100 mg |
| Magnesium Stearate | 2 mg |

Tablet preparation was prepared by mixing above components and filing gelatin capsule by conventional gelatin preparation method.

| Preparation of injection | |
|---|---|
| the compounds of example 80 | 50 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

| Preparation of liquid | |
|---|---|
| the compounds of example 80 | 0.1~80 g |
| Sugar | 5~10 g |
| Citric acid | 0.05~0.3% |
| Caramel | 0.005~0.02% |
| Vitamin C | 0.1~1% |

| -continued | |
|---|---|
| Preparation of liquid | |
| Distilled water | 79~94% |
| $CO_2$ gas | 0.5~0.82% |

Liquid preparation was prepared by dissolving active component, filling all the components and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the 2-oxo-cyclic compound of the present invention have potent anti-inflammatory activity, therefore, it can be used as the therapeutics for treating and preventing the inflammatory disease comprising the pain or inflammation caused by rheumatic disease, for example, rheumatoid arthritis, spondyloarthopathies, gout, osteoarthritis, systemic lupus erythematosus and juvenile arthritis, and inflammatory syndrome for example, from myositis, gingivitis, synovitis, ankylosing spondylitis, burstitis, burns and scar, inflammatory Crohn's disease, Types I diabetes.

What is claimed is:

1. A novel compound represented by the following general formula (II), the pharmaceutically acceptable salt or the isomer thereof:

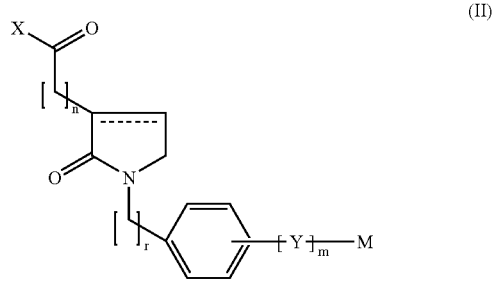

wherein

X is a hydroxyl group, —NHOH, —NHOCH$_2$Ph,

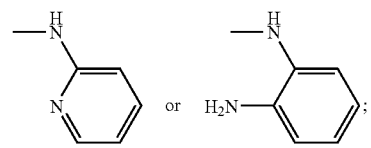

Y is a lower alkyl group, lower alkoxy group, nitro, halogen, amine, acetamide, carbonamide or sulfonamide group;

M is a lower alkyl group or phenyl group substituted with R', of which R' is a hydrogen, lower alkyl or lower alkoxy group;

m and r is independently an integer of 1 to 5 respectively;

n is an integer of 1 to 5; and dotted line (-----) means double bond.

2. The compound according to claim 1, wherein said compound is selected from the group consisting of;
3-[1-(2,4-Dimethoxybenzyl)-2-oxo-2,5-dihydro-1H-pyrrol-3-yl]-N-hydroxypropionamide,
3-(1-benzyl-2-oxo-2,5-dihydro-1H-pyrrol-3-yl)-N-hydroxy-propionamide,
N-hydroxy-3-(2-oxo-1-phenethyl-2,5-dihydro-1H-pyrrol-3-yl)-propionamide,
N-hydroxy-3-[2-oxo-1-(3-phenyl-propyl)-2,5-dihydro-1H-pyrrol-3-yl]-propionamide,
N-hydroxy-3-[2-oxo-1-(4-phenyl-butyl)-2,5-dihydro-1H-pyrrol-3-yl]-propionamide,
N-hydroxy-3-[1-(2-methyl-benzyl)-2-oxo-2,5-dihydro-1H-pyrrol-3-yl]-propionamide,
N-hydroxy-3-[1-(3-methyl-benzyl)-2-oxo-2,5-dihydro-1H-pyrrol-3-yl]-propionamide,
N-hydroxy-3-[1-(4-methyl-benzyl)-2-oxo-2,5-dihydro-1H-pyrrol-3-yl]-propionamide,
N-hydroxy-3-[1-(2-methoxy-benzyl)-2-oxo-2,5-dihydro-1H-pyrrol-3-yl]-propionamide,
N-hydroxy-3-[1-(3-methoxy-benzyl)-2-oxo-2,5-dihydro-1H-pyrrol-3-yl]-propionamide,
N-hydroxy-3-[1-(4-methoxy-benzyl)-2-oxo-2,5-dihydro-1H-pyrrol-3-yl]-propionamide,
3-[1-(4-bromo-benzyl)-2-oxo-2,5-dihydro-1H-pyrrol-3-yl]-N-hydroxy-propionamide,
3-[1-(4-chloro-benzyl)-2-oxo-2,5-dihydro-1H-pyrrol-3-yl]-N-hydroxy-propionamide,
3-[1-(4-benzyloxy-benzyl)-2-oxo-2,5-dihydro-1H-pyrrol-3-yl]-N-hydroxy-propionamide,
N-hydroxy-3-[1-(4-nitro-benzyl)-2-oxo-2,5-dihydro-1H-pyrrol-3-yl]-propionamide,
3-[1-(2,4-dimethoxy-benzyl)-2-oxo-2,5-dihydro-1H-pyrrol-3-yl]-propionic acid,
3-(1-benzyl-2-oxo-2,5-dihydro-1H-pyrrol-3-yl)-propionic acid,
N-{4-[3-(2-hydroxycarbamoyl-ethyl)-2-oxo-2,5-dihydro-pyrrole-1-yl-methyl]-phenyl}-benzamide,
N-hydroxy-3-{2-oxo-1-[4-(toluene-4-sulfonylamino)-benzyl]-2,5-dihydro-1H-pyrrol-3-yl}-propionamide,
2-(1-benzyl-2-oxo-2,5-dihydro-1H-pyrrol-3-yl)-N-hydroxy-acetamide,
2-[1-(2,4-dimethoxy-benzyl)-2-oxo-2,5-dihydro-1H-pyrrol-3-yl]-N-hydroxy-acetamide,
N-hydroxy-2-(2-oxo-1-phenethyl-2,5-dihydro-1H-pyrrol-3-yl)-acetamide,
N-hydroxy-2-[2-oxo-1-(4-phenyl-butyl)-2,5-dihydro-1H-pyrrol-3-yl]-acetamide,
2-[1-(4-benzyloxy-benzyl)-2-oxo-2,5-dihydro-1H-pyrrol-3-yl]-N-hydroxy-acetamide,
3-{1-[2-(2-fluoro-phenyl)-ethyl]-2-oxo-2,5-dihydro-1H-pyrrol-3-yl}-N-hydroxy-propionamide,
3-{1-[2-(3-fluoro-phenyl)-ethyl]-2-oxo-2,5-dihydro-1H-pyrrol-3-yl}-N-hydroxy-propionamide,
3-{1-[2-(4-fluoro-phenyl)-ethyl]-2-oxo-2,5-dihydro-1H-pyrrol-3-yl}-N-hydroxy-propionamide,
N-hydroxy-3-{1-[2-(2-nitro-phenyl)-ethyl]-2-oxo-2,5-dihydro-1H-pyrrol-3-yl}-propionamide,
N-hydroxy-3-{1-[2-(3-nitro-phenyl)-ethyl]-2-oxo-2,5-dihydro-1H-pyrrol-3-yl}-propionamide,
N-hydroxy-3-{1-[2-(4-nitro-phenyl)-ethyl]-2-oxo-2,5-dihydro-1H-pyrrol-3-yl}-propionamide,
3-{1-[2-(2-bromo-phenyl)-ethyl]-2-oxo-2,5-dihydro-1H-pyrrol-3-yl}-N-hydroxy-propionamide,
3-{1-[2-(4-bromo-phenyl)-ethyl]-2-oxo-2,5-dihydro-1H-pyrrol-3-yl}-N-hydroxy-propionamide,
N-hydroxy-3-{1-[2-(2-methoxy-phenyl)-ethyl]-2-oxo-2,5-dihydro-1H-pyrrol-3-yl}-propionamide,
N-hydroxy-3-{1-[2-(3-methoxy-phenyl)-ethyl]-2-oxo-2,5-dihydro-1H-pyrrol-3-yl}-propionamide,
N-hydroxy-3-{1-[2-(4-methoxy-phenyl)-ethyl]-2-oxo-2,5-dihydro-1H-pyrrol-3-yl}-propionamide,
N-hydroxy-3-[2-oxo-1-(2-p-tolyl-ethyl)-2,5-dihydro-1H-pyrrol-3-yl]-propionamide,
N-hydroxy-3-{1-[3-(4-methoxy-phenyl)-propyl]-2-oxo-2,5-dihydro-1H-pyrrol-3-yl}-propionamide,
N-hydroxy-3-[2-oxo-1-(3-o-tolyl-propyl)-2,5-dihydro-1H-pyrrol-3-yl]-propionamide,
N-hydroxy-3-[2-oxo-1-(3-m-tolyl-propyl)-2,5-dihydro-1H-pyrrol-3-yl]-propionamide,
N-hydroxy-3-{1-[3-(4-isopropyl-phenyl)-propyl]-2-oxo-2,5-dihydro-1H-pyrrol-3-yl]-propionamide,
3-{1-[3-(4-bromo-phenyl)-propyl]-2-oxo-2,5-dihydro-1H-pyrrol-3-yl}-N-hydroxy-propionamide,
3-{1-[3-(4-chloro-phenyl)-propyl]-2-oxo-2,5-dihydro-1H-pyrrol-3-yl}-N-hydroxy-propionamide,
N-hydroxy-3-{1-[3-(4-methoxy-phenyl)-propyl]-2-oxo-2,5-dihydro-1H-pyrrol-3-yl}-propionamide,
N-hydroxy-3-{1-[3-(2-methoxy-phenyl)-propyl]-2-oxo-2,5-dihydro-1H-pyrrol-3-yl}-propionamide, and
N-hydroxy-3-{1-[3-(3-methoxy-phenyl)-propyl]-2-oxo-2,5-dihydro-1H-pyrrol-3-yl}-propionamide.

3. A novel compound represented by the following general formula (III), a pharmaceutically acceptable salt or an isomer thereof:

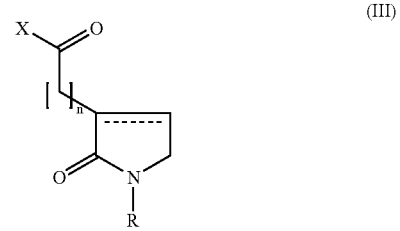

(III)

wherein
X is a hydroxyl group, —NHOH, —NHOCH$_2$Ph,

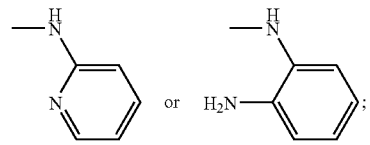

R is a lower alkyl, lower alkenyl, lower alkynyl, lower allyl group, wherein lower consists of C1 to C5 carbon atoms, a heterocyclic group or aromatic aryl group;
n is an integer of 1 to 5; and
dotted line (-----) means double bond.

4. The compound according to claim 3, wherein said R is the group selected from thiophenyl group, naphtyl group, pyrrolyl group, furyl group and biphenyl group.

5. The compound according to claim 4, wherein said compound is selected from the group consisting of;
N-hydroxy-3-(1-naphthalene-2-ylmethyl-2-oxo-2,5-dihydro-1H-pyrrol-3-yl)-propionamide,
N-hydroxy-3-(1-methyl-2-oxo-2,5-dihydro-1H-pyrrol-3-yl)-propionamide, 3-(1-allyl-2-oxo-2,5-dihydro-1H-pyrrol-3-yl)-N-hydroxy-propionamide,
N-hydroxy-3-[1-(2-naphthalene-1-yl-ethyl)-2-oxo-2,5-dihydro-1H-pyrrol-3-yl]-propionamide,
N-hydroxy-3-[1-(2-naphthalene-2-yl-ethyl)-2-oxo-2,5-dihydro-1H-pyrrol-3-yl]-propionamide,
N-hydroxy-3-[2-oxo-1-(2-thiophen-2-yl-ethyl)-2,5-dihydro-1H-pyrrol-3-yl]-propionamide,
3-[1-(3-biphenyl-4-yl-propyl)-2-oxo-2,5-dihydro-1H-pyrrol-3-yl]-N-hydroxy-propionamide, and
N-hydroxy-3-[1-(3-naphthalene-2-yl-propyl)-2-oxo-2,5-dihydro-1H-pyrrol-3-yl]-propionamide.

6. A pharmaceutical composition comprising an efficient amount of the compound represented by general formula (III):

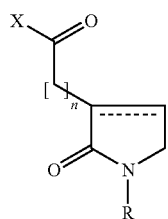
(III)

X is a hydroxyl group, —NHOH, —NHOCH$_2$Ph,

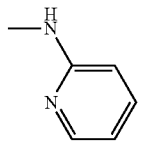 or 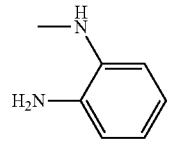

R is a lower alkyl, lower alkenyl, lower alkynyl, lower allyl group wherein lower consists of C1 to C5 carbon atoms, a heterocyclic group or aromatic aryl group;
n is an integer of 1 to 5; and
dotted line (-----) means double bond;
or a pharmaceutically acceptable salt thereof as an active ingredient in amount effective to treat inflammatory diseases together with pharmaceutically acceptable carriers or diluents.

7. A method for treating an inflammatory disease comprising the pain or inflammation caused by rheumatic disease or inflammatory syndrome which comprises administering a therapeutically effective amount of a compound of general formula (III):

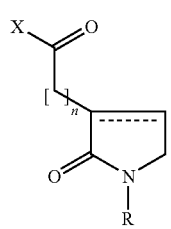
(III)

X is a hydroxyl group, —NHOH, —NHOCH$_2$Ph,

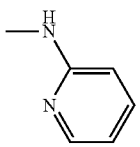 or 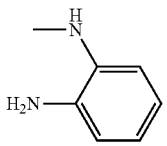

R is a lower alkyl, lower alkenyl, lower alkynyl, lower allyl group wherein lower consists of C1 to C5 carbon atoms, a heterocyclic group or aromatic aryl group;
n is an integer of 1 to 5; and
dotted line (-----) means double bond;
or pharmaceutical acceptable salts thereof to a patient in need of such treatment.

8. A method according to claim 7, wherein said rheumatic disease is selected from rheumatoid arthritis, spondyloarthopathies, gout, osteoarthritis, systemic lupus erythematosus and juvenile arthritis.

9. A method according to claim 7, wherein said inflammatory syndrome is selected from myositis, gingivitis, synovitis, ankylosing spondylitis, burstitis, burns and scar, inflammatory Crohn's disease, and Type I diabetes.

* * * * *